(12) United States Patent
Bondy et al.

(10) Patent No.: US 9,220,710 B2
(45) Date of Patent: Dec. 29, 2015

(54) THERAPEUTIC COMPOUNDS

(71) Applicant: Gilead Sciences, Inc., Foster City, CA (US)

(72) Inventors: Steven S. Bondy, Danville, CA (US); Carina E. Cannizzaro, Foster City, CA (US); Chien-Hung Chou, Livermore, CA (US); John O. Link, San Francisco, CA (US); Qi Liu, Union City, CA (US); Scott D. Schroeder, Union City, CA (US); Winston C. Tse, Redwood City, CA (US); Jennifer R. Zhang, Union City, CA (US)

(73) Assignee: Gilead Sciences, Inc., Foster City, CA (US)

( * ) Notice: Subject to any disclaimer, the term of this patent is extended or adjusted under 35 U.S.C. 154(b) by 0 days.

(21) Appl. No.: 14/151,746

(22) Filed: Jan. 9, 2014

(65) Prior Publication Data

US 2014/0221421 A1 Aug. 7, 2014

Related U.S. Application Data

(60) Provisional application No. 61/750,762, filed on Jan. 9, 2013.

(51) Int. Cl.
| | |
|---|---|
| *C07D 403/12* | (2006.01) |
| *C07D 417/12* | (2006.01) |
| *C07D 413/12* | (2006.01) |
| *A61K 31/437* | (2006.01) |
| *C07D 471/04* | (2006.01) |
| *A61K 31/4178* | (2006.01) |
| *A61K 31/4192* | (2006.01) |
| *A61K 31/4196* | (2006.01) |
| *A61K 31/4245* | (2006.01) |
| *A61K 31/427* | (2006.01) |
| *A61K 45/06* | (2006.01) |

(52) U.S. Cl.
CPC ........... *A61K 31/437* (2013.01); *A61K 31/4178* (2013.01); *A61K 31/4192* (2013.01); *A61K 31/4196* (2013.01); *A61K 31/427* (2013.01); *A61K 31/4245* (2013.01); *A61K 45/06* (2013.01); *C07D 403/12* (2013.01); *C07D 413/12* (2013.01); *C07D 417/12* (2013.01); *C07D 471/04* (2013.01)

(58) Field of Classification Search
CPC ... C07D 403/12; C07D 417/12; C07D 413/12
USPC .................... 548/362.5, 187, 312.1
See application file for complete search history.

(56) References Cited

U.S. PATENT DOCUMENTS

2005/0282805 A1 12/2005 Hangeland et al.

| | | | |
|---|---|---|---|
| 2013/0165489 A1 | 6/2013 | Cocklin et al. |
| 2014/0142085 A1 | 5/2014 | Bondy et al. |
| 2014/0221346 A1 | 8/2014 | Halcomb et al. |
| 2014/0221347 A1 | 8/2014 | Brizgys et al. |

FOREIGN PATENT DOCUMENTS

| | | |
|---|---|---|
| WO | WO-2004/050643 A2 | 6/2004 |
| WO | WO-2004/050643 A3 | 6/2004 |
| WO | WO-2009/062285 A1 | 5/2009 |
| WO | WO-2010/130034 A1 | 11/2010 |
| WO | WO-2012/003497 A1 | 1/2012 |
| WO | WO-2012/003498 A1 | 1/2012 |
| WO | WO-2012/145728 A1 | 10/2012 |
| WO | WO-2013/006738 A1 | 1/2013 |
| WO | WO-2013/006792 A1 | 1/2013 |
| WO | WO-2013/159064 A1 | 10/2013 |
| WO | WO-2014/016358 A1 | 1/2014 |

OTHER PUBLICATIONS

Registry No. 137349-29-2, entered in STN on Nov. 15, 1991.*
Berge, S.M. et al. (Jan. 1977). "Pharmaceutical Salts," *J. Pharma. Sci.* 66(1):1-19.
Hammer, S. et al. (Aug. 6, 2008). "Antiretroviral Treatment of Adult HIV Infection. 2008 Recommendations of the International AIDS Society: USA Panel," *JAMA* 300(5):555-570.
International Search Report mailed on Mar. 21, 2014 for PCT Patent Application No. PCT/US2014/010939, filed on Jan. 9, 2014, four pages.
Kashima, C. et al. (Aug.-Sep. 1991). "New Peptide Synthesis Using the Ozonolysate of 2-(1-Phthalimido)alkyl-5-Phenyloxazoles," *J. Heterocyclic Chem.* 28:1241-1244.
Lemke, C.T. et al. (Jun. 2012). "Distinct Effects of Two HIV-1 Capsid Assembly Inhibitor Families That Bind the Same Site Within the N-Terminal Domain of the Viral CA Protein," *J. Virol.* 86(12):6643-6655.
Smith, R.J. et al. (Feb. 5, 2010; e-pub. Jan. 14, 2010). "Evolutionary Dynamics of Complex Networks of HIV Drug-Resistant Strains: The Case of San Francisco," *Science* 327(5966):697-701.
Taiwo, B. (Sep. 2009; e-pub. Jan. 10, 2009). "Understanding Transmitted HIV Resistance Through the Experience in the USA," *Int'l J. of Infectious Diseases* 13(5):552-559.
Written Opinion of the International Searching Authority mailed on Mar. 21, 2014 for PCT Patent Application No. PCT/US2014/010939, filed on Jan. 9, 2014, six pages.

* cited by examiner

*Primary Examiner* — Shawquia Jackson
(74) *Attorney, Agent, or Firm* — Timothy A. Marquart

(57) ABSTRACT

Compounds of formula I:

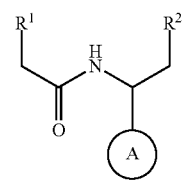

or salts thereof are disclosed. Also disclosed are pharmaceutical compositions comprising a compound of formula I, processes for preparing compounds of formula I, intermediates useful for preparing compounds of formula I and therapeutic methods for treating a Retroviridae viral infection including an infection caused by the HIV virus.

15 Claims, No Drawings

THERAPEUTIC COMPOUNDS

CROSS-REFERENCE TO RELATED APPLICATION

This application claims the benefit of and priority to U.S. Provisional Application Ser. No. 61/750,762, filed Jan. 9, 2013, the disclosure of which is hereby incorporated by reference in its entirety.

BACKGROUND

Positive-single stranded RNA viruses comprising the Retroviridae family include those of the subfamily Orthoretrovirinae and genera *Alpharetrovirus, Betaretrovirus, Gamaretrovirus, Deltaretrovirus, Epsilonretrovirus, Lentivirus,* and *Spumavirus* which cause many human and animal diseases. Among the *Lentivirus*, HIV-1 infection in humans leads to depletion of T helper cells and immune dysfunction, producing immunodeficiency and vulnerability to opportunistic infections. Treating HIV-1 infections with highly active antiretroviral therapies (HAART) has proven to be effective at reducing viral load and significantly delaying disease progression (Hammer, S. M., et al.; *JAMA* 2008, 300: 555-570). However, these treatments do lead to the emergence of HIV strains that are resistant to current therapies (Taiwo, B., *International Journal of Infectious Diseases* 2009, 13:552-559; Smith, R. J., et al., *Science* 2010, 327:697-701). Therefore, there is a pressing need to discover new antiretroviral agents that are active against emerging drug-resistant HIV variants.

SUMMARY

Provided herein are compounds and methods for the treatment of a viral infection. One embodiment provides a compound of formula I:

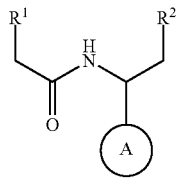

wherein:

A is a 5-membered N-heteroaryl, wherein the 5-membered N-heteroaryl is substituted with one $Z^1$ group and optionally substituted with one or more (e.g., 1, 2 or 3) $Z^2$ groups;

$R^1$ is a bicyclic-heteroaryl or tricyclic-heteroaryl, wherein any bicyclic-heteroaryl, or tricyclic-heteroaryl of $R^1$ is optionally substituted with one or more (e.g., 1, 2, 3, 4 or 5) $Z^3$ groups;

$R^2$ is a phenyl, 5-membered heteroaryl or 6-membered heteroaryl, wherein any phenyl, 5-membered heteroaryl or 6-membered heteroaryl of $R^2$ is optionally substituted with one or more (e.g., 1, 2, 3, 4 or 5) $Z^4$ groups;

$Z^1$ is selected from $(C_3-C_8)$alkyl, aryl, heteroaryl, heterocycle and aryl$(C_1-C_6)$alkyl-, wherein any aryl, heteroaryl, heterocycle and aryl$(C_1-C_6)$alkyl- of $Z^1$ is optionally substituted with one or more (e.g., 1, 2, 3, 4 or 5) $Z^{1a}$ or $Z^{1b}$ groups and wherein any $(C_3-C_8)$alkyl of $Z^1$ is optionally substituted with one or more (e.g., 1, 2, 3, 4 or 5) $Z^{1a}$ groups;

each $Z^{1a}$ is independently selected from $(C_3-C_7)$carbocycle, halogen, —CN, —$OR_{n1}$, —$OC(O)R_{p1}$, —OC(O)$NR_{q1}R_{r1}$, —$SR_{n1}$, —$S(O)R_{p1}$, —$S(O)_2OH$, —$S(O)_2R_{p1}$, —$S(O)_2NR_{q1}R_{r1}$, —$NR_{q1}R_{r1}$, —$NR_{n1}COR_{p1}$, —$NR_{n1}CO_2R_{p1}$, —$NR_{n1}CONR_{q1}R_{r1}$, —$NR_{n1}S(O)_2R_{p1}$, —$NR_{n1}S(O)_2OR_{p1}$, —$NR_{n1}S(O)_2NR_{q1}R_{r1}$, $NO_2$, —$C(O)R_{n1}$, —$C(O)OR_{n1}$ and —$C(O)NR_{q1}R_{r1}$;

each $Z^{1b}$ is independently selected from $(C_1-C_6)$alkyl and $(C_3-C_5)$carbocycle wherein any $(C_1-C_6)$alkyl and $(C_3-C_5)$ carbocycle of $Z^{1b}$ is optionally substituted with one or more (e.g., 1, 2, 3, 4 or 5) halogen;

each $Z^2$ is independently selected from $(C_1-C_3)$alkyl, $(C_1-C_3)$haloalkyl, halogen and —$O(C_1-C_3)$alkyl;

each $Z^3$ is independently selected from $(C_1-C_6)$alkyl, $(C_3-C_7)$carbocycle, halogen, —CN, —$OR_{n2}$, —$OC(O)R_{p2}$, —$OC(O)NR_{q2}R_{r2}$, —$SR_{n2}$, —$S(O)R_{p2}$, —$S(O)_2OH$, —$S(O)_2R_{p2}$, —$S(O)_2NR_{q2}R_{r2}$, —$NR_{q2}R_{r2}$, —$NR_{n2}COR_{p2}$, —$NR_{n2}CO_2R_{p2}$, —$NR_{n2}CONR_{q2}R_{r2}$, —$NR_{n2}S(O)_2R_{p2}$, —$NR_{n2}S(O)_2OR_{p2}$, —$NR_{n2}S(O)_2NR_{q2}R_{r2}$, $NO_2$, —$C(O)R_{n2}$, —$C(O)OR_{n2}$ and —$C(O)NR_{q2}R_{r2}$, wherein any $(C_3-C_7)$ carbocycle and $(C_1-C_6)$alkyl of $Z^3$ is optionally substituted with one or more (e.g., 1, 2, 3, 4 or 5) halogen;

each $Z^4$ is independently selected from $(C_1-C_6)$alkyl, halogen and —$OR_{n3}$, wherein any $(C_1-C_6)$alkyl of $Z^4$ is optionally substituted with one or more (e.g., 1, 2, 3, 4 or 5) halogen;

each $R_{n1}$ is independently selected from H, $(C_1-C_6)$alkyl, $(C_2-C_6)$alkenyl, $(C_2-C_6)$alkynyl and $(C_3-C_7)$carbocycle;

each $R_{p1}$ is independently selected from $(C_1-C_6)$alkyl, $(C_2-C_6)$alkenyl, $(C_2-C_6)$alkynyl and $(C_3-C_7)$carbocycle;

$R_{q1}$ and $R_{r1}$ are each independently selected from H, $(C_1-C_6)$alkyl, $(C_2-C_6)$alkenyl, $(C_2-C_6)$alkynyl and $(C_3-C_7)$carbocycle, or $R_{q1}$ and Rd together with the nitrogen to which they are attached form a 5, 6 or 7-membered heterocycle;

each $R_{n2}$ is independently selected from H, $(C_1-C_6)$alkyl, $(C_2-C_6)$alkenyl, $(C_2-C_6)$alkynyl and $(C_3-C_7)$carbocycle;

each $R_{p2}$ is independently selected from $(C_1-C_6)$alkyl, $(C_2-C_6)$alkenyl, $(C_2-C_6)$alkynyl and $(C_3-C_7)$carbocycle;

$R_{q2}$ and $R_{r2}$ are each independently selected from H, $(C_1-C_6)$alkyl, $(C_2-C_6)$alkenyl, $(C_2-C_6)$alkynyl and $(C_3-C_7)$carbocycle, or $R_{q2}$ and $R_{r2}$ together with the nitrogen to which they are attached form a 5, 6 or 7-membered heterocycle; and each $R_{n3}$ is independently selected from H, $(C_1-C_3)$alkyl, $(C_1-C_3)$haloalkyl, and $(C_3-C_7)$carbocycle;

or a salt thereof;

provided the compound is not 2-(1,3-dioxoisoindolin-2-yl)-N-(2-phenyl-1-(4-phenyloxazol-2-yl)ethyl)acetamide. In certain embodiments, a salt is a pharmaceutically acceptable salt.

One embodiment provides a pharmaceutical composition comprising a compound of formula I or a pharmaceutically acceptable salt thereof, and a pharmaceutically acceptable carrier.

One embodiment provides a method for treating a Retroviridae viral infection (e.g., an HIV viral infection) in a mammal (e.g., a human), comprising administering a compound of formula I, or a pharmaceutically acceptable salt thereof, to the mammal.

One embodiment provides a method for inhibiting the proliferation of the HIV virus, treating AIDS or delaying the onset of AIDS or ARC symptoms in a mammal (e.g., a human), comprising administering a compound of formula I, or a pharmaceutically acceptable salt thereof, to the mammal.

One embodiment provides a method for treating an HIV infection in a mammal (e.g., a human), comprising administering a compound of formula I, or a pharmaceutically acceptable salt thereof, to the mammal.

One embodiment provides a method for treating an HIV infection in a mammal (e.g., a human), comprising administering to the mammal in need thereof a therapeutically effective amount of a compound of formula I, or a pharmaceutically acceptable salt thereof, in combination with a therapeutically effective amount of one or more additional therapeutic agents selected from the group consisting of HIV protease inhibiting compounds, HIV non-nucleoside inhibitors of reverse transcriptase, HIV nucleoside inhibitors of reverse transcriptase, HIV nucleotide inhibitors of reverse transcriptase, HIV integrase inhibitors, gp41 inhibitors, CXCR4 inhibitors, gp120 inhibitors, CCR5 inhibitors, capsid polymerization inhibitors, and other drugs for treating HIV, and combinations thereof.

One embodiment provides a compound of formula I, or a pharmaceutically acceptable salt thereof for use in medical therapy (e.g., for use in treating a Retroviridae viral infection (e.g., an HIV viral infection) or the proliferation of the HIV virus or AIDS or delaying the onset of AIDS or ARC symptoms in a mammal (e.g., a human)).

One embodiment provides a compound of formula I, or a pharmaceutically acceptable salt thereof for use in the manufacture of a medicament for treating a Retroviridae viral infection (e.g., an HIV viral infection) or the proliferation of the HIV virus or AIDS or delaying the onset of AIDS or ARC symptoms in a mammal (e.g., a human).

One embodiment provides a compound of formula I, or a pharmaceutically acceptable salt thereof, for use in the prophylactic or therapeutic treatment of the proliferation of a Retroviridae virus, an HIV virus or AIDS or for use in the therapeutic treatment of delaying the onset of AIDS or ARC symptoms.

One embodiment provides a compound of formula I, or a pharmaceutically acceptable salt thereof, for use in the prophylactic or therapeutic treatment of a Retroviridae virus infection (e.g., an HIV virus infection).

One embodiment provides the use of a compound of formula I, or a pharmaceutically acceptable salt thereof, for the manufacture of a medicament for a Retroviridae virus infection (e.g., an HIV virus infection) in a mammal (e.g., a human).

One embodiment provides processes and intermediates disclosed herein that are useful for preparing compounds of formula I or salts thereof. In certain embodiments, a salt is a pharmaceutically acceptable salt.

Other embodiments, objects, features and advantages will be set forth in the detailed description of the embodiments that follows, and in part will be apparent from the description, or may be learned by practice, of the claimed invention. These objects and advantages will be realized and attained by the processes and compositions particularly pointed out in the written description and claims hereof. The foregoing Summary has been made with the understanding that it is to be considered as a brief and general synopsis of some of the embodiments disclosed herein, is provided solely for the benefit and convenience of the reader, and is not intended to limit in any manner the scope, or range of equivalents, to which the appended claims are lawfully entitled.

DETAILED DESCRIPTION

While the present invention is capable of being embodied in various forms, the description below of several embodiments is made with the understanding that the present disclosure is to be considered as an exemplification of the claimed subject matter, and is not intended to limit the appended claims to the specific embodiments illustrated. The headings used throughout this disclosure are provided for convenience only and are not to be construed to limit the claims in any way.

Embodiments illustrated under any heading may be combined with embodiments illustrated under any other heading.

Definitions

Unless stated otherwise, the following terms and phrases as used herein are intended to have the following meanings:

When trade names are used herein, applicants intend to independently include the tradename product and the active pharmaceutical ingredient(s) of the tradename product.

"Alkyl" is a straight or branched saturated hydrocarbon. For example, an alkyl group can have 1 to 8 carbon atoms (i.e., ($C_1$-$C_8$)alkyl) or 1 to 6 carbon atoms (i.e., ($C_1$-$C_6$ alkyl) or 1 to 4 carbon atoms. Examples of suitable alkyl groups include, but are not limited to, methyl (Me, —$CH_3$), ethyl (Et, —$CH_2CH_3$), 1-propyl (n-Pr, n-propyl, —$CH_2CH_2CH_3$), 2-propyl (i-Pr, i-propyl, —$CH(CH_3)_2$), 1-butyl (n-Bu, n-butyl, —$CH_2CH_2CH_2CH_3$), 2-methyl-1-propyl (i-Bu, i-butyl, —$CH_2CH(CH_3)_2$), 2-butyl (s-Bu, s-butyl, —$CH(CH_3)CH_2CH_3$), 2-methyl-2-propyl t-butyl, —$C(CH_3)_3$), 1-pentyl (n-pentyl, —$CH_2CH_2CH_2CH_2CH_3$), 2-pentyl (—$CH(CH_3)CH_2CH_2CH_3$), 3-pentyl (—$CH(CH_2CH_3)_2$), 2-methyl-2-butyl (—$C(CH_3)_2CH_2CH_3$), 3-methyl-2-butyl (—$CH(CH_3)CH(CH_3)_2$), 3-methyl-1-butyl (—$CH_2CH_2CH(CH_3)_2$), 2-methyl-1-butyl (—$CH_2CH(CH_3)CH_2CH_3$), 1-hexyl (—$CH_2CH_2CH_2CH_2CH_2CH_3$), 2-hexyl (—$CH(CH_3)CH_2CH_2CH_2CH_3$), 3-hexyl (—$CH(CH_2CH_3)(CH_2CH_2CH_3)$), 2-methyl-2-pentyl (—$C(CH_3)_2CH_2CH_2CH_3$), 3-methyl-2-pentyl (—$CH(CH_3)CH(CH_3)CH_2CH_3$), 4-methyl-2-pentyl (—$CH(CH_3)CH_2CH(CH_3)_2$), 3-methyl-3-pentyl (—$C(CH_3)(CH_2CH_3)_2$), 2-methyl-3-pentyl (—$CH(CH_2CH_3)CH(CH_3)_2$), 2,3-dimethyl-2-butyl (—$C(CH_3)_2CH(CH_3)_2$), 3,3-dimethyl-2-butyl (—$CH(CH_3)C(CH_3)_3$, and octyl (—$(CH_2)_7CH_3$).

"Alkenyl" is a straight or branched hydrocarbon with at least one site of unsaturation, e.g. a carbon-carbon, $sp^2$ double bond. For example, an alkenyl group can have 2 to 8 carbon atoms (i.e., $C_2$-$C_8$ alkenyl), or 2 to 6 carbon atoms (i.e., $C_2$-$C_6$ alkenyl). Examples of suitable alkenyl groups include, but are not limited to, ethylene or vinyl (—CH=$CH_2$), allyl (—$CH_2$CH=$CH_2$) and 5-hexenyl (—$CH_2CH_2CH_2CH_2$CH=$CH_2$).

"Alkynyl" is a straight or branched hydrocarbon with at least one site of unsaturation, i.e. a carbon-carbon, sp triple bond. For example, an alkynyl group can have 2 to 8 carbon atoms (i.e., $C_2$-$C_8$ alkyne,), or 2 to 6 carbon atoms (i.e., $C_2$-$C_6$ alkynyl). Examples of suitable alkynyl groups include, but are not limited to, acetylenic (—C≡CH), propargyl (—$CH_2$C≡CH), and the like.

The term "halo" or "halogen" as used herein refers to fluoro, chloro, bromo and iodo.

The term "haloalkyl" as used herein refers to an alkyl as defined herein, wherein one or more hydrogen atoms are each replaced by a halo substituent. For example, a ($C_1$-$C_6$)haloalkyl is a ($C_1$-$C_6$)alkyl wherein one or more of the hydrogen atoms have been replaced by a halo substituent. Such a range includes one halo substituent on the alkyl group to complete halogenation of the alkyl group.

The term "aryl" as used herein refers to a single all carbon aromatic ring or a multiple condensed all carbon ring system wherein at least one of the rings is aromatic. For example, an aryl group can have 6 to 20 carbon atoms, 6 to 14 carbon atoms, or 6 to 12 carbon atoms. Aryl includes a phenyl radical. Aryl also includes multiple condensed ring systems (e.g., ring systems comprising 2, 3 or 4 rings) having about 9 to 20 carbon atoms in which at least one ring is aromatic and wherein the other rings may be aromatic or not aromatic (i.e., carbocycle). Such multiple condensed ring systems may be optionally substituted with one or more (e.g., 1, 2 or 3) oxo groups on any carbocycle portion of the multiple condensed ring system. The rings of the multiple condensed ring system can be connected to each other via fused, spiro and bridged bonds when allowed by valency requirements. It is to be understood that the point of attachment of a multiple condensed ring system, as defined above, can be at any position of the ring system including an aromatic or a carbocycle portion of the ring. Typical aryl groups include, but are not limited to, phenyl, indenyl, naphthyl, 1,2,3,4-tetrahydronaphthyl, anthracenyl, and the like.

"Arylalkyl" refers to an alkyl radical as defined herein in which one of the hydrogen atoms bonded to a carbon atom is replaced with an aryl radical as described herein (i.e., an aryl-alkyl-moiety). The alkyl group of the "arylalkyl" can be 1 to 6 carbon atoms (i.e., aryl($C_1$-$C_6$)alkyl). Arylalkyl groups include, but are not limited to, benzyl, 2-phenylethan-1-yl, 1-phenylpropan-1-yl, naphthylmethyl, 2-naphthylethan-1-yl and the like.

The term "heteroaryl" as used herein refers to a single aromatic ring that has at least one atom other than carbon in the ring, wherein the atom is selected from the group consisting of oxygen, nitrogen and sulfur; the term also includes multiple condensed ring systems that have at least one such aromatic ring, which multiple condensed ring systems are further described below. Thus, the term includes single aromatic rings of from about 1 to 6 carbon atoms and about 1-4 heteroatoms selected from the group consisting of oxygen, nitrogen and sulfur in the rings. The sulfur and nitrogen atoms may also be present in an oxidized form provided the ring is aromatic. Such rings include but are not limited to pyridyl, pyrimidinyl, oxazolyl or furyl. The term also includes multiple condensed ring systems (e.g., ring systems comprising 2, 3 or 4 rings) wherein a heteroaryl group, as defined above, can be condensed with one or more rings selected from heteroaryls (to form for example a naphthyridinyl such as 1,8-naphthyridinyl), heterocycles, (to form for example a 1,2,3,4-tetrahydronaphthyridinyl such as 1,2,3,4-tetrahydro-1,8-naphthyridinyl), carbocycles (to form for example 5,6,7,8-tetrahydroquinolyl) and aryls (to form for example indazolyl) to form the multiple condensed ring system. Thus, a heteroaryl (a single aromatic ring or multiple condensed ring system) has about 1-20 carbon atoms and about 1-6 heteroatoms within the heteroaryl ring. Such multiple condensed ring systems may be optionally substituted with one or more (e.g., 1, 2, 3 or 4) oxo groups on the carbocycle or heterocycle portions of the condensed ring. The rings of the multiple condensed ring system can be connected to each other via fused, spiro and bridged bonds when allowed by valency requirements. It is to be understood that the individual rings of the multiple condensed ring system may be connected in any order relative to one another. It is also to be understood that the point of attachment of a multiple condensed ring system (as defined above for a heteroaryl) can be at any position of the multiple condensed ring system including a heteroaryl, heterocycle, aryl or carbocycle portion of the multiple condensed ring system and at any suitable atom of the multiple condensed ring system including a carbon atom and heteroatom (e.g., a nitrogen). Exemplary heteroaryls include but are not limited to pyridyl, pyrrolyl, pyrazinyl, pyrimidinyl, pyridazinyl, pyrazolyl, thienyl, indolyl, imidazolyl, oxazolyl, thiazolyl, furyl, oxadiazolyl, thiadiazolyl, quinolyl, isoquinolyl, benzothiazolyl, benzoxazolyl, indazolyl, quinoxalyl, quinazolyl, 5,6,7,8-tetrahydroisoquinolinyl, benzofuranyl, benzimidazolyl, thianaphthenyl, triazolyl, isoxazolyl, 4,5,6,7-tetrahydro-indazolyl and pyrrolo[3,2-b]pyridinyl.

The term "N-heteroaryl" refers to a heteroaryl that contains at least one nitrogen atom within the ring system.

The term "heterocyclyl" or "heterocycle" as used herein refers to a single saturated or partially unsaturated ring that has at least one atom other than carbon in the ring, wherein the atom is selected from the group consisting of oxygen, nitrogen and sulfur; the term also includes multiple condensed ring systems that have at least one such saturated or partially unsaturated ring, which multiple condensed ring systems are further described below. Thus, the term includes single saturated or partially unsaturated rings (e.g., 3, 4, 5, 6 or 7-membered rings) from about 1 to 6 carbon atoms and from about 1 to 3 heteroatoms selected from the group consisting of oxygen, nitrogen and sulfur in the ring. The ring may be substituted with one or more (e.g., 1, 2 or 3) oxo groups and the sulfur and nitrogen atoms may also be present in their oxidized forms. Such rings include but are not limited to azetidinyl, tetrahydrofuranyl or piperidinyl. The term "heterocycle" also includes multiple condensed ring systems (e.g., ring systems comprising 2, 3 or 4 rings) wherein a single heterocycle ring (as defined above) can be condensed with one or more groups selected from heterocycles (to form for example a decahydronapthyridinyl), carbocycles (to form for example a decahydroquinolyl) and aryls to form the multiple condensed ring system. Thus, a heterocycle (a single saturated or single partially unsaturated ring or multiple condensed ring system) has about 2-20 carbon atoms and 1-6 heteroatoms within the heterocycle ring. Such multiple condensed ring systems may be optionally substituted with one or more (e.g., 1, 2, 3 or 4) oxo groups on the carbocycle or heterocycle portions of the multiple condensed ring. The rings of the multiple condensed ring system can be connected to each other via fused, spiro and bridged bonds when allowed by valency requirements. It is to be understood that the individual rings of the multiple condensed ring system may be connected in any order relative to one another. It is also to be understood that the point of attachment of a multiple condensed ring system (as defined above for a heterocycle) can be at any position of the multiple condensed ring system including a heterocycle, aryl and carbocycle portion of the ring. It is also to be understood that the point of attachment for a heterocycle or heterocycle multiple condensed ring system can be at any suitable atom of the heterocycle or heterocycle multiple condensed ring system including a carbon atom and a heteroatom (e.g., a nitrogen). Exemplary heterocycles include, but are not limited to aziridinyl, azetidinyl, pyrrolidinyl, piperidinyl, homopiperidinyl, morpholinyl, thiomorpholinyl, piperazinyl, tetrahydrofuranyl, dihydrooxazolyl, tetrahydropyranyl, tetrahydrothiopyranyl, 1,2,3,4-tetrahydroquinolyl, benzoxazinyl, dihydrooxazolyl, chromanyl, 1,2-dihydropyridinyl, 2,3-dihydrobenzofuranyl, 1,3-benzodioxolyl and 1,4-benzodioxanyl.

The term "carbocycle" or "carbocyclyl" refers to a single saturated (i.e., cycloalkyl) or a single partially unsaturated (e.g., cycloalkenyl, cycloalkadienyl, etc.) all carbon ring having 3 to 7 carbon atoms (i.e. ($C_3$-$C_7$)carbocycle). The term "carbocycle" or "carbocyclyl" also includes multiple condensed, saturated and partially unsaturated all carbon ring systems (e.g., ring systems comprising 2, 3 or 4 carbocyclic rings). Accordingly, carbocycle includes multicyclic carbocyles such as a bicyclic carbocycles (e.g., bicyclic carbocycles having about 6 to 12 carbon atoms such as bicyclo[3.1.0]hexane and bicyclo[2.1.1]hexane), and polycyclic carbocycles (e.g tricyclic and tetracyclic carbocycles with up to about 20 carbon atoms). The rings of the multiple condensed ring system can be connected to each other via fused, spiro and bridged bonds when allowed by valency requirements. For example, multicyclic carbocyles can be connected to each other via a single carbon atom to form a spiro connection (e.g., spiropentane, spiro[4,5]decane, etc), via two adjacent carbon atoms to form a fused connection (e.g., carbocycles such as decahydronaphthalene, norsabinane, norcarane) or via two non-adjacent carbon atoms to form a bridged connection (e.g., norbornane, bicyclo[2.2.2]octane, etc). The "carbocycle" or "carbocyclyl" can also be optionally substituted with one or more (e.g., 1, 2 or 3) oxo groups. Non-limiting examples of monocyclic carbocycles include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl and 1-cyclohex-3-enyl.

One skilled in the art will recognize that substituents and other moieties of the compounds of formula I should be selected in order to provide a compound which is sufficiently stable to provide a pharmaceutically useful compound which can be formulated into an acceptably stable pharmaceutical composition. Compounds of formula I which have such stability are contemplated as falling within the scope of the present invention.

The modifier "about" used in connection with a quantity is inclusive of the stated value and has the meaning dictated by the context (e.g., includes the degree of error associated with measurement of the particular quantity). The word "about" may also be represented symbolically by "~" in the context of a chemical measurement (e.g., ~50 mg or pH ~7).

The term "treatment" or "treating," to the extent it relates to a disease or condition includes preventing the disease or condition from occurring, inhibiting the disease or condition, eliminating the disease or condition, and/or relieving one or more symptoms of the disease or condition.

Stereoisomers

Stereochemical definitions and conventions used herein generally follow S. P. Parker, Ed., *McGraw-Hill Dictionary of Chemical Terms* (1984) McGraw-Hill Book Company, New York; and Eliel, E. and Wilen, S., *Stereochemistry of Organic Compounds* (1994) John Wiley & Sons, Inc., New York.

The term "chiral" refers to molecules which have the property of non-superimposability of the mirror image partner, while the term "achiral" refers to molecules which are superimposable on their minor image partner.

The term "stereoisomers" refers to compounds which have identical chemical constitution, but differ with regard to the arrangement of the atoms or groups in space.

"Diastereomer" refers to a stereoisomer with two or more centers or axes of chirality and whose molecules are not mirror images of one another. Diastereomers typically have different physical properties, e.g., melting points, boiling points, spectral properties, and reactivities. Mixtures of diastereomers may separate under high resolution analytical procedures such as electrophoresis and chromatography.

"Enantiomers" refer to two stereoisomers of a compound which are non-superimposable minor images of one another.

The compounds disclosed herein may have chiral centers, e.g., chiral carbon atoms. Such compounds thus include racemic mixtures of all stereoisomers, including enantiomers, diastereomers, and atropisomers. In addition, the compounds disclosed herein include enriched or resolved optical isomers at any or all asymmetric, chiral atoms. Such compositions thus include racemic mixtures of all stereoisomers, including enantiomers, diastereomers, and atropisomers. In addition, the compositions disclosed herein include enriched or resolved optical isomers at any or all asymmetric, chiral atoms. In other words, the chiral centers apparent from the depictions are provided as the chiral isomers or racemic mixtures. Both racemic and diastereomeric mixtures, as well as the individual optical isomers isolated or synthesized, substantially free of their enantiomeric or diastereomeric partners, are all within the scope of the invention. The racemic mixtures can be separated into their individual, substantially optically pure isomers through well-known techniques such as, for example, the separation of diastereomeric salts formed with optically active adjuncts, e.g., acids or bases followed by conversion back to the optically active substances. The desired optical isomer can also be synthesized by means of stereospecific reactions, beginning with the appropriate stereoisomer of the desired starting material.

It is to be understood that for compounds disclosed herein when a bond is drawn in a non-stereochemical manner (e.g., flat) the atom to which the bond is attached includes all stereochemical possibilities. It is also to be understood that when a bond is drawn in a stereochemical manner (e.g., bold, bold-wedge, dashed or dashed-wedge) the atom to which the stereochemical bond is attached has the stereochemistry as shown unless otherwise noted. Accordingly, in one embodiment, a compound disclosed herein is greater than 50% a single enantiomer. In another embodiment, a compound disclosed herein is at least 80% a single enantiomer. In another embodiment, a compound disclosed herein is at least 90% a single enantiomer. In another embodiment, a compound disclosed herein is at least 98% a single enantiomer. In another embodiment, a compound disclosed herein is at least 99% a single enantiomer. In another embodiment, a compound disclosed herein is greater than 50% a single diastereomer. In another embodiment, a compound disclosed herein is at least 80% a single diastereomer. In another embodiment, a compound disclosed herein is at least 90% a single diastereomer. In another embodiment, a compound disclosed herein is at least 98% a single diastereomer. In another embodiment, a compound disclosed herein is at least 99% a single diastereomer.

Accordingly, in one embodiment, a composition disclosed herein is greater than 50% a single enantiomer. In another embodiment, a composition disclosed herein is at least 80% a single enantiomer. In another embodiment, a composition disclosed herein is at least 90% a single enantiomer. In another embodiment, a composition disclosed herein is at least 98% a single enantiomer. In another embodiment, a composition disclosed herein is at least 99% a single enantiomer. In another embodiment, a composition disclosed herein is greater than 50% a single diastereomer. In another embodiment, a composition disclosed herein is at least 80% a single diastereomer. In another embodiment, a composition disclosed herein is at least 90% a single diastereomer. In another embodiment, a composition disclosed herein is at least 98% a single diastereomer. In another embodiment, a composition disclosed herein is at least 99% a single diastereomer.

Tautomers

The compounds disclosed herein can also exist as tautomeric isomers in certain cases. Although only one delocalized resonance structure may be depicted, all such forms are contemplated within the scope of the invention. For example, ene-amine tautomers can exist for purine, pyrimidine, imidazole, guanidine, amidine, and tetrazole systems and all their possible tautomeric forms are within the scope of the invention.

Protecting Groups

"Protecting group" refers to a moiety of a compound that masks or alters the properties of a functional group or the properties of the compound as a whole. Chemical protecting groups and strategies for protection/deprotection are well known in the art. See e.g., *Protective Groups in Organic Chemistry*, Theodora W. Greene, John Wiley & Sons, Inc., New York, 1991. Protecting groups are often utilized to mask the reactivity of certain functional groups, to assist in the efficiency of desired chemical reactions, e.g., making and breaking chemical bonds in an ordered and planned fashion. Protection of functional groups of a compound alters other physical properties besides the reactivity of the protected functional group, such as the polarity, lipophilicity (hydrophobicity), and other properties which can be measured by common analytical tools. Chemically protected intermediates may themselves be biologically active or inactive.

Salts and Hydrates

Examples of pharmaceutically acceptable salts of the compounds disclosed herein include salts derived from an appropriate base, such as an alkali metal (for example, sodium), an alkaline earth metal (for example, magnesium), ammonium and $NX_4^+$ (wherein X is $C_1$-$C_4$ alkyl). Pharmaceutically acceptable salts of a nitrogen atom or an amino group include for example salts of organic carboxylic acids such as acetic, benzoic, lactic, fumaric, tartaric, maleic, malonic, malic, isethionic, lactobionic and succinic acids; organic sulfonic acids, such as methanesulfonic, ethanesulfonic, benzenesulfonic and p-toluenesulfonic acids; and inorganic acids, such as hydrochloric, hydrobromic, sulfuric, phosphoric and sulfamic acids. Pharmaceutically acceptable salts of a compound of a hydroxy group include the anion of said compound in combination with a suitable cation such as $Na^+$ and $NX_4^+$ (wherein each X is independently selected from H or a $C_1$-$C_4$ alkyl group).

A pharmaceutically acceptable salt can refer to a salt of a compound that is pharmaceutically acceptable and that possesses (or can be converted to a form that possesses) the desired pharmacological activity of the parent compound. Examples of pharmaceutically acceptable salts of the compounds disclosed herein include salts derived from an appropriate base, such as an alkali metal (for example, sodium), an alkaline earth metal (for example, magnesium), ammonium and $NX_4^+$ (wherein X is $C_1$-$C_4$ alkyl). Pharmaceutically acceptable salts of a nitrogen atom or an amino group include for example salts of organic carboxylic acids such as acetic, benzoic, camphorsulfonic, citric, glucoheptonic, gluconic, lactic, fumaric, tartaric, maleic, malonic, malic, mandelic, isethionic, lactobionic, succinic, 2-napththalenesulfonic, oleic, palmitic, propionic, stearic, and trimethylacetic acids; organic sulfonic acids, such as methanesulfonic, ethanesulfonic, benzenesulfonic and p-toluenesulfonic acids; and inorganic acids, such as hydrochloric, hydrobromic, sulfuric, nitric, phosphoric and sulfamic acids. Pharmaceutically acceptable salts of a compound of a hydroxy group include the anion of said compound in combination with a suitable cation such as $Na^+$ and $NX_4^+$ (wherein X is independently selected from H or a $C_1$-$C_4$ alkyl group). Pharmaceutically acceptable salts also include salts formed when an acidic proton present in the parent compound is replaced by either a metal ion, e.g., an alkali metal ion, an alkaline earth ion, or an aluminum ion; or coordinates with an organic base such as diethanolamine, triethanolamine, N-methylglucamine and the like. Also included in this definition are ammonium and substituted or quaternized ammonium salts. Representative non-limiting lists of pharmaceutically acceptable salts can be found in S. M. Berge et al., J. Pharma Sci., 66(1), 1-19 (1977), and Remington: The Science and Practice of Pharmacy, R. Hendrickson, ed., 21st edition, Lippincott, Williams & Wilkins, Philadelphia, Pa., (2005), at p. 732, Table 38-5, both of which are hereby incorporated by reference herein.

For therapeutic use, salts of active ingredients of the compounds disclosed herein will typically be pharmaceutically acceptable, i.e., they will be salts derived from a physiologically acceptable acid or base. However, salts of acids or bases which are not pharmaceutically acceptable may also find use, for example, in the preparation or purification of a compound of formula I or another compound disclosed herein. All salts, whether or not derived from a physiologically acceptable acid or base, are within the scope of the present invention.

Metal salts typically are prepared by reacting the metal hydroxide with a compound disclosed herein. Examples of metal salts which are prepared in this way are salts containing $Li^+$, $Na^+$, and $K^+$. A less soluble metal salt can be precipitated from the solution of a more soluble salt by addition of the suitable metal compound.

In addition, salts may be formed from acid addition of certain organic and inorganic acids, e.g., HCl, HBr, $H_2SO_4$, $H_3PO_4$ or organic sulfonic acids, to basic centers, such as amines. Finally, it is to be understood that the compositions herein comprise compounds disclosed herein in their unionized, as well as zwitterionic form, and combinations with stoichiometric amounts of water as in hydrates.

Often crystallizations produce a solvate of the compound of the invention. As used herein, the term "solvate" refers to an aggregate that comprises one or more molecules of a compound of the invention with one or more molecules of solvent. The solvent may be water, in which case the solvate may be a hydrate. Alternatively, the solvent may be an organic solvent. Thus, the compounds of the present invention may exist as a hydrate, including a monohydrate, dihydrate, hemihydrate, sesquihydrate, trihydrate, tetrahydrate and the like, as well as the corresponding solvated forms. The compound of the invention may be true solvates, while in other cases, the compound of the invention may merely retain adventitious water or be a mixture of water plus some adventitious solvent.

Isotopes

It is understood by one skilled in the art that this invention also includes any compound claimed that may be enriched at any or all atoms above naturally occurring isotopic ratios with one or more isotopes such as, but not limited to, deuterium ($^2$H or D). As a non-limiting example, a —$CH_3$ group may be substituted with —$CD_3$.

Specific values listed below for radicals, substituents, and ranges are for illustration only; they do not exclude other defined values or other values within defined ranges for the radicals and substituents.

Compounds of Formula I

A specific group of compounds of formula I are compounds of formula Ia:

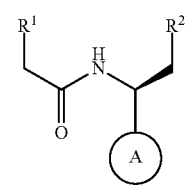

Ia or a salt thereof. In certain embodiments, a salt is a pharmaceutically acceptable salt.

A specific group of compounds of formula I are compounds of formula Ib:

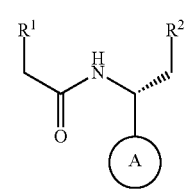

Ib or a salt thereof. In certain embodiments, a salt is a pharmaceutically acceptable salt.

A specific value for A is selected from imidazolyl, 1,2,3-triazolyl, 1,2,4-triazolyl, thiazolyl, 1,2,4-oxadiazolyl, 1,3,4-oxadiazolyl, oxazolyl and isoxazolyl, wherein imidazolyl, 1,2,3-triazolyl, 1,2,4-triazolyl, thiazolyl, 1,2,4-oxadiazolyl, 1,3,4-oxadiazolyl, oxazolyl and isoxazolyl are each substituted with one $Z^1$ group and optionally substituted with one or more (e.g., 1, 2 or 3) $Z^2$ groups.

A specific value for A is selected from imidazol-2-yl, 1,2,3-triazol-4-yl, 1,2,4-triazol-3-yl, thiazol-4-yl, thiazol-5-yl, 1,3,4-oxadiazol-2-yl, 1,2,4-oxadiazol-5-yl, oxazol-5-yl, isoxazol-3-yl, imidazol-4-yl and oxazol-4-yl, wherein imidazol-2-yl, 1,2,3-triazol-4-yl, 1,2,4-triazol-3-yl, thiazol-4-yl, thiazol-5-yl, 1,3,4-oxadiazol-2-yl, 1,2,4-oxadiazol-5-yl, oxazol-5-yl, isoxazol-3-yl, imidazol-4-yl and oxazol-4-yl are each substituted with one $Z^1$ group and optionally substituted with one or more (e.g., 1, 2 or 3) $Z^2$ groups.

A specific value for A is selected from imidazolyl, 1,2,4-triazolyl, thiazolyl, 1,2,4-oxadiazolyl and isoxazolyl, wherein imidazolyl, 1,2,4-triazolyl, thiazolyl, 1,2,4-oxadiazolyl and isoxazolyl are each substituted with one $Z^1$ group and optionally substituted with one or more (e.g., 1, 2 or 3) $Z^2$ groups.

A specific value for A is selected from imidazol-2-yl, 1,2,4-triazol-3-yl, thiazol-4-yl, 1,2,4-oxadiazol-5-yl, isoxazol-3-yl and imidazol-4-yl, wherein imidazol-2-yl, 1,2,4-triazol-3-yl, thiazol-4-yl, 1,2,4-oxadiazol-5-yl, isoxazol-3-yl and imidazol-4-yl are each substituted with one $Z^1$ group and optionally substituted with one or more (e.g., 1, 2 or 3) $Z^2$ groups.

A specific value for the 5-membered N-heteroaryl A is:

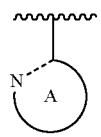

wherein the dashed bond is a single or double bond so that ring A is aromatic, and A is substituted with one $Z^1$ group and optionally substituted with one or more (e.g., 1, 2 or 3) $Z^2$ groups.

A specific value for the 5-membered N-heteroaryl A is:

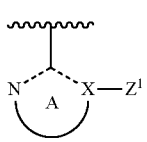

wherein the dashed bonds are single or double bonds so that ring A is aromatic, X is N or C, and A is optionally substituted with one or more (e.g., 1, 2 or 3) $Z^2$ groups.

A specific value for the 5-membered N-heteroaryl A is:

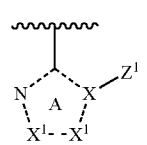

wherein X is N or C, each $X^1$ is independently selected from N, $NZ^{2a}$, O, S and $CZ^{2a}$, the dashed bonds are selected from single and double bonds so that ring A is aromatic, and $Z^{2a}$ is selected from H and $Z^2$.

A specific value for the 5-membered N-heteroaryl A is:

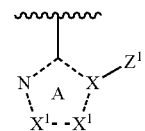

wherein X is N or C, each $X^1$ is independently selected from N, $NZ^{2a}$, O, S and $CZ^{2a}$, the dashed bonds are selected from single and double bonds so that ring A is aromatic, and $Z^{2a}$ is selected from H and $Z^2$; provided that at least one $X^1$ group is other than O or S.

A specific value for A is selected from:

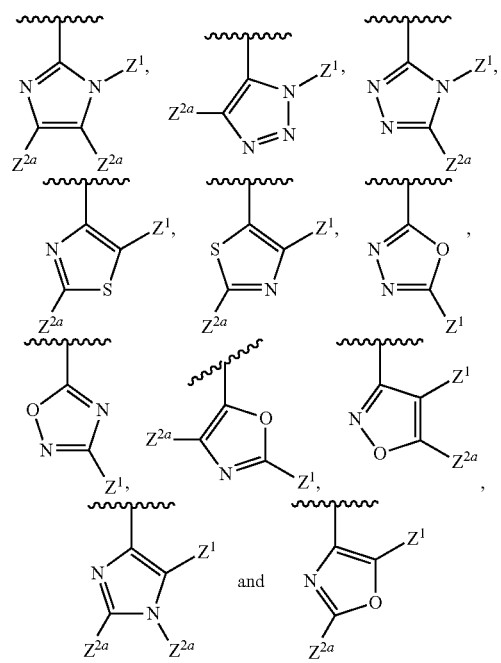

wherein each $Z^{2a}$ is independently selected from $Z^2$ and H.

A specific value for A is selected from

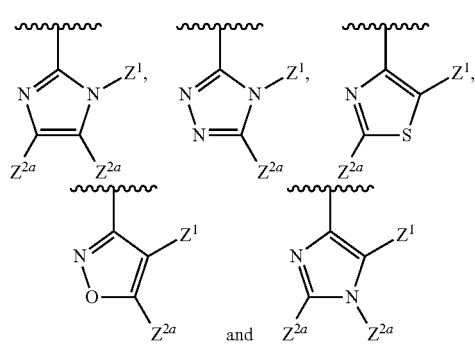

wherein each $Z^{2a}$ is independently selected from $Z^2$ and H.

A specific value for each $Z^1$ is independently selected from $(C_3-C_8)$alkyl, aryl, heteroaryl and aryl$(C_1-C_6)$alkyl-, wherein any aryl, heteroaryl and aryl$(C_1-C_6)$alkyl of $Z^1$ is optionally substituted with one or more (e.g., 1, 2, 3, 4 or 5) $Z^{1a}$ or $Z^{1b}$ groups, and wherein any (C$_3$-C$_8$)alkyl of Z$^1$ is optionally substituted with one or more (e.g., 1, 2, 3, 4 or 5) Z$^{1a}$ groups.

A specific value for each Z$^1$ is independently selected from (C$_3$-C$_8$)alkyl, aryl and aryl(C$_1$-C$_6$)alkyl-, wherein any aryl and aryl(C$_1$-C$_6$)alkyl- of Z$^1$ is optionally substituted with one or more (e.g., 1, 2, 3, 4 or 5) Z$^{1a}$ or Z$^{1b}$ groups, and wherein any (C$_3$-C$_8$)alkyl of Z$^1$ is optionally substituted with one or more (e.g., 1, 2, 3, 4 or 5) Z$^{1a}$ groups.

A specific value for Z$^1$ is independently selected from phenyl and benzyl, wherein any phenyl and benzyl of Z$^1$ is optionally substituted with one or more (e.g., 1, 2, 3, 4 or 5) Z$^{1a}$ or Z$^{1b}$ groups.

A specific value for each Z$^{1a}$ is independently selected from halogen and

A specific value for Z$^{1b}$ is (C$_1$-C$_6$)alkyl.

A specific group of compounds of formula I are compounds wherein each Z$^{1a}$ is independently selected from halogen and —OR$_{n1}$ and each Z$^{1b}$ is (C$_1$-C$_6$)alkyl.

A specific group of compounds of formula I are compounds wherein each Z$^{1a}$ is independently selected from halogen and —OR$_{n1}$, Z$^{1b}$ is (C$_1$-C$_6$)alkyl, and wherein R$_{n1}$ is (C$_1$-C$_6$)alkyl.

A specific value for R$_{n1}$ is (C$_1$-C$_6$)alkyl.

A specific value for R$_{n1}$ is methyl.

A specific value for each Z$^{1a}$ is independently selected from chloro and methoxy and each Z$^{1b}$ is methyl.

A specific value for each Z$^2$ is independently selected from (C$_1$-C$_3$)alkyl.

A specific value for Z$^2$ is methyl.

A specific value for A is selected from

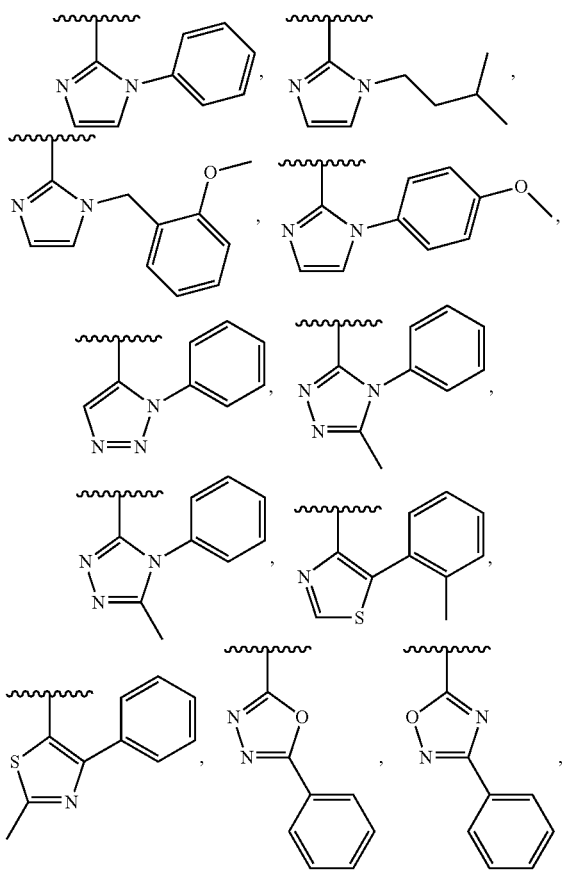

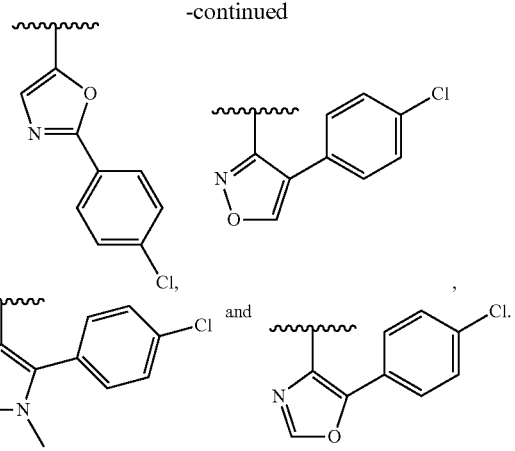

A specific value for A is selected from

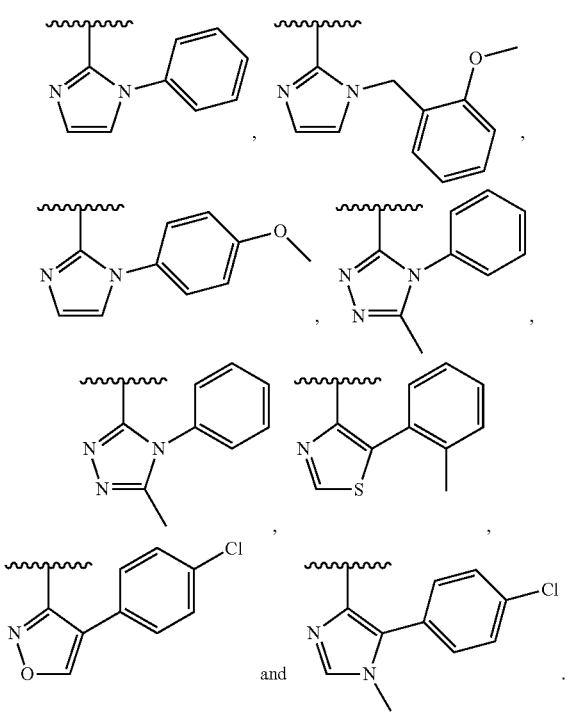

A specific value for R$^2$ is phenyl or a 5-membered heteroaryl, wherein any phenyl or 5-membered heteroaryl is optionally substituted with one or more (e.g., 1, 2, 3, 4 or 5) Z$^4$ groups.

A specific value for R$^2$ is phenyl optionally substituted with one or more (e.g., 1, 2, 3, 4 or 5) Z$^4$ groups.

A specific value for each Z$^4$ is halogen.

A specific value for Z$^4$ is fluoro.

A specific value for R$^2$ is 3,5-difluorophenyl.

A specific value for R$^1$ is bicyclic-heteroaryl, wherein any bicyclic-heteroaryl of R$^1$ is optionally substituted with one or more (e.g., 1, 2, 3, 4 or 5) Z$^3$ groups.

A specific value for R$^1$ is a bicyclic-heteroaryl or tricyclic-heteroaryl, wherein any bicyclic-heteroaryl or tricyclic-heteroaryl of R$^1$ is optionally substituted with one or more (e.g., 1, 2, 3, 4 or 5) Z$^3$ groups.

A specific value for R$^1$ is bicyclic-heteroaryl, wherein one ring of the bicyclic-heteroaryl is a partially unsaturated ring, and wherein the bicyclic-heteroaryl is optionally substituted with one or more (e.g., 1, 2, 3, 4 or 5) $Z^3$ groups.

A specific value for $R^1$ is bicyclic-heteroaryl or tricyclic-heteroaryl, wherein one ring of the bicyclic-heteroaryl or tricyclic-heteroaryl is a partially unsaturated ring, and wherein the bicyclic-heteroaryl or tricyclic-heteroaryl is optionally substituted with one or more (e.g., 1, 2, 3, 4 or 5) $Z^3$ groups.

A specific value for $R^1$ is bicyclic-heteroaryl, wherein the bicyclic-heteroaryl is a 5-membered ring fused to a 6-membered ring, wherein the 5-membered ring fused to a 6-membered ring is optionally substituted with one or more (e.g., 1, 2, 3, 4 or 5) $Z^3$ groups.

A specific value for $R^1$ is bicyclic-heteroaryl, wherein the bicyclic-heteroaryl is a 5-membered aromatic ring fused to a 6-membered ring, wherein the 5-membered ring fused to a 6-membered ring is optionally substituted with one or more (e.g., 1, 2, 3, 4 or 5) $Z^3$ groups.

A specific value for $R^1$ is bicyclic-heteroaryl, wherein the bicyclic-heteroaryl has 4 to 12 carbon atoms and 1-5 heteroatoms within the bicyclic-heteroaryl ring system, and wherein the bicyclic-heteroaryl is optionally substituted with one or more $Z^3$ groups.

A specific value for $R^1$ is bicyclic-heteroaryl or tricyclic-heteroaryl, wherein the bicyclic-heteroaryl or tricyclic-heteroaryl has 4 to 12 carbon atoms and 1-5 heteroatoms within the bicyclic-heteroaryl or tricyclic-heteroaryl ring, and wherein the bicyclic-heteroaryl or tricyclic-heteroaryl is optionally substituted with one or more $Z^3$ groups.

A specific value for $R^1$ is a bicyclic-heteroaryl or tricyclic-heteroaryl, wherein the bicyclic-heteroaryl or tricyclic-heteroaryl has 4-9 carbon atoms and 1-5 heteroatoms in the ring system, and wherein any bicyclic-heteroaryl or tricyclic-heteroaryl of $R^1$ is optionally substituted with one or more (e.g., 1, 2, 3, 4 or 5) $Z^4$ groups.

A specific value for $R^1$ is a bicyclic-heteroaryl or tricyclic-heteroaryl, wherein the bicyclic-heteroaryl or tricyclic-heteroaryl has 6-9 carbon atoms and 1-3 heteroatoms in the ring system, and wherein any bicyclic-heteroaryl or tricyclic-heteroaryl of $R^1$ is optionally substituted with one or more (e.g., 1, 2, 3, 4 or 5) $Z^3$ groups.

A specific value for $R^1$ is bicyclic-heteroaryl, wherein the bicyclic-heteroaryl has 4 to 10 carbon atoms and 1-5 heteroatoms within the bicyclic-heteroaryl ring system, and wherein the bicyclic-heteroaryl is optionally substituted with one or more $Z^3$ groups.

A specific value for $R^1$ is bicyclic-heteroaryl, wherein the bicyclic-heteroaryl has 6 to 9 carbon atoms and 1-4 heteroatoms within the bicyclic-heteroaryl ring system, and wherein the bicyclic-heteroaryl is optionally substituted with one or more $Z^3$ groups.

A specific value for $R^1$ is selected from indolyl, 4,5,6,7-tetrahydro-indazolyl, benzo[d]imidazolyl and pyrrolo[3,2-b]pyridinyl, wherein any indolyl, 4,5,6,7-tetrahydro-indazole, benzo[d]imidazolyl and pyrrolo[3,2-b]pyridinyl of $R^1$ is optionally substituted with one or more (e.g., 1, 2, 3, 4 or 5) $Z^3$ groups.

A specific value for $R^1$ is selected from indolyl, 4,5,6,7-tetrahydro-indazolyl, benzo[d]imidazolyl, pyrrolo[3,2-b]pyridinyl, 3b,4,4a,5-tetrahydro-cyclopropa[3,4]cyclopenta[1,2-c]pyrazole and 1,4,5,5a,6,6a-hexahydrocyclopropa[g]indazole wherein any indolyl, 4,5,6,7-tetrahydro-indazolyl, benzo[d]imidazolyl, pyrrolo[3,2-b]pyridinyl, 3b,4,4a,5-tetrahydro-cyclopropa[3,4]cyclopenta[1,2-c]pyrazole and 1,4,5,5a,6,6a-hexahydrocyclopropa[g]indazole of $R^1$ is optionally substituted with one or more (e.g., 1, 2, 3, 4 or 5) $Z^3$ groups.

A specific value for $R^1$ is selected from indol-3-yl, 4,5,6,7-tetrahydro-1H-indazol-lyl, benzo[d]imidazol-1-yl and 1H-pyrrolo[3,2-b]pyridin-3-yl, wherein any indol-3-yl, 4,5,6,7-tetrahydro-1H-indazol-lyl, benzo[d]imidazole-1-yl and 1H-pyrrolo[3,2-b]pyridine-3-yl of $R^1$ is optionally substituted with one or more (e.g., 1, 2, 3, 4 or 5) $Z^3$ groups.

A specific value for $R^1$ is selected from indol-3-yl, 4,5,6,7-tetrahydro-1H-indazol-1yl, benzo[d]imidazol-1-yl, 1H-pyrrolo[3,2-b]pyridin-3-yl, 4,5,6,7-tetrahydro-1H-indazol-1-yl, 3b,4,4a,5-tetrahydro-1H-cyclopropa[3,4]cyclopenta[1,2-c]pyrazol-1-yl and 1,4,5,5a,6,6a-hexahydrocyclopropa[g]indazol-1-yl wherein any indol-3-yl, 4,5,6,7-tetrahydro-1H-indazol-lyl, benzo[d]imidazol-1-yl, 1H-pyrrolo[3,2-b]pyridin-3-yl, 4,5,6,7-tetrahydro-1H-indazol-1-yl, 3b,4,4a,5-tetrahydro-1H-cyclopropa[3,4]cyclopenta[1,2-c]pyrazol-1-yl and 1,4,5,5a,6,6a-hexahydrocyclopropa[g]indazol-1-yl of $R^1$ is optionally substituted with one or more (e.g., 1, 2, 3, 4 or 5) $Z^3$ groups.

A specific value for each $Z^3$ is independently selected from $(C_1-C_6)$alkyl, halogen and $OR_{n2}$, wherein any $(C_1-C_6)$alkyl of $Z^3$ is optionally substituted with one or more (e.g., 1, 2, 3, 4 or 5) halogen.

A specific value for each $Z^3$ is independently selected from $(C_1-C_6)$alkyl, halogen, —CN and $OR_{n2}$, wherein any $(C_1-C_6)$alkyl of $Z^3$ is optionally substituted with one or more (e.g., 1, 2, 3, 4 or 5) halogen.

A specific group of compounds of formula I are compounds wherein each $Z^3$ is independently selected from $(C_1-C_6)$alkyl, halogen and $OR_{n2}$, wherein any $(C_1-C_6)$alkyl of $Z^3$ is optionally substituted with one or more halogen and wherein $R_{n2}$ is hydrogen or $(C_1-C_6)$alkyl.

A specific group of compounds of formula I are compounds wherein each $Z^3$ is independently selected from $(C_1-C_6)$alkyl, halogen, —CN and $OR_{n2}$, wherein any $(C_1-C_6)$alkyl of $Z^3$ is optionally substituted with one or more halogen and wherein $R_{n2}$ is hydrogen or $(C_1-C_6)$alkyl.

A specific value for $R_{n2}$ is hydrogen or $(C_1-C_6)$alkyl.

A specific value for $R_{n2}$ is hydrogen or methyl.

A specific value for each $Z^3$ is independently selected from fluoro, hydroxy, trifluoromethyl, methyl and methoxy.

A specific value for each $Z^3$ is independently selected from fluoro, hydroxy, trifluoromethyl, methyl, —CN and methoxy.

A specific value for $R^1$ is selected from:

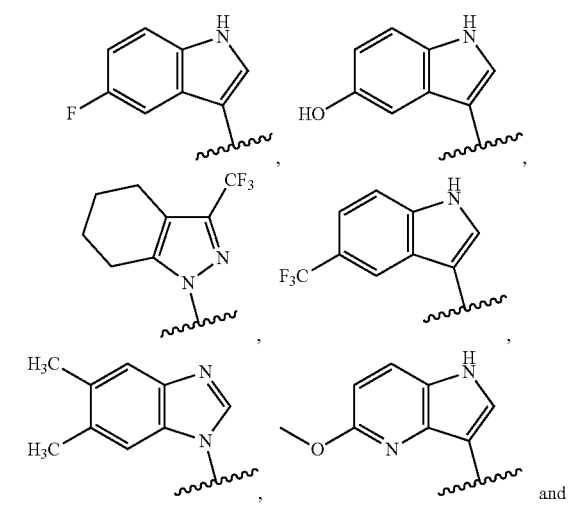

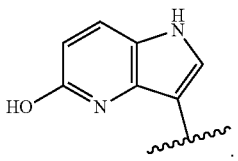

A specific value for $R^1$ is selected from:

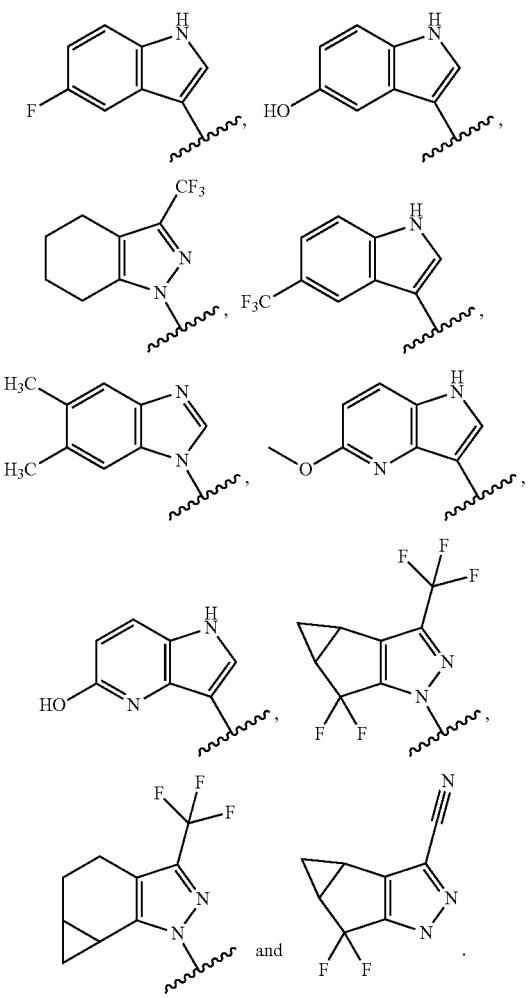

A specific value for $R^1$ is selected from:

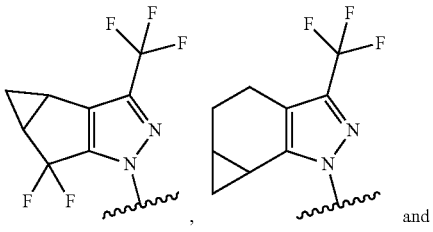

and

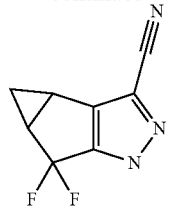

A specific value for $R^1$ is bicyclic-heteroaryl, wherein the bicyclic-heteroaryl has 2 to 14 carbon atoms and 1-5 heteroatoms within the bicyclic-heteroaryl ring system, wherein the bicyclic-heteroaryl is optionally substituted with one or more (e.g., 1, 2, 3, 4 or 5) $Z^3$ groups.

A specific value for $R^1$ is bicyclic-heteroaryl, wherein the bicyclic-heteroaryl has 4 to 12 carbon atoms and 1-5 heteroatoms within the bicyclic-heteroaryl ring system, wherein the bicyclic-heteroaryl is optionally substituted with one or more (e.g., 1, 2, 3, 4 or 5) $Z^3$ groups.

A specific value for $R^1$ is bicyclic-heteroaryl, wherein the bicyclic-heteroaryl has 4 to 10 carbon atoms and 1-5 heteroatoms within the bicyclic-heteroaryl ring system, wherein the bicyclic-heteroaryl is optionally substituted with one or more (e.g., 1, 2, 3, 4 or 5) $Z^3$ groups.

A specific value for $R^1$ is bicyclic-heteroaryl, wherein the bicyclic-heteroaryl has 4 to 8 carbon atoms and 1-5 heteroatoms within the bicyclic-heteroaryl ring system, wherein the bicyclic-heteroaryl is optionally substituted with one or more (e.g., 1, 2, 3, 4 or 5) $Z^3$ groups.

A specific value for $R^1$ is a value for $R^1$ as depicted in any or all of the examples as described herein below.

A specific value for $R^2$ is a value for $R^2$ as depicted in any or all of the examples as described herein below.

A specific value for A is a value for A as depicted in any or all of the examples as described herein below.

One embodiment provides a compound of formula I as described in any or all of the examples as described herein below.

One embodiment provides an isomer (e.g., stereoisomer such as an enantiomer or diastereomer) of a compound of formula I as described in any or all of the examples as described herein below.

One embodiment provides a racemic mixture of a compound of formula I as described in any or all of the examples as described herein below.

In one embodiment a heteroaryl is a monocyclic-heteroaryl, bicyclic-heteroaryl or tricyclic-heteroaryl.

In one embodiment a heteroaryl is a bicyclic-heteroaryl or tricyclic-heteroaryl.

In one embodiment a heteroaryl is a monocyclic-heteroaryl or bicyclic-heteroaryl.

In one embodiment a heteroaryl is a monocyclic-heteroaryl.

In one embodiment a heteroaryl is a bicyclic-heteroaryl.

In one embodiment a heteroaryl is a tricyclic-heteroaryl.

In one embodiment a heterocycle is a monocyclic-heterocycle, bicyclic-heterocycle or tricyclic-heterocycle.

In one embodiment a heterocycle is a bicyclic-heterocycle or tricyclic-heterocycle.

In one embodiment a heterocycle is a monocyclic-heterocycle or bicyclic-heterocycle.

In one embodiment a heterocycle is a monocyclic-heterocycle.

In one embodiment a heteroaryl is a bicyclic-heterocycle.

In one embodiment a heteroaryl is a tricyclic-heterocycle.

In one embodiment a heteroaryl has 1 to 14 carbon atoms and 1-5 heteroatoms within the ring system.

In one embodiment a heteroaryl has 1 to 12 carbon atoms and 1-5 heteroatoms within the ring system.

In one embodiment a heteroaryl has 1 to 10 carbon atoms and 1-5 heteroatoms within the ring system.

In one embodiment a heteroaryl has 1 to 8 carbon atoms and 1-5 heteroatoms within the ring system.

In one embodiment a heteroaryl has 1 to 6 carbon atoms and 1-5 heteroatoms within the ring system.

In one embodiment a heterocycle has 2 to 14 carbon atoms and 1-5 heteroatoms within the ring system.

In one embodiment a heterocycle includes 2 to 12 carbon atoms and 1-5 heteroatoms within the ring system.

In one embodiment a heterocycle includes 2 to 10 carbon atoms and 1-5 heteroatoms within the ring system.

In one embodiment a heterocycle includes 2 to 8 carbon atoms and 1-5 heteroatoms within the ring system.

In one embodiment a heterocycle includes 2 to 6 carbon atoms and 1-5 heteroatoms within the ring system.

One embodiment provides a compound selected from:

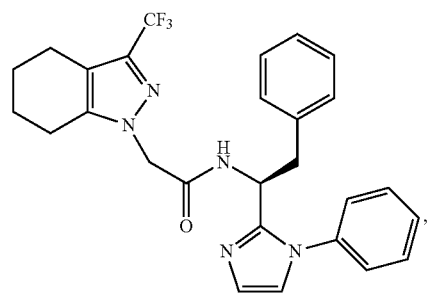

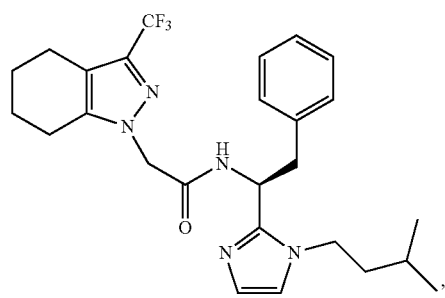

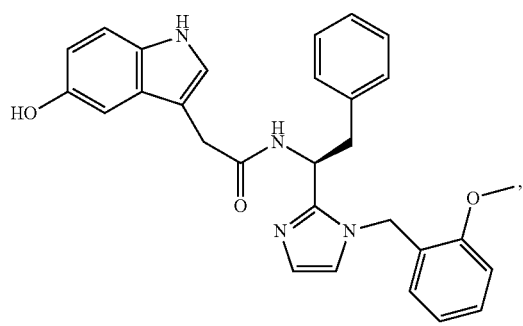

-continued

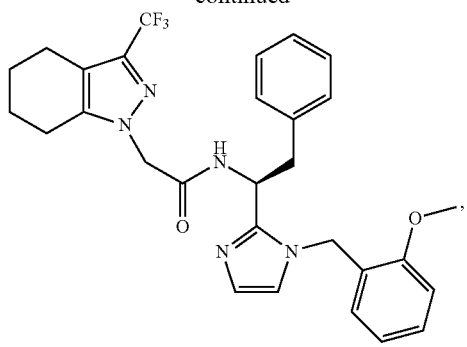

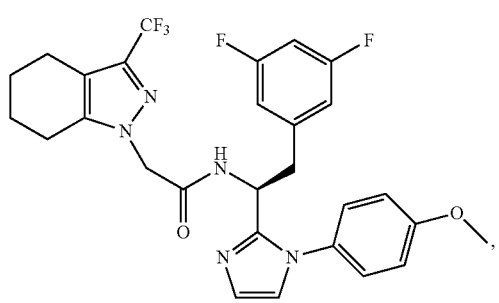

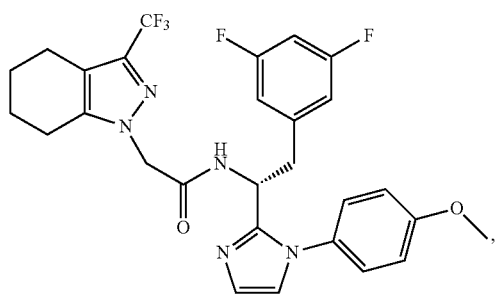

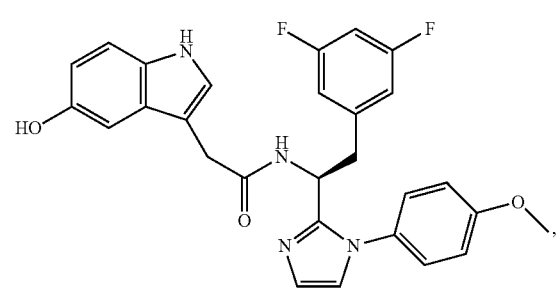

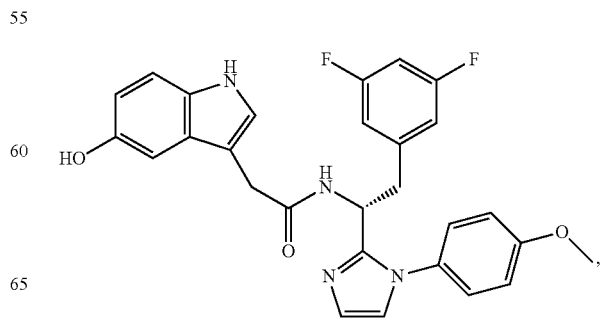

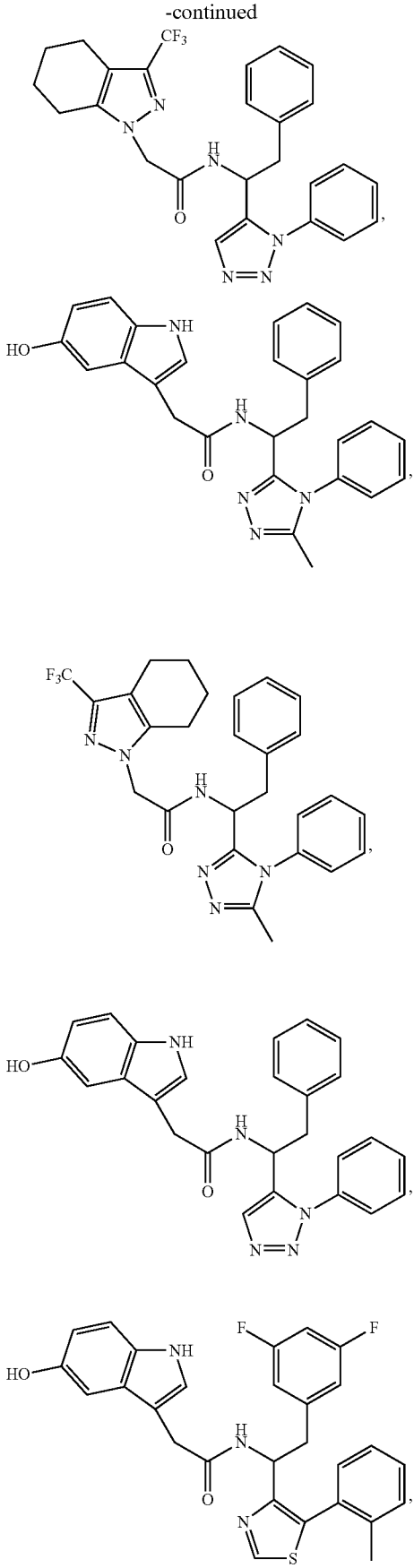

23
-continued
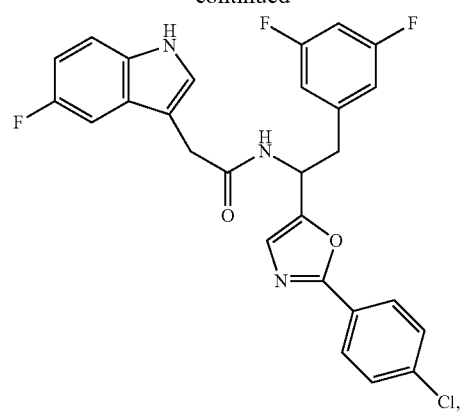
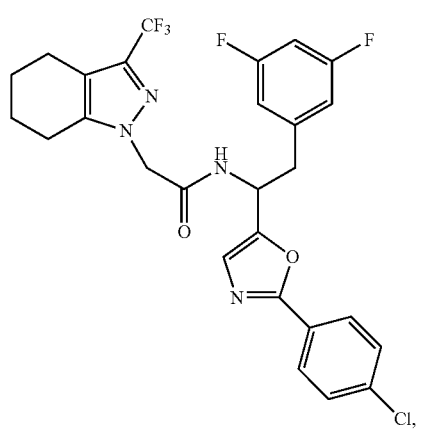
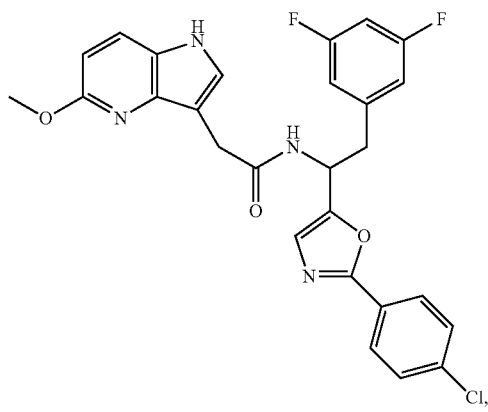
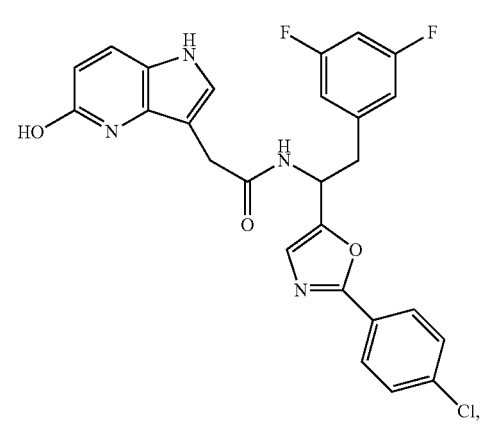
24
-continued
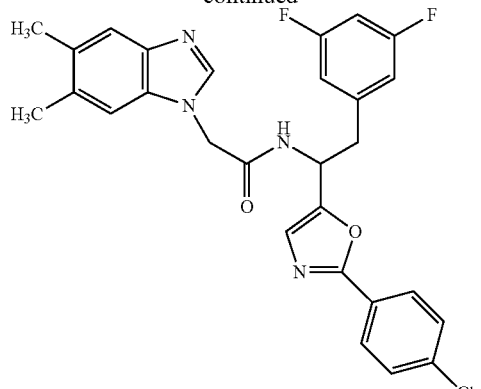
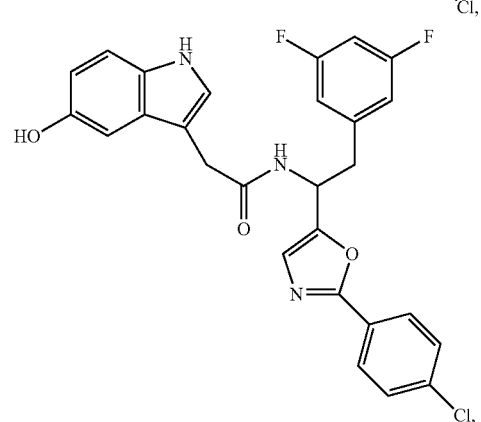
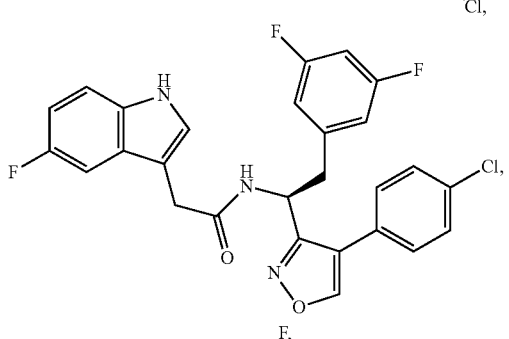
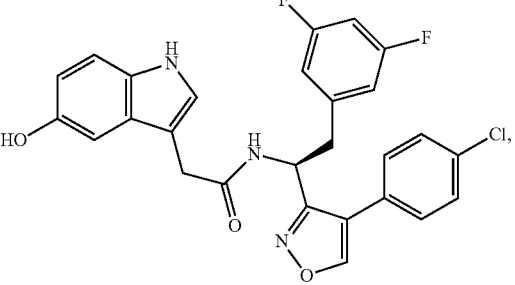
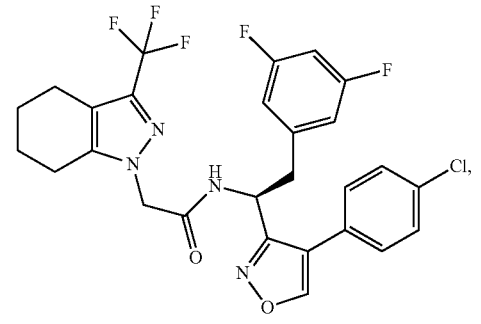

-continued
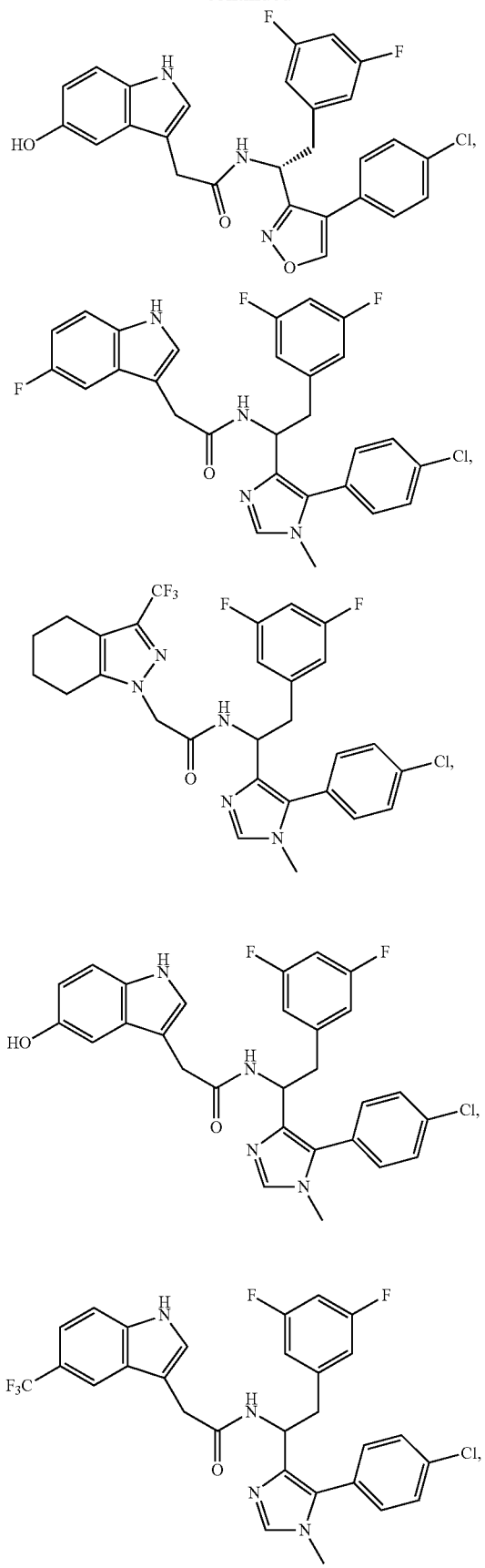
-continued
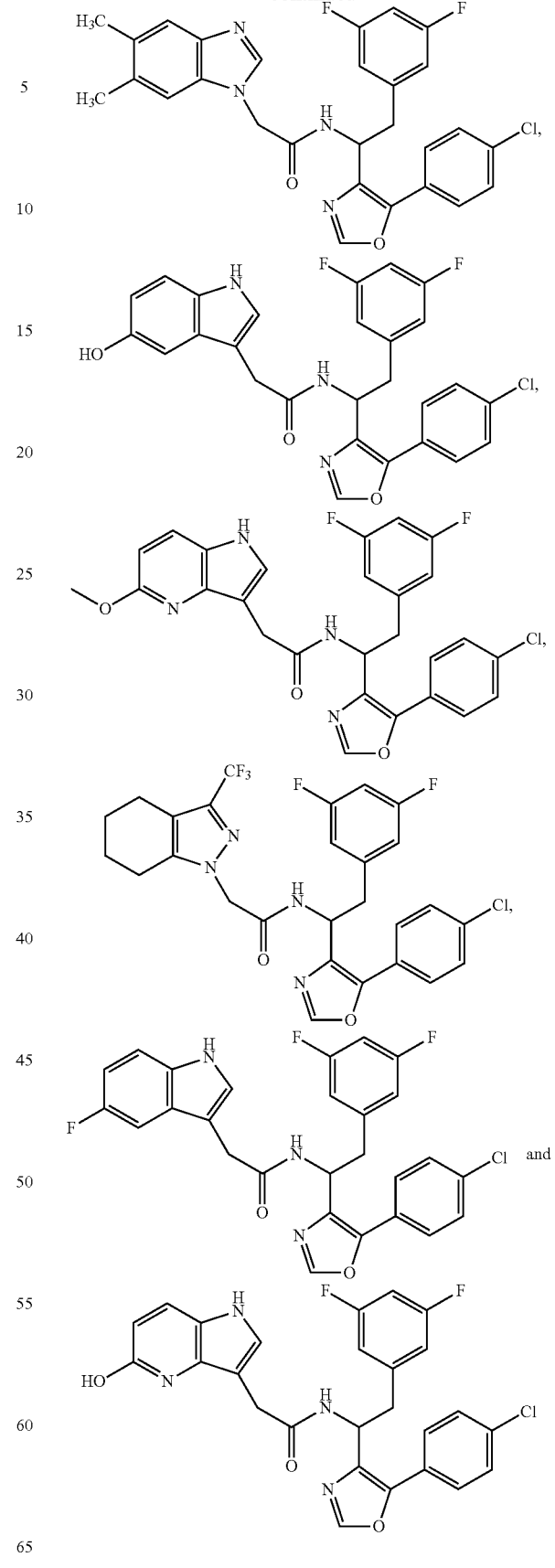
and salts thereof.

One embodiment provides a compound selected from:
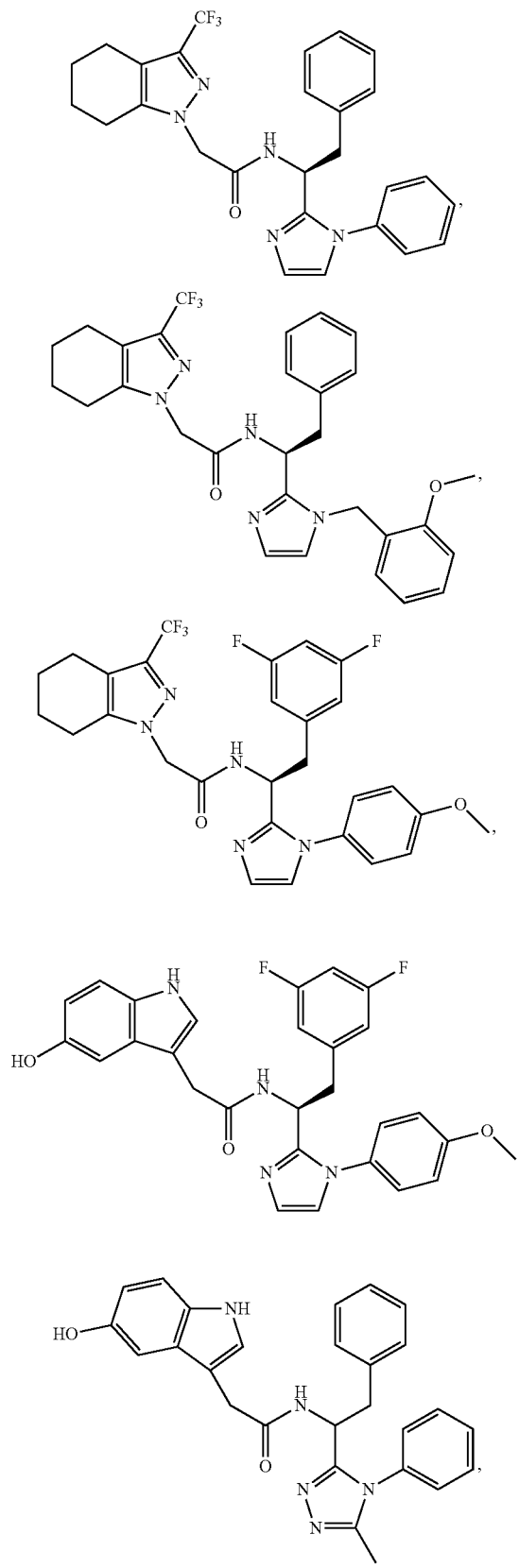
-continued
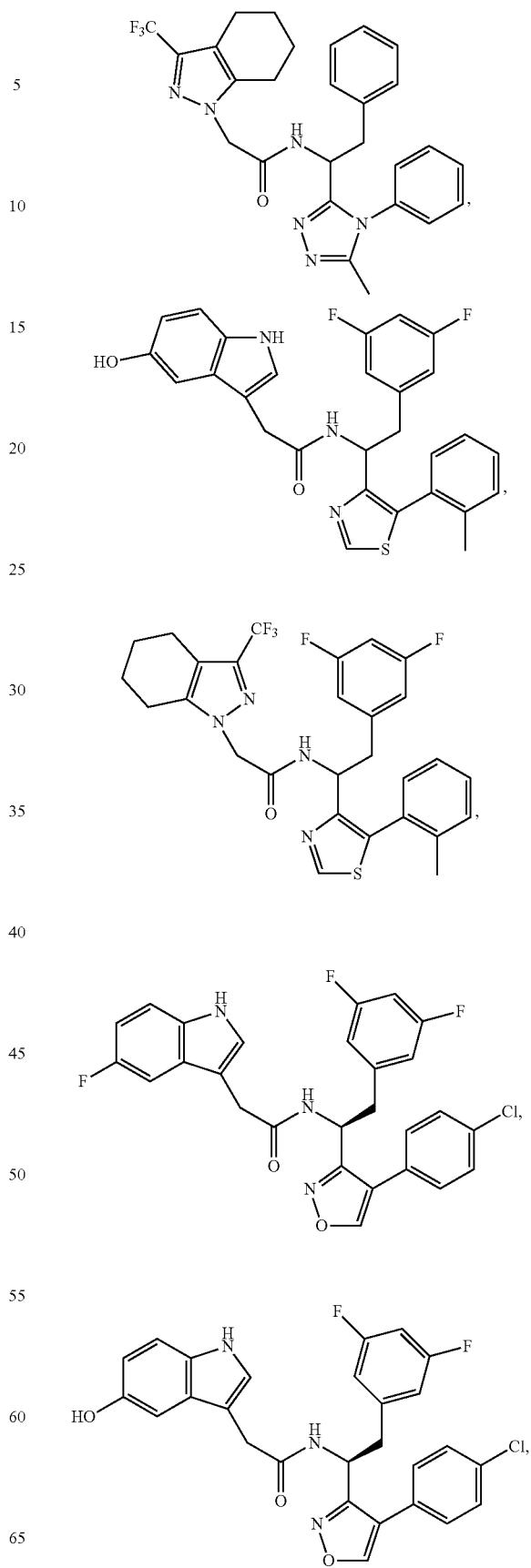

-continued

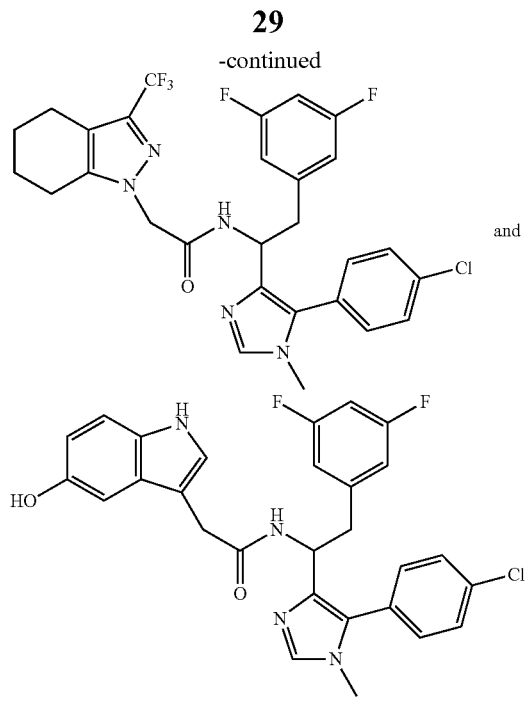

and salts thereof.

General Synthetic Procedures

Schemes 1, 2 and 3 describe methods that can be used to prepare compounds of formula I.

Scheme 1

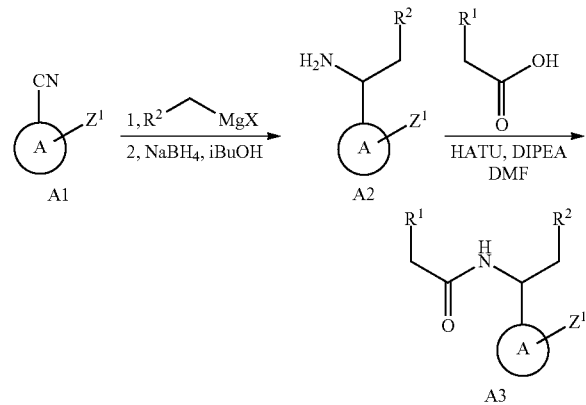

Scheme 1 describes a general synthetic route which can be used to prepare compounds of formula I. An appropriately substituted heteroaryl nitrile may be reacted with a Grignard reagent followed by reduction to provide compounds of formula A2. The amine can be coupled to a variety of carboxcyclic acid derivatives to provide compounds of formula A3.

Scheme 2

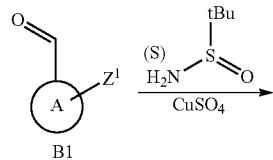

-continued

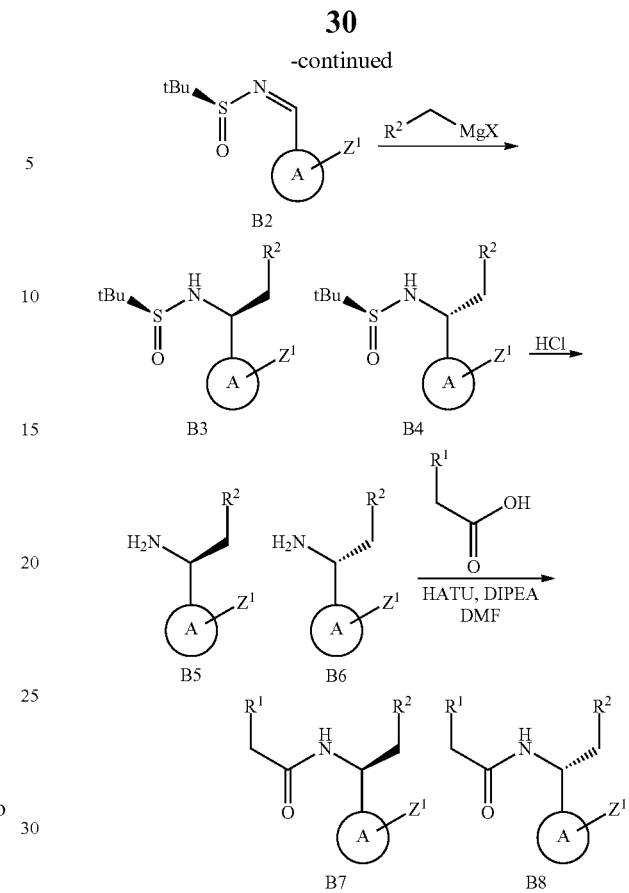

Scheme 2 describes a general stereoselective route which can be used to prepare compounds of formula I. Heteroaryl aldehydes of formula B1 can be condensed with a chiral auxiliary to provide a stereoselective addition of a nucleophilic reagent. Depicted in Scheme 2 is the condensation of an appropriately substituted heterocyclic aldehyde B1 with tert-butane sulfinamide and the addition of a Grignard reagent to provide a mixture of B3 and B4 enriched in B3. This mixture may be separated by column chromatography on silica gel to provide pure diastereomers. Removal of the auxiliary provides amines B5 and B6 which can be coupled to a variety of carboxylic acids to provide compounds of formula B7 and B8.

Scheme 3

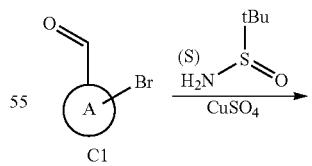

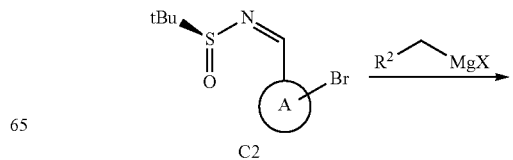

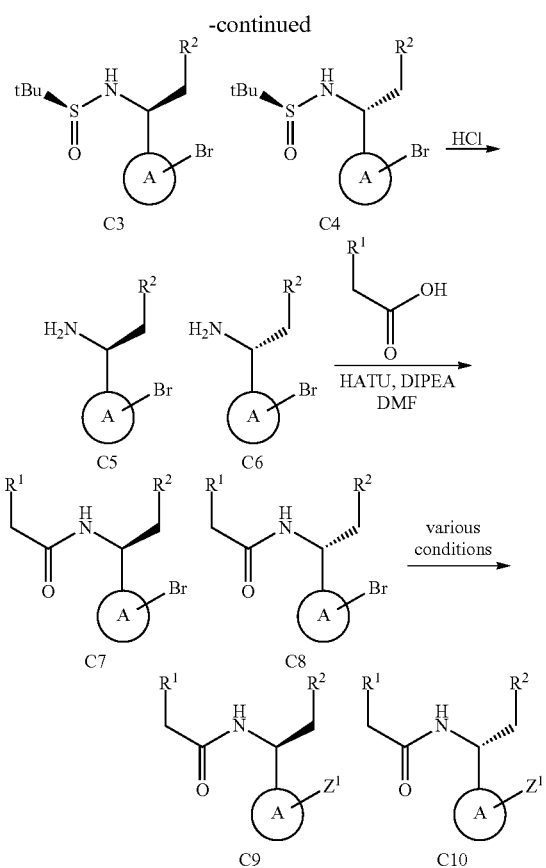

Scheme 3 describes a general stereoselective route which can be used to prepare compounds of formula I. Heteroaryl aldehydes of formula B 1 can be condensed with a chiral auxiliary to provide a stereoselective addition of a nucleophilic reagent. Depicted in Scheme 3 is the condensation of an bromo-substituted heterocyclic aldehyde C1 with (S) tert-butane sulfinamide and the addition of a Grignard reagent to provide a mixture of C3 and C4 enriched in C3. This mixture may be separated by column chromatography on silica gel to provide pure diastereomers. Removal of the auxiliary provides amines C5 and C6 which can be coupled to a variety of carboxylic acids to provide heteroaryl compounds of formula C7 and C8. Diversification of C7 and C8 may be accomplished by a variety of methods including metal catalyzed cross coupling reactions such as Suzuki couplings and Sonogashira couplings.

Combination Therapy

In one embodiment, the invention provides a method for treating an HIV infection, comprising administering to a patient in need thereof a therapeutically effective amount of a compound disclosed herein, or a pharmaceutically acceptable salt, thereof, in combination with a therapeutically effective amount of one or more additional therapeutic agents which are suitable for treating an HIV infection.

In one embodiment, a method for treating or preventing an HIV infection in a human having or at risk of having the infection is provided, comprising administering to the human a therapeutically effective amount of a compound disclosed herein, or a pharmaceutically acceptable salt thereof, in combination with a therapeutically effective amount of one or more additional therapeutic agents.

In one embodiment, the invention provides pharmaceutical compositions comprising a compound disclosed herein, or a pharmaceutically acceptable salt thereof, in combination with at least one additional therapeutic agent, and a pharmaceutically acceptable carrier. For example, the therapeutic agent used in combination with the compound disclosed herein can be any anti-HIV agent.

In one embodiment, combination pharmaceutical agents comprising a compound disclosed herein, or a pharmaceutically acceptable salt thereof, in combination with one or more additional therapeutic agents are provided.

One embodiment provides pharmaceutical compositions comprising a compound disclosed herein, or a pharmaceutically acceptable salt thereof, in combination with at least one additional therapeutic agent, and a pharmaceutically acceptable carrier. In one embodiment, the additional therapeutic agent may be an anti-HIV agent. For example, in some embodiments, the additional therapeutic agent is selected from the group consisting of HIV protease inhibiting compounds (HIV protease inhibitors), HIV non-nucleoside inhibitors of reverse transcriptase, HIV nucleoside inhibitors of reverse transcriptase, HIV nucleotide inhibitors of reverse transcriptase, HIV integrase inhibitors, HIV non-catalytic site (or allosteric) integrase inhibitors, entry inhibitors (e.g., CCR5 inhibitors, gp41 inhibitors (i.e., fusion inhibitors) and CD4 attachment inhibitors), CXCR4 inhibitors, gp120 inhibitors, G6PD and NADH-oxidase inhibitors, capsid polymerization inhibitors or capsid disrupting compounds such as those disclosed in US 2013/0165489 (University of Pennsylvania), and WO 2013/006792 (Pharma Resources), pharmacokinetic enhancers, and other drug for treating HIV, and combinations thereof.

In further embodiments, the additional therapeutic agent is selected from one or more of:

(1) HIV protease inhibitors selected from the group consisting of amprenavir, atazanavir, fosamprenavir, indinavir, lopinavir, ritonavir, nelfinavir, saquinavir, tipranavir, brecanavir, darunavir, TMC-126, TMC-114, mozenavir (DMP-450), JE-2147 (AG1776), L-756423, R00334649, KNI-272, DPC-681, DPC-684, GW640385X, DG17, PPL-100, DG35, and AG 1859;

(2) HIV non-nucleoside or non-nucleotide inhibitors of reverse transcriptase selected from the group consisting of capravirine, emivirine, delaviridine, efavirenz, nevirapine, (+) calanolide A, etravirine, GW5634, DPC-083, DPC-961, DPC-963, MW-150, TMC-120, rilpivirene, BILR 355 BS, VRX 840773, lersivirine (UK-453061), RDEA806, KMO23 and MK-1439;

(3) HIV nucleoside inhibitors of reverse transcriptase selected from the group consisting of zidovudine, emtricitabine, didanosine, stavudine, zalcitabine, lamivudine, abacavir, amdoxovir, elvucitabine, alovudine, MIV-210, ±-FTC, D-d4FC, emtricitabine, phosphazide, fozivudine tidoxil, apricitibine (AVX754), amdoxovir, KP-1461, GS-9131 (Gilead Sciences) and fosalvudine tidoxil (formerly HDP 99.0003);

(4) HIV nucleotide inhibitors of reverse transcriptase selected from the group consisting of tenofovir, tenofovir disoproxil fumarate, tenofovir alafenamide fumarate (Gilead Sciences), tenofovir alafenamide (Gilead Sciences), GS-7340 (Gilead Sciences), GS-9148 (Gilead Sciences), adefovir, adefovir dipivoxil, CMX-001 (Chimerix) or CMX-157 (Chimerix);

(5) HIV integrase inhibitors selected from the group consisting of curcumin, derivatives of curcumin, chicoric acid, derivatives of chicoric acid, 3,5-dicaffeoylquinic acid, derivatives of 3,5-dicaffeoylquinic acid, aurintricarboxylic acid, derivatives of aurintricarboxylic acid, caffeic acid phenethyl ester, derivatives of caffeic acid phenethyl ester, tyrphostin, derivatives of tyrphostin, quercetin, derivatives of quercetin, S-1360, AR-177, L-870812, and L-870810, raltegravir, BMS-538158, GSK364735C, BMS-707035, MK-2048, BA 011, elvitegravir, dolutegravir and GSK-744;

(6) HIV non-catalytic site, or allosteric, integrase inhibitors (NCINI) including, but not limited to, BI-224436, CX0516, CX05045, CX14442, compounds disclosed in WO 2009/062285 (Boehringer Ingelheim), WO 2010/130034 (Boehringer Ingelheim), WO 2013/159064 (Gilead Sciences), WO 2012/145728 (Gilead Sciences), WO 2012/003497 (Gilead Sciences), WO 2012/003498 (Gilead Sciences) each of which is incorporated by reference in its entirety herein;

(7) gp41 inhibitors selected from the group consisting of enfuvirtide, sifuvirtide, albuvirtide, FB006M, and TR1-1144;

(8) the CXCR4 inhibitor AMD-070;

(9) the entry inhibitor SP01A;

(10) the gp120 inhibitor BMS-488043;

(11) the G6PD and NADH-oxidase inhibitor immunitin;

(12) CCR5 inhibitors selected from the group consisting of aplaviroc, vicriviroc, maraviroc, cenicriviroc, PRO-140, INCB15050, PF-232798 (Pfizer), and CCR5 mAb004;

(13) CD4 attachment inhibitors selected from the group consisting of ibalizumab (TMB-355) and BMS-068 (BMS-663068);

(14) pharmacokinetic enhancers selected from the group consisting of cobicistat and SPI-452; and

(15) other drugs for treating HIV selected from the group consisting of BAS-100, SPI-452, REP 9, SP-01A, TNX-355, DES6, ODN-93, ODN-112, VGV-1, PA-457 (bevirimat), HRG214, VGX-410, KD-247, AMZ 0026, CYT 99007A-221 HIV, DEBIO-025, BAY 50-4798, MDX010 (ipilimumab), PBS 119, ALG 889, and PA-1050040 (PA-040).

In certain embodiments, a compound disclosed herein, or a pharmaceutically acceptable salt thereof, is combined with two, three, four or more additional therapeutic agents. In certain embodiments, a compound disclosed herein, or a pharmaceutically acceptable salt thereof, is combined with two additional therapeutic agents. In other embodiments, a compound disclosed herein, or a pharmaceutically acceptable salt thereof, is combined with three additional therapeutic agents. In further embodiments, a compound disclosed herein, or a pharmaceutically acceptable salt thereof, is combined with four additional therapeutic agents. The two, three four or more additional therapeutic agents can be different therapeutic agents selected from the same class of therapeutic agents, or they can be selected from different classes of therapeutic agents. In a specific embodiment, a compound disclosed herein, or a pharmaceutically acceptable salt thereof, is combined with an HIV nucleotide inhibitor of reverse transcriptase and an HIV non-nucleoside inhibitor of reverse transcriptase. In another specific embodiment, a compound disclosed herein, or a pharmaceutically acceptable salt thereof, is combined with an HIV nucleotide inhibitor of reverse transcriptase, and an HIV protease inhibiting compound. In a further embodiment, a compound disclosed herein, or a pharmaceutically acceptable salt thereof, is combined with an HIV nucleotide inhibitor of reverse transcriptase, an HIV non-nucleoside inhibitor of reverse transcriptase, and an HIV protease inhibiting compound. In an additional embodiment, a compound disclosed herein, or a pharmaceutically acceptable salt thereof, is combined with an HIV nucleotide inhibitor of reverse transcriptase, an HIV non-nucleoside inhibitor of reverse transcriptase, and a pharmacokinetic enhancer.

In some embodiments, one or more of the compounds disclosed herein are combined with one or more other active therapeutic agents in a unitary dosage form for simultaneous or sequential administration to a patient. The combination therapy may be administered as a simultaneous or sequential regimen. When administered sequentially, the combination may be administered in two or more administrations.

In some embodiments, one or more of the compounds disclosed herein are co-administered with one or more other active therapeutic agents. Co-administration of a compound disclosed herein with one or more other active therapeutic agents generally refers to simultaneous or sequential administration of a compound disclosed herein and one or more other active therapeutic agents, such that therapeutically effective amounts of disclosed herein and one or more other active therapeutic agents are both present in the body of the patient.

In yet another embodiment, the present application provides a method for treating an HIV infection comprising administering to a patient in need thereof a therapeutically effective amount of a compound disclosed herein, or a pharmaceutically acceptable salt thereof, in combination with a therapeutically effective amount of one or more additional therapeutic agents such as those disclosed above.

Pharmaceutical Formulations

The compounds disclosed herein are formulated with conventional carriers (e.g., inactive ingredient or excipient material) which will be selected in accord with ordinary practice. Tablets will contain excipients including glidants, fillers, binders and the like. Aqueous formulations are prepared in sterile form, and when intended for delivery by other than oral administration generally will be isotonic. All formulations will optionally contain excipients such as those set forth in the *Handbook of Pharmaceutical Excipients* (1986). Excipients include ascorbic acid and other antioxidants, chelating agents such as EDTA, carbohydrates such as dextrin, hydroxyalkylcellulose, hydroxyalkylmethylcellulose, stearic acid and the like. One embodiment provides the formulation as a solid dosage form including a solid oral dosage form. The pH of the formulations ranges from about 3 to about 11, but is ordinarily about 7 to 10.

While it is possible for the active ingredients to be administered alone it may be preferable to present them as pharmaceutical formulations (compositions). The formulations, both for veterinary and for human use, of the invention comprise at least one active ingredient, as above defined, together with one or more acceptable carriers and optionally other therapeutic ingredients. The carrier(s) must be "acceptable" in the sense of being compatible with the other ingredients of the formulation and physiologically innocuous to the recipient thereof.

The formulations include those suitable for the foregoing administration routes. The formulations may conveniently be presented in unit dosage form and may be prepared by any of the methods well known in the art of pharmacy. Techniques and formulations generally are found in *Remington's Pharmaceutical Sciences* (Mack Publishing Co., Easton, Pa.). Such methods include the step of bringing into association the active ingredient with inactive ingredients (e.g., a carrier, pharmaceutical excipients, etc.) which constitutes one or more accessory ingredients. In general the formulations are prepared by uniformly and intimately bringing into association the active ingredient with liquid carriers or finely divided solid carriers or both, and then, if necessary, shaping the product.

Formulations of the present invention suitable for oral administration may be presented as discrete units including but not limited to capsules, cachets or tablets each containing a predetermined amount of the active ingredient.

Pharmaceutical formulations according to the present invention comprise one or more compounds disclosed herein together with one or more pharmaceutically acceptable carriers or excipients and optionally other therapeutic agents. Pharmaceutical formulations containing the active ingredient may be in any form suitable for the intended method of administration. When used for oral use for example, tablets, troches, lozenges, aqueous or oil suspensions, dispersible powders or granules, emulsions, hard or soft capsules, syrups or elixirs may be prepared. Compositions intended for oral use may be prepared according to any method known to the art for the manufacture of pharmaceutical compositions and such compositions may contain one or more agents including sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. These excipients may be, for example, inert diluents, such as calcium or sodium carbonate, lactose, lactose monohydrate, croscarmellose sodium, povidone, calcium or sodium phosphate; granulating and disintegrating agents, such as maize starch, or alginic acid; binding agents, such as cellulose, microcrystalline cellulose, starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

The amount of active ingredient that is combined with the inactive ingredients to produce a dosage form will vary depending upon the host treated and the particular mode of administration. For example, in some embodiments, a dosage form for oral administration to humans contains approximately 1 to 1000 mg of active material formulated with an appropriate and convenient amount of carrier material (e.g., inactive ingredient or excipient material). In certain embodiments, the carrier material varies from about 5 to about 95% of the total compositions (weight:weight).

It should be understood that in addition to the ingredients particularly mentioned above the formulations of this invention may include other agents conventional in the art having regard to the type of formulation in question, for example those suitable for oral administration may include flavoring agents.

The invention further provides veterinary compositions comprising at least one active ingredient as above defined together with a veterinary carrier.

Veterinary carriers are materials useful for the purpose of administering the composition and may be solid, liquid or gaseous materials which are otherwise inert or acceptable in the veterinary art and are compatible with the active ingredient. These veterinary compositions may be administered orally, parenterally or by any other desired route.

Effective dose of active ingredient depends at least on the nature of the condition being treated, toxicity, whether the compound is being used prophylactically (lower doses), the method of delivery, and the pharmaceutical formulation, and will be determined by the clinician using conventional dose escalation studies.

Routes of Administration

One or more compounds disclosed herein (herein referred to as the active ingredients) are administered by any route appropriate to the condition to be treated. Suitable routes include oral, rectal, nasal, topical (including buccal and sublingual), vaginal and parenteral (including subcutaneous, intramuscular, intravenous, intradermal, intrathecal and epidural), and the like. It will be appreciated that the preferred route may vary with for example the condition of the recipient. An advantage of the compounds disclosed herein is that they are orally bioavailable and can be dosed orally.

The antiviral properties of a compound disclosed herein may be determined using Test A described below.

Test A: Antiviral Assay in MT4 Cells

For the antiviral assay, 40 µL of 1× test concentration of 3-fold serially diluted compound in culture medium with 10% FBS was added to each well of a 384-well plate (10 concentrations) in quadruplicate. MT-4 cells were next mixed with HIV-IIIb at an m.o.i of 0.003 for 1 hour, after which time 35 µL of virus/cell mixture (2000 cells) was immediately added to each well containing 40 µL of diluted compound. The plates were then incubated at 37° C. for 5 days. After 5 days of incubation, 25 µl of 2× concentrated CellTiter-Glo™ Reagent (catalog #G7571, Promega Biosciences, Inc., Madison, Wis.) was added to each well containing MT-4 cells. Cell lysis was carried out by incubating at room temperature for 10 min and then chemiluminescence was read. EC50 values were defined as the compound concentration that caused a 50% decrease in luminescence signal, a measure of HIV-1 replication. Percent inhibition of virus-induced cell killing calculated from the dose response curve at 4 µM drug concentration is shown in the table below.

Test B: Cytotoxicity Assay

Compound cytotoxicity and the corresponding CC50 values was determined using the same protocol as described in the antiviral assay (Test A) except that uninfected cells were used.

Compounds disclosed herein demonstrate antiviral activity (Test A) as depicted in the table below. Accordingly, the compounds disclosed herein may be useful for treating an HIV virus infection, treating AIDS or for delaying the onset of AIDS or ARC symptoms. Shown below are the corresponding values for CC50 and percent inhibition of virus-induced cell killing in the presence of 6 µM drug concentration.

| Compound | % inhibition at 6 µM | CC50 (nM) |
|---|---|---|
| 1E | 83 | 21864 |
| 2 | 6 | 27782 |
| 3C | 19 | 37057 |
| 4 | 64 | 11373 |
| 5F | 79 | 13456 |
| 6B | 4 | 11952 |
| 7 | 121 | >47114 |
| 8 | 6 | 44341 |
| 9E | 0 | 13198 |
| 10G | 51 | >53192 |
| 11 | 76 | >53000 |
| 12 | 4 | >53000 |
| 13E | 93 | 25405 |
| 14 | 60 | 11306 |
| 15C | 0 | 34996 |
| 16 | 0 | 51909 |
| 17B | 0 | >53000 |
| 18B | 4 | >53000 |
| 19F | 0 | 9141 |
| 20 | 1 | 12233 |
| 21 | 2 | 25394 |
| 22 | 1 | 50712 |
| 23 | 0 | 12045 |
| 24 | 5 | 13637 |
| 25I | 68 | 9894 |
| 26 | 106 | 19525 |
| 27 | 28 | 6166 |
| 28B | 3 | 11629 |

-continued

| Compound | % inhibition at 6 μM | CC50 (nM) |
|---|---|---|
| 29G | 44 | 10776 |
| 30 | 69 | 11014 |
| 31 | 75 | 25410 |
| 32 | 0 | 11872 |
| 33H | 3 | 31802 |
| 34 | 0 | 22136 |
| 35 | 0 | 15311 |
| 36 | 0 | 16283 |
| 37 | 0 | 10214 |
| 38 | 0 | 19143 |

In one embodiment, the compounds demonstrate >10% inhibition at 6 μM. In one embodiment, the compounds demonstrate >30% inhibition at 6 μM. In one embodiment, the compounds demonstrate >50% inhibition at 6 μM. In one embodiment, the compounds demonstrate >70% inhibition at 6 μM. It is to be understood that the compounds disclosed herein can be grouped according to their % inhibition as described above.

The specific pharmacological responses observed may vary according to and depending on the particular active compound selected or whether there are present pharmaceutical carriers, as well as the type of formulation and mode of administration employed, and such expected variations or differences in the results are contemplated in accordance with practice of the present invention.

The Examples provided herein describe the synthesis of compounds disclosed herein as well as intermediates used to prepare the compounds. It is to be understood that individual steps described herein may be combined. It is also to be understood that separate batches of a compound may be combined and then carried forth in the next synthetic step.

EXAMPLE 1

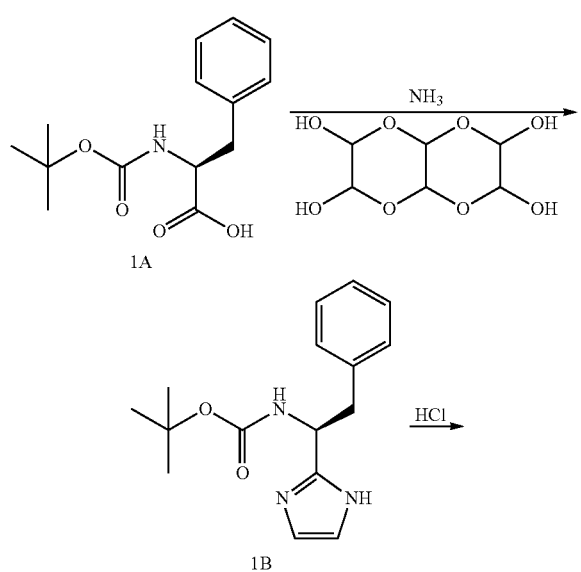

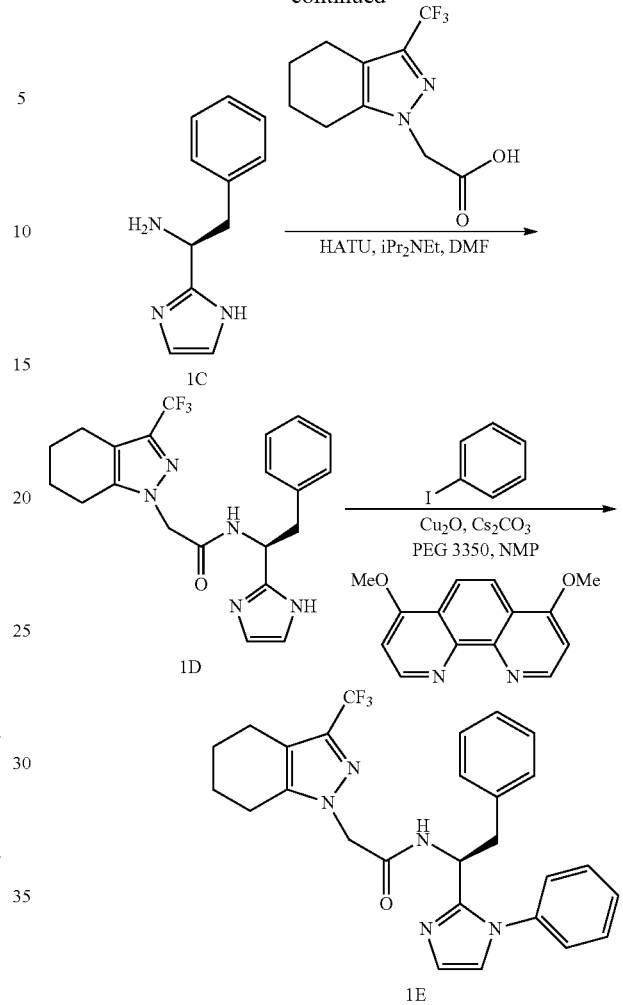

Synthesis of (S)-tert-butyl 1-(1H-imidazol-2-yl)-2-phenylethylcarbamate (1B)

To (S)-2-(tert-butoxycarbonylamino)-3-phenylpropanoic acid (2 g, 8.02 mmol) and glyoxal trimeric dehydrate (880 mg, 4.19 mmol) in MeOH (12 mL) was added 2N $NH_3$ in MeOH (18.3 mL). The reaction was stirred at ambient temperature for 15 hr. Solvents were evaporated in vacuo and the residue partitioned between EtOAc and aqueous saturated NaCl. The organics were separated, dried, and removed in vacuo to provide the title compound: MS (m/z) 288.1 $[M+H]^+$.

Synthesis of (S)-1-(1H-imidazol-2-yl)-2-phenylethanamine (1C)

(S)-tert-Butyl 1-(1H-imidazol-2-yl)-2-phenylethylcarbamate (355 mg, 1.18 mmol) was dissolved in DCM (5 mL) and treated with 4N HCl in dioxanes (12 mL). After 3 hr, solvents were removed in vacuo and the crude product was used directly in the next reaction.

Synthesis of (S)-N-(1-(1H-imidazol-2-yl)-2-phenylethyl)-2-(3-(trifluoromethyl)-4,5,6,7-tetrahydro-1H-indazol-1-yl)acetamide (1D)

To (S)-1-(1H-imidazol-2-yl)-2-phenylethanamine from the previous reaction was added DMF (10 mL), 2-(3-(trifluoromethyl)-4,5,6,7-tetrahydro-1H-indazol-1-yl)acetic acid (288 mg, 1.18 mmol), and HATU (530 mg, 1.4 mmol). Diisopropylethylamine (452 μL, 2.6 mmol) was added and the reaction was stirred for 15 min. The reaction was partitioned between EtOAc and H₂O. The organics were separated, washed with saturated aqueous NaHCO₃, and saturated aqueous NaCl. Solvents were removed in vacuo and the residue purified by column chromatography on silica to provide the desired product: MS (m/z) 418.3 [M+H]⁺.

Synthesis of (S)-N-(2-phenyl-1-(1-phenyl-1H-imidazol-2-yl)ethyl)-2-(3-(trifluoromethyl)-4,5,6,7-tetrahydro-1H-indazol-1-yl)acetamide (1E)

To (S)-N-(1-(1H-imidazol-2-yl)-2-phenylethyl)-2-(3-(trifluoromethyl)-4,5,6,7-tetrahydro-1H-indazol-1-yl)acetamide (111 mg, 0.27 mmol) in NMP (0.6 mL) was added iodobenzene (27 µL, 0.24 mmol), Cu₂O (1 mg), PEG 3500 (50 mg), 4,7-dimethoxy-1,10-phenanthroline (6 mg) and Cs₂CO₃ (110 mg, 0.34 mmol). The reaction was heated to 115° C. for 4 hr. After cooling to ambient temperature, the reaction mixture was filtered over a heavy metal scavenging column and eluted with DCM. The solvents were removed in vacuo and the residue purified by RP HPLC to provide the title compound: ¹H NMR (400 MHz, DMSO-d₆) δ 9.16 (s), 7.55 (s, 1H), 7.42 (t, 1H), 7.14 (q, 2H), 7.01 (d, 1H), 6.84 (dd, 1H), 4.77-4.71 (m, 1H), 3.08 (d, 1H), 2.36 (s, 1H), 1.62 (d, 2H). MS (m/z) 494.3 [M+H]⁺.

EXAMPLE 2

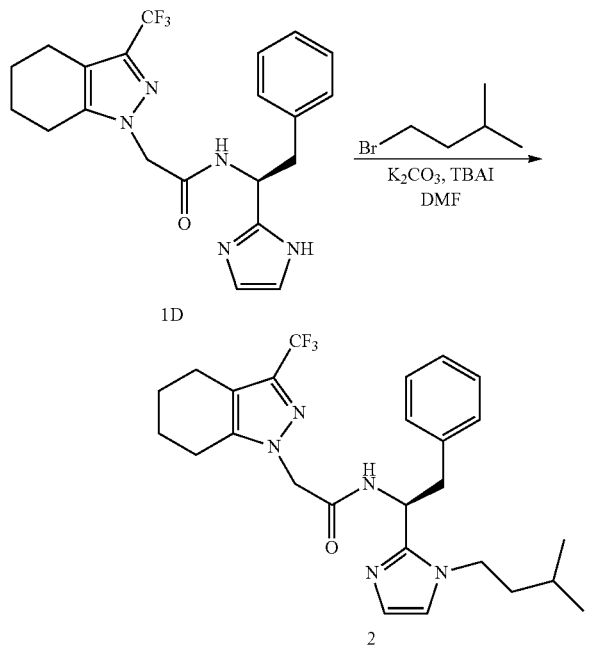

Synthesis of (S)-N-(1-(1-isopentyl-1H-imidazol-2-yl)-2-phenylethyl)-2-(3-(trifluoromethyl)-4,5,6,7-tetrahydro-1H-indazol-1-yl)acetamide (2)

(S)-N-(1-(1H-imidazol-2-yl)-2-phenylethyl)-2-(3-(trifluoromethyl)-4,5,6,7-tetrahydro-1H-indazol-1-yl)acetamide (42 mg, 0.1 mmol) and 1-bromo-3-methylbutane (24 µL, 0.2 mmol) were combined in DMF (0.6 mL) and treated with K₂CO₃ (21 mg, 0.15 mmol) and TBAI (4 mg). The reaction was heated to 90° C. and stirred for 15 h. The reaction was purified by RP HPLC to provide the title compound: ¹H NMR (400 MHz, DMSO-d₆) δ 7.23 (q, 7.5 Hz, 3H), 7.16-7.09 (m, 2H), 5.24 (m, 1H), 4.75 (s, 2H), 3.83 (m, 3H), 3.22 (d, 1H), 2.35 (m, 2H), 1.63 (m, 5H), 1.40 (m, 2H), 0.77 (t, 6H). MS (m/z) 488.5 [M+H]⁺.

EXAMPLE 3

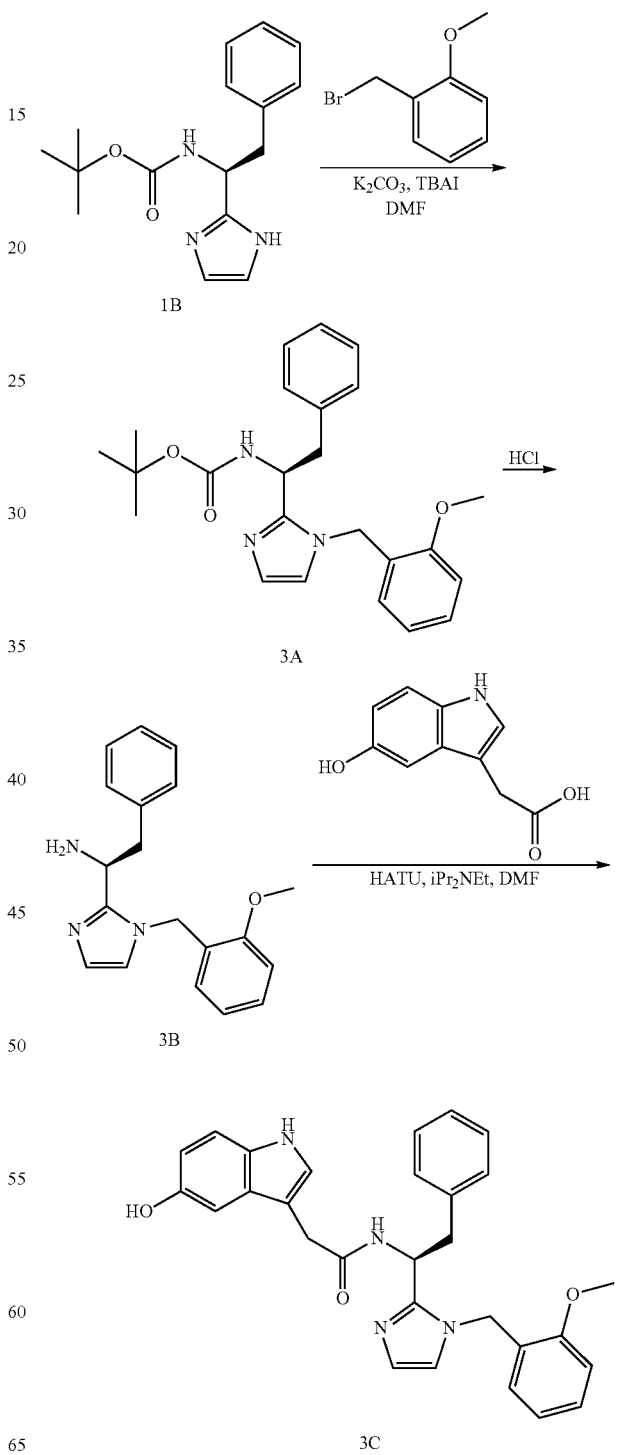

Synthesis of (S)-tert-butyl 1-(1-(2-methoxybenzyl)-1H-imidazol-2-yl)-2-phenylethylcarbamate (3A)

To (S)-tert-butyl 1-(1H-imidazol-2-yl)-2-phenylethylcarbamate (120 mg, 0.42 mmol) in DMF (1 mL) was added 1-(bromomethyl)-2-methoxybenzene (58 μL, 0.42 mmol), K$_2$CO$_3$ (70 mg, 0.5 mmol) and TBAI (5 mg) and heated to 90° C. After stirring for 1 hr and cooling to ambient temperature, the reaction was partitioned between EtOAc and H$_2$O. The organics were separated, washed with saturated aqueous NaHCO$_3$, and saturated aqueous NaCl. Solvents were removed in vacuo and the residue purified by column chromatography on silica to provide the desired product: MS (m/z) 408.2 [M+H]$^+$.

Synthesis of (S)-1-(1-(2-methoxybenzyl)-1H-imidazol-2-yl)-2-phenylethanamine (3B)

(S)-tert-butyl 1-(1-(2-methoxybenzyl)-1H-imidazol-2-yl)-2-phenylethylcarbamate was dissolved in DCM and treated with 4 N HCl in dioxanes. The reaction was stirred for 3 hr. Solvents were removed in vacuo to provide the desired product. MS (m/z) 308.1 [M+H]$^+$.

Synthesis of (S)-2-(5-hydroxy-1H-indol-3-yl)-N-(1-(1-(2-methoxybenzyl)-1H-imidazol-2-yl)-2-phenylethyl)acetamide (3C)

(S)-1-(1-(2-methoxybenzyl)-1H-imidazol-2-yl)-2-phenylethanamine (75 mg, 0.2 mmol), 2-(5-hydroxy-1H-indol-3-yl)acetic acid (47 mg, 0.25 mmol) and HATU (97 mg, 0.26 mmol) were combined in DMF (2 mL) and treated with diisopropylethylamine (70 μL). The reaction was stirred for 30 min and the purified by RP HPLC to provide the title compound: $^1$H NMR (400 MHz, DMSO-d$_6$) δ 10.53 (d, 1H), 8.67 (d, 1H), 7.58 (s, 1H), 7.38-7.28 (m, 2H), 7.20-7.12 (m, 3H), 7.12-6.98 (m, 4H), 6.91-6.79 (m, 3H), 6.72 (d, 1H), 6.57 (dd, 1H), 5.38-5.31 (m, 1H), 5.17 (d, 2H), 3.71 (s, 3H), 3.40-3.22 (m, 3H), 3.16 (dd, 1H). MS (m/z) 481.2 [M+H]$^+$.

EXAMPLE 4

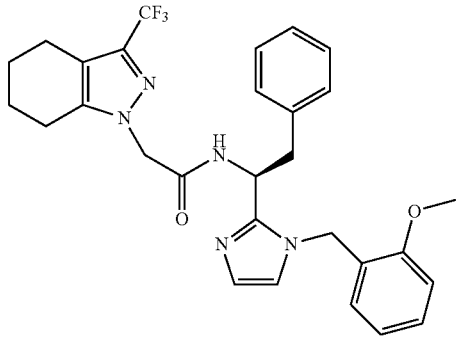

4

Synthesis of (S)-2-(5-hydroxy-1H-indol-3-yl)-N-(1-(1-(2-methoxybenzyl)-1H-imidazol-2-yl)-2-phenylethyl)acetamide (4)

The title compound was prepared according to the method presented in the synthesis of Example 3 utilizing 3B and 2-(3-(trifluoromethyl)-4,5,6,7-tetrahydro-1H-indazol-1-yl)acetic acid. $^1$H NMR (400 MHz, DMSO-d$_6$) δ 9.07 (s, 1H), 7.33 (t, 2H), 7.21 (d, 4H), 7.11 (d, 3H), 7.02 (d, 1H), 6.87 (t, 2H), 5.40 (s, 1H), 5.16 (s, 2H), 4.62 (q, 3H), 3.72 (s, 3H), 3.29-3.19 (m, 3H), 2.18 (d, 1H), 1.62 (t, 4H). MS (m/z) 538.5 [M+H]$^+$.

EXAMPLE 5

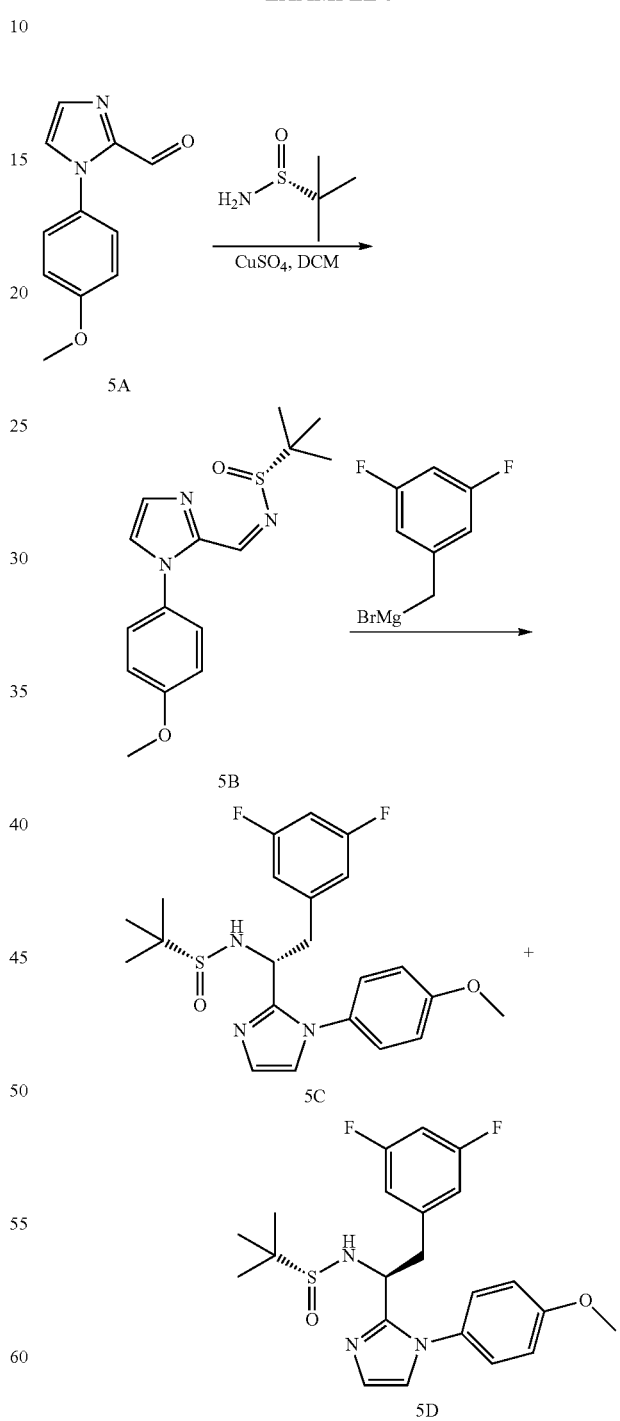

43

-continued

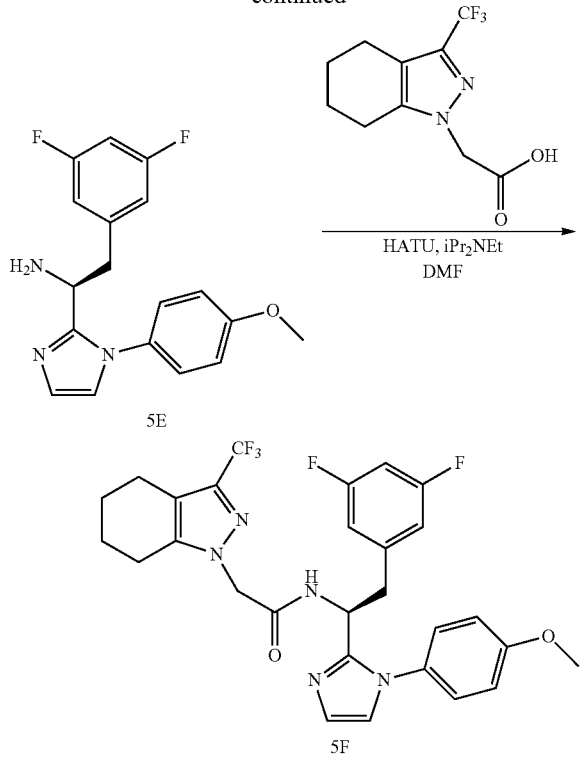

Synthesis of (R)-N-((1-(4-methoxyphenyl)-1H-imidazol-2-yl)methylene)-2-methylpropane-2-sulfinamide (5B)

1-(4-methoxyphenyl)-1H-imidazole-2-carbaldehyde (200 mg, 1 mmol), (R)-2-methylpropane-2-sulfinamide (145 mg, 1.2 mmol), and $CuSO_4$ (160 mg, 1 mmol) were combined in DCM (5 mL). The reaction was stirred at ambient temperature for 15 hr. The reaction was filtered, solvents removed in vacuo, and the residue purified by column chromatography on silica to provide the desired product: MS (m/z) 305.9 $[M+H]^+$.

Synthesis of (R)-N-((R)-2-(3,5-difluorophenyl)-1-(1-(4-methoxyphenyl)-1H-imidazol-2-yl)ethyl)-2-methylpropane-2-sulfinamide and (R)-N-((S)-2-(3,5-difluorophenyl)-1-(1-(4-methoxyphenyl)-1H-imidazol-2-yl)ethyl)-2-methylpropane-2-sulfinamide (5C and 5D)

(R)-N-((1-(4-methoxyphenyl)-1H-imidazol-2-yl)methylene)-2-methylpropane-2-sulfinamide (130 mg, 0.43 mmol) was dissolved in THF (2 mL) and cooled to −78° C. (3,5-difluorobenzyl)magnesium bromide (2 mL of a 0.25 solution in diethylether) was added dropwise. The reaction was stirred at −78° C. for 2 hr then let warm to −40° C. and quenched with $H_2O$. The reaction solution was extracted with EtOAc. The organics were separated, washed with saturated aqueous $NaHCO_3$, and dried with saturated aqueous NaCl. Solvents were removed in vacuo and the residue purified by column chromatography on silica to provide 5C(Rf=0.3 EtOAc, MS (m/z) 434.1 $[M+H]^+$) and 5D (Rf=0.2 EtOAc, MS (m/z) 434.1 $[M+H]^+$).

44

Synthesis of (S)-2-(3,5-difluorophenyl)-1-(1-(4-methoxyphenyl)-1H-imidazol-2-yl)ethanamine (5E)

(R)-N-(S)-2-(3,5-difluorophenyl)-1-(1-(4-methoxyphenyl)-1H-imidazol-2-yl)ethyl)-2-methylpropane-2-sulfinamide (40 mg, 0.09 mmol) was dissolved in DCM (0.7 mL) and treated with 4N HCl in dioxanes (0.7 mL). The reaction was stirred for 3 hr. Solvents were removed in vacuo and the crude product was used directly in the next step. MS (m/z) 330.1 $[M+H]^+$.

Synthesis of (S)-N-(2-(3,5-difluorophenyl)-1-(1-(4-methoxyphenyl)-1H-imidazol-2-yl)ethyl)-2-(3-(trifluoromethyl)-4,5,6,7-tetrahydro-1H-indazol-1-yl)acetamide (5F)

The title compound as prepared according to the method presented in the synthesis of Example 1 utilizing 5E. $^1$H NMR (400 MHz, DMSO-$d_6$) δ 9.03 (s, 1H), 7.10 (d, 2H), 6.99 (t, 3H), 6.63 (d, 2H), 5.01 (d, 1H), 4.68 (s, 2H), 3.76 (s, 3H), 3.11 (d, 2H), 2.34 (s, 1H), 1.63 (s, 4H); MS (m/z) 560.4 $[M+H]^+$.

EXAMPLE 6

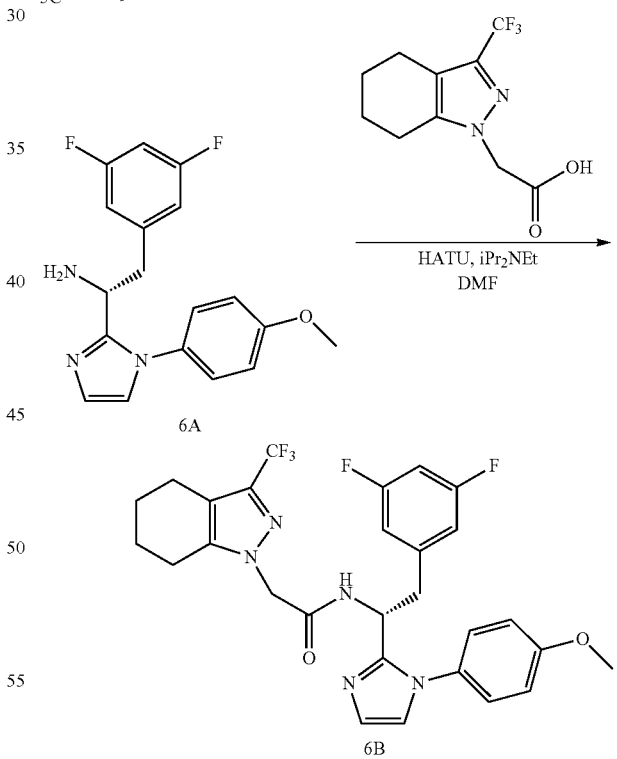

Synthesis of (R)-2-(3,5-difluorophenyl)-1-(1-(4-methoxyphenyl)-1H-imidazol-2-yl)ethanamine (6A)

The title compound as prepared according to the method presented in the synthesis of Example 5 utilizing 5C. MS (m/z) 330.1 $[M+H]^+$.

Synthesis of (R)-N-(2-(3,5-difluorophenyl)-1-(1-(4-methoxyphenyl)-1H-imidazol-2-yl)ethyl)-2-(3-(trifluoromethyl)-4,5,6,7-tetrahydro-1H-indazol-1-yl)acetamide (6B)

The title compound as prepared according to the method presented in the synthesis of Example 1 utilizing 6A. $^1$H NMR (400 MHz, DMSO-$d_6$) δ 9.08 (s, 1H), 7.53 (s, 1H), 7.16-7.08 (m, 2H), 7.08-6.95 (m, 3H), 6.64 (d, 2H), 5.03 (q, 1H), 4.77-4.62 (m, 2H), 3.76 (s, 3H), 3.12 (d, 2H), 2.47-2.24 (m, 2H), 1.63 (dq, 4H); MS (m/z) 560.4 [M+H]$^+$.

EXAMPLE 7

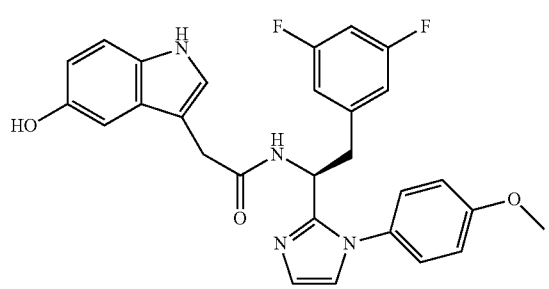

7

Synthesis of (S)-N-(2-(3,5-difluorophenyl)-1-(1-(4-methoxyphenyl)-1H-imidazol-2-yl)ethyl)-2-(5-hydroxy-1H-indol-3-yl)acetamide (7)

The title compound as prepared according to the method presented in the synthesis of Example 5 utilizing 5E and 2-(5-hydroxy-1H-indol-3-yl)acetic acid. $^1$H NMR (400 MHz, DMSO-$d_6$) δ 10.53 (s, 1H), 8.69 (s, 1H), 7.09 (d, 1H), 7.03-6.95 (m, 3H), 6.89 (d, 2H), 6.77 (d, 1H), 6.61-6.52 (m, 3H), 4.91 (s, 1H), 3.73 (s, 3H), 3.40 (s, 2H); MS (m/z) 503.4 [M+H]$^+$.

EXAMPLE 8

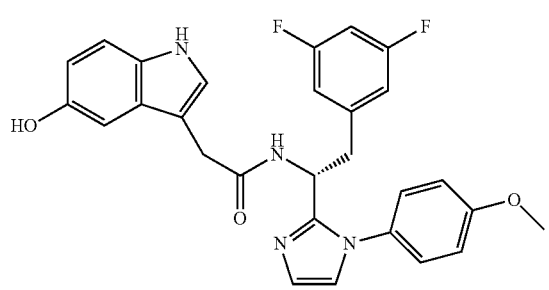

8

Synthesis of (R)-N-(2-(3,5-difluorophenyl)-1-(1-(4-methoxyphenyl)-1H-imidazol-2-yl)ethyl)-2-(5-hydroxy-1H-indol-3-yl)acetamide (8)

The title compound as prepared according to the method presented in the synthesis of Example 6 utilizing 6A and 2-(5-hydroxy-1H-indol-3-yl)acetic acid. $^1$H NMR (400 MHz, DMSO-$d_6$) δ 10.53 (s, 1H), 8.70 (s, 1H), 8.52 (s, 1H), 7.54 (s, 1H), 7.13-6.95 (m, 5H), 6.90 (d, 2H), 6.77 (d, 1H), 6.61-6.53 (m, 3H), 4.91 (q, 1H), 3.74 (s, 3H), 3.51-3.34 (m, 2H), 3.18-3.01 (m, 2H); MS (m/z) 503.4 [M+H]$^+$.

EXAMPLE 9

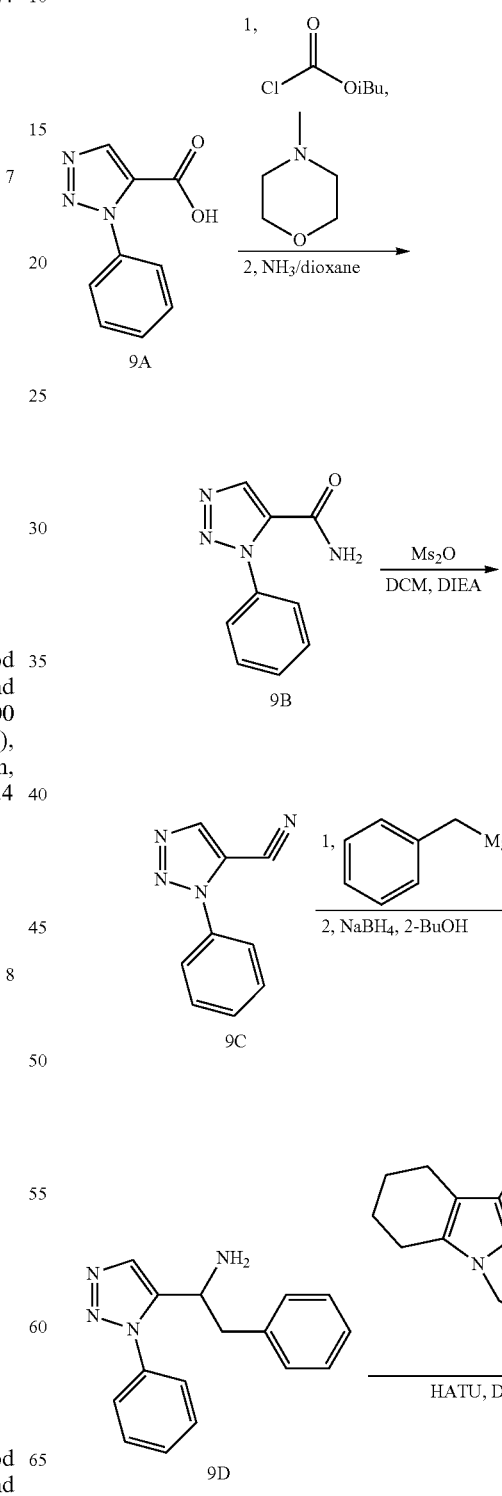

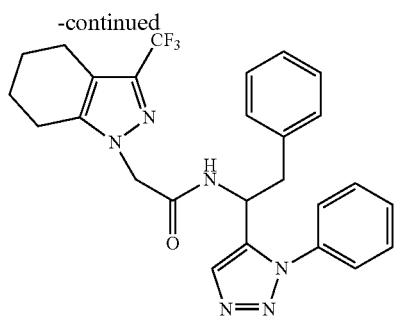

9E

Synthesis of 1-phenyl-1H-1,2,3-triazole-5-carboxamide (9B)

To a solution of 1-phenyl-1H-1,2,3-triazole-5-carboxylic acid (1.0 g, 5.6 mmol) and 4-methylmorpholine (0.57 g, 5.6 mmol) in 1,2-dimethoxyethane (5 mL), isobutyl chloroformate (0.77, 5.6 mmol) was added to the mixture. After 30 minutes, ammonia in dioxane (16.8 mL, 8.4 mmol) was added to the reaction. Then it was stirred overnight. The solvent was removed and dissolved in 50 mL of ethyl acetate. The organic layer was washed with brine twice. The organic layer was dried with $Na_2SO_4$, filtered and concentrated and used without further purification. MS (m/z) 189 $[M+H]^+$.

Synthesis of 1-phenyl-1H-1,2,3-triazole-5-carbonitrile (9C)

To a solution of 9B (crude product) and DIPEA (1.5 mL, 8.4 mmol) in dichloromethane (10 mL), methanesulfonic anhydride (1.17, 6.7 mmol) was added to the mixture. Then it was stirred for overnight. The organic layer was washed with brine twice. The organic layer was dried with $Na_2SO_4$, filtered and concentrated. The crude product was purified by flash column (Rf: 0.6, 15% EtOAc/Hexanes) to provide the desired product. MS (m/z) 171 $[M+H]^+$.

Synthesis of 2-phenyl-1-(1-phenyl-1H-1,2,3-triazol-5-yl)ethanamine (9D)

To a solution of 9C (280 mg, 1.63 mmol) in tetrahydrofuran (5 mL), benzylmagnesium chloride (2M in THF) (1.23 mL, 2.46 mmol) was added dropwise. After 3 hours, 3 mL of 2-butanol was added to the reaction and sodium borohydride (0.5 g) was added to the mixture by portion. The reaction was monitored by LC/Mass until it was done. Methanol (5 mL) was added to the mixture. The organic layer was washed with brine and extracted with ethyl acetate (50 mL twice). The organic layer was dried with $Na_2SO_4$, filtered and concentrated. The crude product was purified by flash column (Rf: 0.3, 3% MeOH/DCM) to provide the desired product. MS (m/z) 265 $[M+H]^+$.

Synthesis of N-(2-phenyl-1-(1-phenyl-1H-1,2,3-triazol-5-yl)ethyl)-2-(3-(trifluoromethyl)-4,5,6,7-tetrahydro-1H-indazol-1-yl)acetamide (9E)

HATU (40 mg, 0.105 mmol) was added to a solution of 2-(3-(trifluoromethyl)-4,5,6,7-tetrahydro-1H-indazol-1-yl) acetic acid (25.0 mg, 0.1 mmol) and DIPEA (0.02 mL, 0.12 mmol) in DMF (0.3 mL). After 10 minutes, 9D (26.5 mg, 0.1 mmol) in 0.2 mL of DMF was added to the reaction. The reaction was stirred for 2 hours. LC/MS shows desired product with a small amount of acid. Purified reaction mixture on prep reverse phase HPLC using 20-80% B over 20 min. (A=0.1% TFA/H2O; B=0.1% TFA/Acetonitrile). Combined pure fractions as determined by LC/MS and lyophilized to provide the desired compound. $^1$H NMR (400 MHz, DMSO) δ 9.02 (d, J=7.9 Hz, 1H), 7.96 (s, 1H), 7.58-7.42 (m, 3H), 7.30-7.18 (m, 2H), 7.18-7.06 (m, 3H), 7.00-6.86 (m, 2H), 5.06 (q, J=7.6 Hz, 1H), 4.74-4.61 (m, 2H), 2.98 (td, J=13.6, 6.4 Hz, 2H), 2.43 (s, 2H), 2.37-2.17 (m, 2H), 1.61 (d, J=5.9 Hz, 4H). MS (m/z) 495 $[M+H]^+$.

EXAMPLE 10

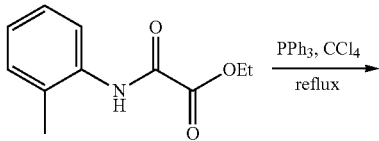

10A

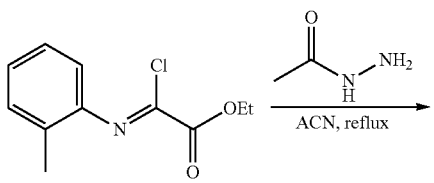

10B

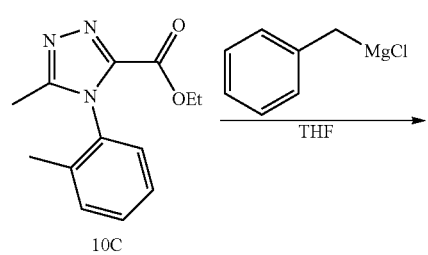

10C

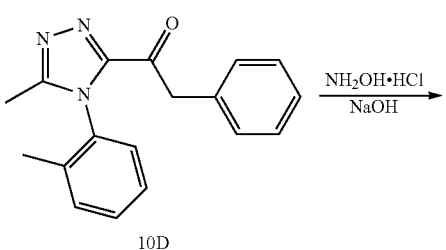

10D

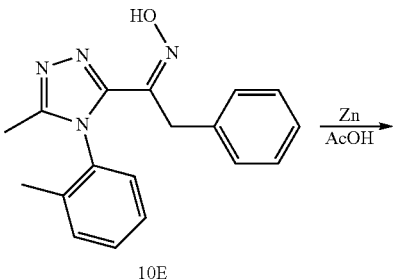

10E

-continued

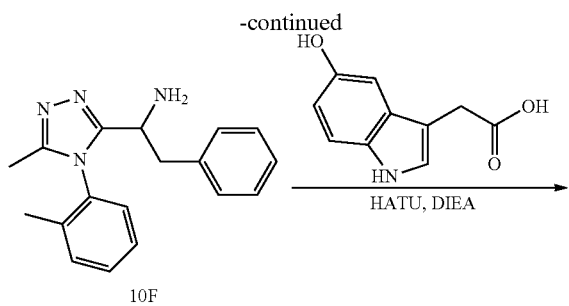

10F

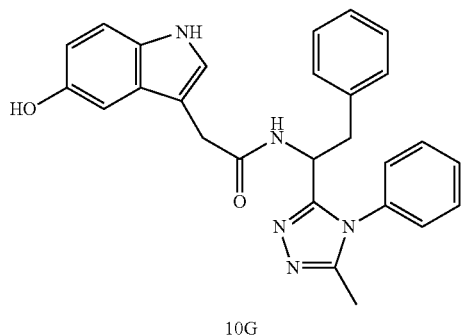

10G

Synthesis of ethyl 2-chloro-2-(o-tolylimino)acetate (10B)

The suspension of ethyl 2-oxo-2-(o-tolylamino)acetate (2.0 g, 10 mmol) and triphenylphosphine (4.0 g, 15 mmol) in carbon tetrachloride (150 mL) was refluxed overnight. The reaction was cooled down and filtered. The filtrate was collected and concentrated and used it without further purification. MS (m/z) 226 [M+H]$^+$.

Synthesis of ethyl 5-methyl-4-(o-tolyl)-4H-1,2,4-triazole-3-carboxylate (10C)

The suspension of 10B and acetohydrazide in acetonitrile was refluxed for 2 hours. The solvent was removed. The crude product was purified by flash column (Rf: 0.2, 50% EtOAc/Hexanes). MS (m/z) 246 [M+H]$^+$.

Synthesis of 1-(5-methyl-4-(o-tolyl)-4H-1,2,4-triazol-3-yl)-2-phenylethanone (10D)

To a solution of 10C (1.0 g, 4.1 mmol) in toluene cooled by an ice bath, benzylmagnesium chloride (2M in THF) (3.0 mL, 6.0 mmol) was added dropwise. After one hour, ammonia chloride solution was added to the mixture and extracted with ethyl acetate (50 mL twice). The organic layer was dried with Na$_2$SO$_4$, filtered and concentrated and used without further purification. MS (m/z) 292 [M+H]$^+$.

Synthesis of 1-(5-methyl-4-(o-tolyl)-4H-1,2,4-triazol-3-yl)-2-phenylethanone oxime (10E)

To a suspension of 10D and hydroxylamine hydrochloride (420 mg, 6 mmol) in ethanol (5 mL), sodium hydroxide (480 mg, 12 mmol) was added. It was refluxed for two hours. The reaction was acidified with 1 N hydrochloride and extracted with ethyl acetate (50 mL twice). The organic layer was dried with Na$_2$SO$_4$, filtered and concentrated. The crude product was purified by flash column to provide the desired product. MS (m/z) 307 [M+H]$^+$.

Synthesis of 1-(5-methyl-4-(o-tolyl)-4H-1,2,4-triazol-3-yl)-2-phenylethanamine (10F)

The suspension of 10E (120 mg, 0.4 mmol) and zinc powder (256 mg, 4 mmol) in 2 mL of acetic acid was heated to reflux for 30 minutes. The reaction was filtered and purified on prep reverse phase HPLC using 20-80% B over 20 min. (A=0.1% TFA/H$_2$O; B=0.1% TFA/Acetonitrile). Combined pure fractions as determined by LC/MS and lyophilized to provide the desired product. MS (m/z) 293 [M+H]$^+$.

Synthesis of 2-(5-hydroxy-1H-indol-3-yl)-N-(1-(5-methyl-4-phenyl-4H-1,2,4-triazol-3-yl)-2-phenylethyl)acetamide (10G)

HATU (40 mg, 0.105 mmol) was added to a solution of 2-(5-hydroxy-1H-indol-3-yl)acetic acid (19.2 mg, 0.1 mmol) and DIPEA (0.02 mL, 0.12 mmol) in DMF (0.3 mL). After 10 minutes, 10F (29.2 mg, 0.1 mmol) in 0.2 mL of DMF was added to the reaction. The reaction was stirred for 2 hours. LC/MS shows desired product with a small amount of acid. Purified reaction mixture on prep reverse phase HPLC using 20-80% B over 20 min. (A=0.1% TFA/H$_2$O; B=0.1% TFA/Acetonitrile). Combined pure fractions as determined by LC/MS and lyophilized to provide) to provide the desired product. $^1$H NMR (400 MHz, DMSO) δ 10.44 (s, 1H), 8.64-8.42 (m, 1H), 7.50-7.19 (m, 3H), 7.17-6.93 (m, 6H), 6.81 (dd, J=53.1, 21.8 Hz, 4H), 6.54 (d, J=8.8 Hz, 1H), 3.39-3.22 (m, 3H), 3.09-2.85 (m, 2H), 2.01 (d, J=15.7 Hz, 3H). MS (m/z) 452 [M+H]$^+$.

EXAMPLE 11

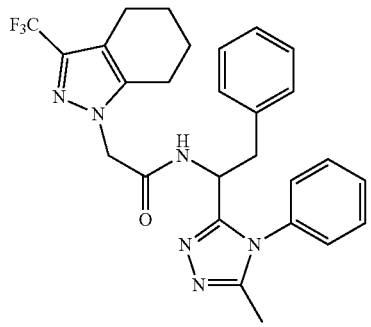

11

Synthesis of N-(1-(5-methyl-4-phenyl-4H-1,2,4-triazol-3-yl)-2-phenylethyl)-2-(3-(trifluoromethyl)-4,5,6,7-tetrahydro-1H-indazol-1-yl)acetamide (11)

HATU (40 mg, 0.105 mmol) was added to a solution of 2-(3-(trifluoromethyl)-4,5,6,7-tetrahydro-1H-indazol-1-yl)acetic acid (25.0 mg, 0.1 mmol) and DIPEA (0.02 mL, 0.12 mmol) in DMF (0.3 mL). After 10 minutes, 10F (29.2 mg, 0.1 mmol) in 0.2 mL of DMF was added to the reaction. The reaction was stirred for 2 hours. LC/MS shows desired product with a small amount of acid. Purified reaction mixture on prep reverse phase HPLC using 20-80% B over 20 min. (A=0.1% TFA/H$_2$O; B=0.1% TFA/Acetonitrile). Combined pure fractions as determined by LC/MS and lyophilized to provide the desired product. $^1$H NMR (400 MHz, DMSO) δ 9.16-8.86 (m, 1H), 7.39 (dd, J=16.8, 8.4 Hz, 2H), 7.28 (d, J=7.2 Hz, 1H), 7.16 (t, J=6.3 Hz, 3H), 6.90 (td, J=51.4, 7.6 Hz, 3H), 4.74-4.51 (m, 3H), 3.10 (s, 1H), 2.94 (dd, J=13.5, 8.9 Hz, 1H), 2.44-2.10 (m, 4H), 2.03 (d, J=4.7 Hz, 3H), 1.59 (s, 4H). MS (m/z) 509 [M+H]$^+$.

EXAMPLE 12

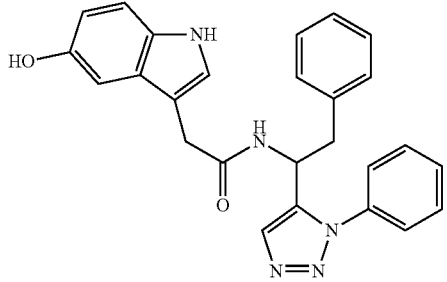

12

Synthesis of 2-(5-hydroxy-1H-indol-3-yl)-N-(2-phenyl-1-(1-phenyl-1H-1,2,3-triazol-5-yl)ethyl)acetamide (12)

HATU (40 mg, 0.105 mmol) was added to a solution of 2-(5-hydroxy-1H-indol-3-yl)acetic acid (19.2 mg, 0.1 mmol) and DIPEA (0.02 mL, 0.12 mmol) in DMF (0.3 mL). After 10 minutes, 9D (26.5 mg, 0.1 mmol) in 0.2 mL of DMF was added to the reaction. The reaction was stirred for 2 hours. LC/MS shows desired product with a small amount of acid. Purified reaction mixture on prep reverse phase HPLC using 20-80% B over 20 min. (A=0.1% TFA/H2O; B=0.1% TFA/Acetonitrile). Combined pure fractions as determined by LC/MS and lyophilized to provide the desired product. $^1$H NMR (400 MHz, CD$_3$OD) δ 7.76 (s, 1H), 7.47 (t, J=7.5 Hz, 1H), 7.39 (t, J=7.6 Hz, 2H), 7.21-7.01 (m, 6H), 6.96 (s, 1H), 6.84 (d, J=1.9 Hz, 1H), 6.78 (d, J=6.8 Hz, 2H), 6.68 (dd, J=8.6, 2.3 Hz, 1H), 5.46 (s, 2H), 5.21 (t, J=7.6 Hz, 1H), 2.96 (ddd, J=21.5, 13.3, 7.6 Hz, 2H); MS (m/z) 438 [M+H]$^+$.

EXAMPLE 13

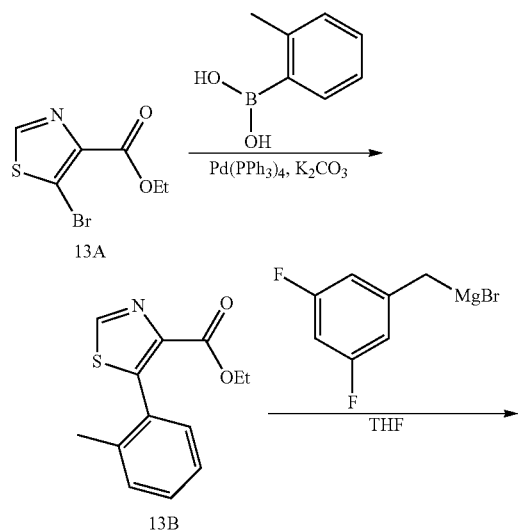

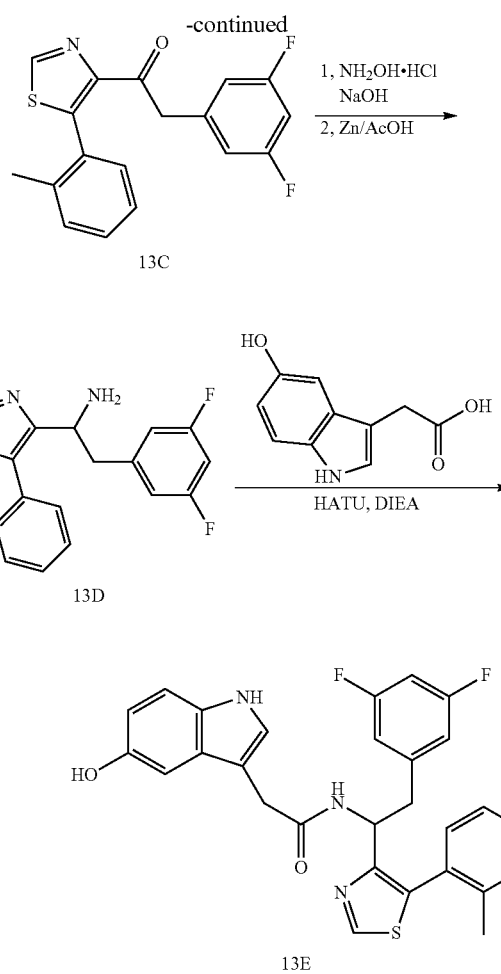

Synthesis of 3-o-tolylpicolinonitrile(13B)

The suspension of ethyl 5-bromothiazole-4-carboxylate (1.0 g, 4.5 mmol), potassium carbonate (23 mL, 0.4M in water), o-tolylboronic acid (613 mg, 4.5 mmol) and tetrakis(triphenylphosphine) palladium (260 mg, 0.225 mmol) in DME (40 mL) was degassed for 20 minutes. The mixture was then heated at reflux. After 2 hours the reaction was filtered through celite and the filtrate was extracted with EtOAc (30 mL) twice. The organic layer was dried over Na$_2$SO$_4$, filtered and concentrated. The crude product was purified by flash column (Rf: 0.3 EtOAc/Hexanes=20%) to provide the desired product. MS (m/z) 248 [M+H]$^+$.

Synthesis of 2-(3,5-difluorophenyl)-1-(5-(o-tolyl)thiazol-4-yl)ethanone (13C)

To a solution of 13B (0.5 g, 2.15 mmol) in 6 mL of tetrahydrofuran cooled by an ice bath, (3,5-difluorobenzyl)magnesium bromide (0.25M in ether) (14.6 mL, 3.65 mmol) was added dropwise. After one hour, ammonia chloride solution was added to the mixture and extracted with ethyl acetate (50 mL twice). The organic layer was dried with Na$_2$SO$_4$, filtered and concentrated. The crude product was purified by flash column (Rf: 0.3 EtOAc/Hexanes=10%). to provide the desired product. MS (m/z) 330 [M+H]$^+$.

Synthesis of 2-(3,5-difluorophenyl)-1-(5-(o-tolyl)thiazol-4-yl)ethanamine (13D)

Compound 13D was prepared according to the method presented for the synthesis of Example 10 substituting 13C for 10D to provide to provide the desired product. MS (m/z) 331 [M+H]$^+$.

Synthesis of N-(2-(3,5-difluorophenyl)-1-(5-(o-tolyl)thiazol-4-yl)ethyl)-2-(5-hydroxy-1H-indol-3-yl)acetamide (13E)

HATU (40 mg, 0.105 mmol) was added to a solution of 2-(5-hydroxy-1H-indol-3-yl)acetic acid (19.2 mg, 0.1 mmol) and DIPEA (0.02 mL, 0.12 mmol) in DMF (0.3 mL). After 10 minutes, 13D (33.1 mg, 0.1 mmol) in 0.2 mL of DMF was added to the reaction. The reaction was stirred for 2 hours. LC/MS shows desired product. Purified reaction mixture on prep reverse phase HPLC using 20-80% B over 20 min. (A=0.1% TFA/H2O; B=0.1% TFA/Acetonitrile). Combined pure fractions as determined by LC/MS and lyophilized to provide the desired product. $^1$H NMR (400 MHz, DMSO) δ 10.46 (s, 1H), 9.18 (s, 1H), 8.31 (d, J=8.2 Hz, 1H), 7.35-7.15 (m, 2H), 7.05 (t, J=7.1 Hz, 2H), 6.94 (dd, J=10.2, 5.8 Hz, 2H), 6.75 (t, J=7.2 Hz, 2H), 6.59-6.35 (m, 3H), 3.38 (s, 2H), 3.01 (d, J=7.5 Hz, 2H), 1.81 (s, 3H). MS (m/z) 504 [M+H]$^+$.

EXAMPLE 14

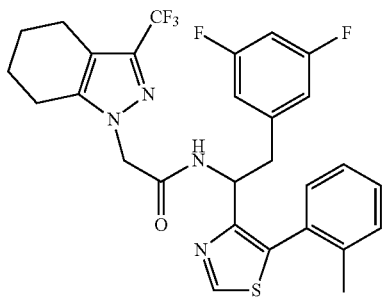

14

Synthesis of N-(2-(3,5-difluorophenyl)-1-(5-(o-tolyl)thiazol-4-yl)ethyl)-2-(3-(trifluoromethyl)-4,5,6,7-tetrahydro-1H-indazol-1-yl)acetamide (14)

HATU (40 mg, 0.105 mmol) was added to a solution of 2-(3-(trifluoromethyl)-4,5,6,7-tetrahydro-1H-indazol-1-yl) acetic acid (25.0 mg, 0.1 mmol) and DIPEA (0.02 mL, 0.12 mmol) in DMF (0.3 mL). After 10 minutes, 13D (33.1 mg, 0.1 mmol) in 0.2 mL of DMF was added to the reaction. The reaction was stirred for 2 hours. LC/MS shows desired product with a small amount of acid. Purified reaction mixture on prep reverse phase HPLC using 20-80% B over 20 min. (A=0.1% TFA/H2O; B=0.1% TFA/Acetonitrile). Combined pure fractions as determined by LC/MS and lyophilized to provide the desired product. $^1$H NMR (400 MHz, DMSO) δ 9.23 (s, 1H), 8.89 (d, J=8.3 Hz, 1H), 7.35-7.16 (m, 2H), 7.11 (t, J=7.6 Hz, 1H), 6.99 (t, J=9.5 Hz, 1H), 6.79 (d, J=7.2 Hz, 1H), 6.51 (d, J=6.4 Hz, 2H), 4.83-4.77 (m, 1H), 4.72 (s, 2H), 3.05 (d, J=7.7 Hz, 2H), 2.46-2.21 (m, 4H), 1.87 (s, 3H), 1.61 (s, 4H). MS (m/z) 561 [M+H]$^+$.

EXAMPLE 15

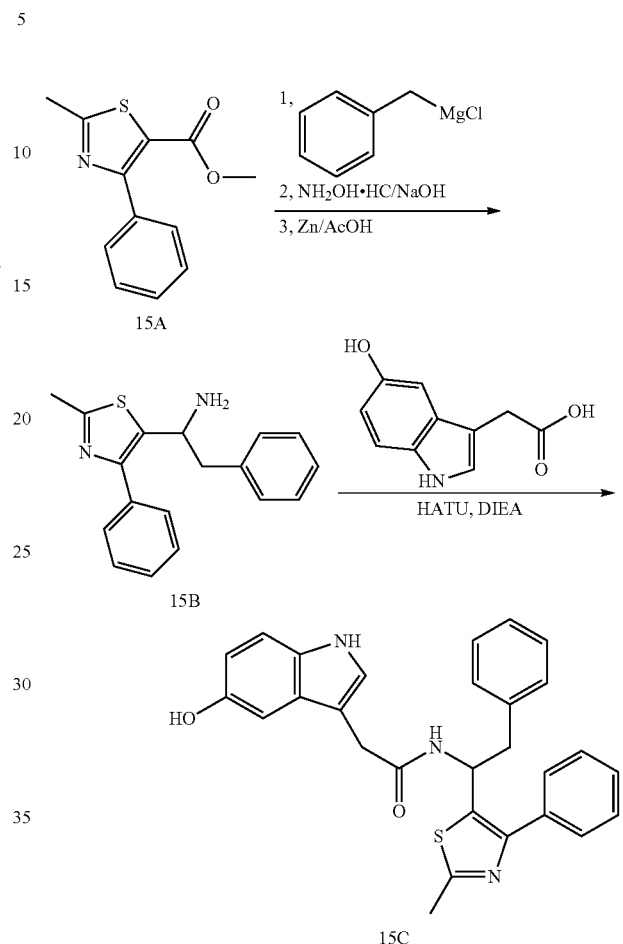

Synthesis of 1-(2-methyl-4-phenylthiazol-5-yl)-2-phenylethanamine (15B)

Compound 15B was prepared according to the method presented for the synthesis of Example 10 substituting 15A for 10C to provide the desired product. MS (m/z) 295 [M+H]$^+$.

Synthesis of 2-(5-hydroxy-1H-indol-3-yl)-N-(1-(2-methyl-4-phenylthiazol-5-yl)-2-phenylethyl)acetamide (15C)

HATU (40 mg, 0.105 mmol) was added to a solution of 2-(5-hydroxy-1H-indol-3-yl)acetic acid (19.2 mg, 0.1 mmol) and DIPEA (0.02 mL, 0.12 mmol) in DMF (0.3 mL). After 10 minutes, 15B (29.4 mg, 0.1 mmol) in 0.2 mL of DMF was added to the reaction. The reaction was stirred for 2 hours. LC/MS shows desired product with a small amount of acid. Purified reaction mixture on prep reverse phase HPLC using 20-80% B over 20 min. (A=0.1% TFA/H2O; B=0.1% TFA/ Acetonitrile). Combined pure fractions as determined by LC/MS and lyophilized to provide the desired product. $^1$H NMR (400 MHz, DMSO) δ 10.46 (s, 1H), 8.59 (d, J=7.6 Hz, 1H), 7.44-7.22 (m, 5H), 7.07 (dd, J=5.5, 3.2 Hz, 4H), 6.92 (dd, J=6.5, 2.9 Hz, 3H), 6.80 (d, J=2.2 Hz, 1H), 6.55 (dd, J=8.6, 2.3 Hz, 1H), 5.34 (dd, J=15.0, 7.5 Hz, 1H), 3.36 (s, 2H), 3.07 (dd, J=13.8, 7.9 Hz, 1H), 2.84 (dd, J=13.5, 7.0 Hz, 1H), 2.60 (s, 3H); MS (m/z) 468 [M+H]+.

EXAMPLE 16

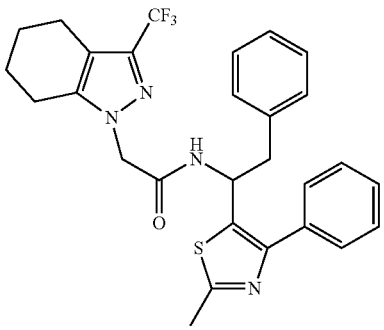

16

Synthesis of (S)-N-(1-(2-methyl-4-phenylthiazol-5-yl)-2-phenylethyl)-2-(3-(trifluoromethyl)-4,5,6,7-tetrahydro-1H-indazol-1-yl)acetamide (16)

HATU (40 mg, 0.105 mmol) was added to a solution of 2-(3-(trifluoromethyl)-4,5,6,7-tetrahydro-1H-indazol-1-yl)acetic acid (25.0 mg, 0.1 mmol) and DIPEA (0.02 mL, 0.12 mmol) in DMF (0.3 mL). After 10 minutes, 15B (29.4 mg, 0.1 mmol) in 0.2 mL of DMF was added to the reaction. The reaction was stirred for 2 hours. LC/MS shows desired product with a small amount of acid. Purified reaction mixture on prep reverse phase HPLC using 20-80% B over 20 min. (A=0.1% TFA/H2O; B=0.1% TFA/Acetonitrile). Combined pure fractions as determined by LC/MS and lyophilized to provide the desired product. $^1$H NMR (400 MHz, DMSO) δ 9.02 (d, J=7.8 Hz, 1H), 7.46-7.26 (m, 4H), 7.13 (t, J=6.1 Hz, 3H), 6.99 (d, J=7.7 Hz, 2H), 5.37 (dd, J=14.8, 7.3 Hz, 1H), 4.68 (t, J=12.7 Hz, 2H), 2.99 (ddd, J=20.2, 13.5, 7.3 Hz, 2H), 2.63 (s, 3H), 2.45-2.19 (m, 4H), 1.61 (d, J=5.5 Hz, 4H); MS (m/z) 525 [M+H]+.

EXAMPLE 17

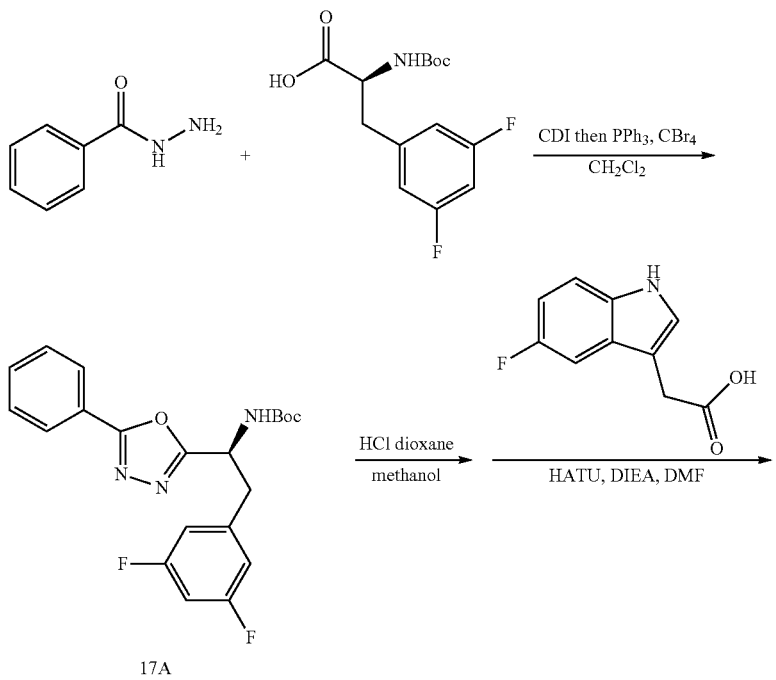

17A

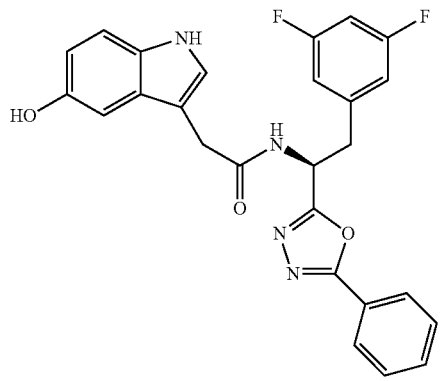

17B

Synthesis of (S)-tert-butyl 2-(3,5-difluorophenyl)-1-(5-phenyl-1,3,4-oxadiazol-2-yl)ethylcarbamate (17A)

To a solution of N-Boc-(L)-3,5-di-F-Phe-OH (301 mg, 1 mmol) in 5 mL of methylene chloride at 0° C. was added CDI (170 mg, 1.05 mmol). After 30 min, benzyl hydrazide (136 mg, 1 mmol) was added. The coupling was allowed to proceed at 0° C. for 45 min, then $CBr_4$ (665 mg, 2 mmol) and $PPh_3$ (polymer-bond, ~3 mmol/g, 667 mg, 2 mmol) were added. The dehydration step was allowed to proceed at 0° C. for 2 hours then at ambient temperature for over a weekend. The reaction mixture was filtered and the filtrate purified by silica gel chromatography eluting with EtOAc/hexanes to afford the desired product. MS (m/z): 401.9 [M+H]$^+$.

Synthesis of (S)-N-(2-(3,5-difluorophenyl)-1-(5-phenyl-1,3,4-oxadiazol-2-yl)ethyl)-2-(5-fluoro-1H-indol-3-yl)acetamide (17B)

(S)-tert-Butyl 2-(3,5-difluorophenyl)-1-(5-phenyl-1,3,4-oxadiazol-2-yl)ethylcarbamate (17A, 110 mg, 0.27 mmol) was dissolved in 2.7 mL of methanol and to it was added 0.7 mL of 4M HCl in 1,4-dioxane. The reaction mixture was allowed to stir at ambient temperature for 1 hour and the solvent was removed in vacuo. The residue was purified by silica gel chromatography eluting with methanol/methylene chloride to afford 90 mg of (S)-2-(3,5-difluorophenyl)-1-(5-phenyl-1,3,4-oxadiazol-2-yl)ethanamine (0.26 mmol) which was dissolved in 5 mL of DMF and to it were added 2-(5-fluoro-1H-indol-3-yl)acetic acid (61 mg, 0.31 mmol) and N,N-diisopropylethylamine (0.226 mL, 1.3 mmol). The reaction mixture was cooled down to 0° C. and to it was added HATU (119 mg, 0.31 mmol). The reaction mixture was allowed to stir at ambient temperature for overnight and then purified by reverse phase HPLC eluting with acetonitrile/water (0.1% TFA) to afford the desired product. $^1$H NMR (400 MHz, DMSO) δ 10.93 (s, 1H), 8.79 (d, J=8.2 Hz, 1H), 7.94-7.73 (m, 2H), 7.56 (m, 3H), 7.27 (dd, J=8.7, 4.5 Hz, 1H), 7.12 (m, 2H), 7.00 (m, 3H), 6.84 (td, J=9.2, 2.5 Hz, 1H), 5.44 (m, 1H),), 3.52-3.12 (m, 4H). MS (m/z): 477.1 [M+H]$^+$.

EXAMPLE 18

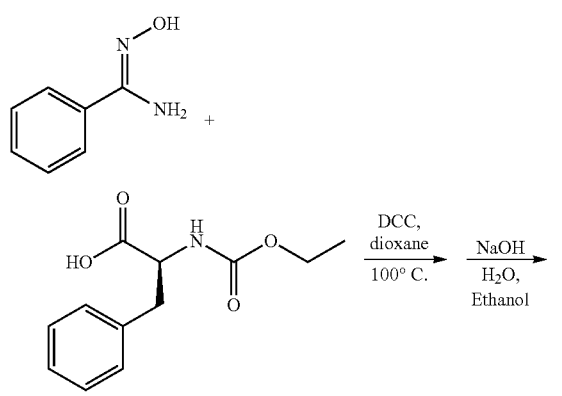

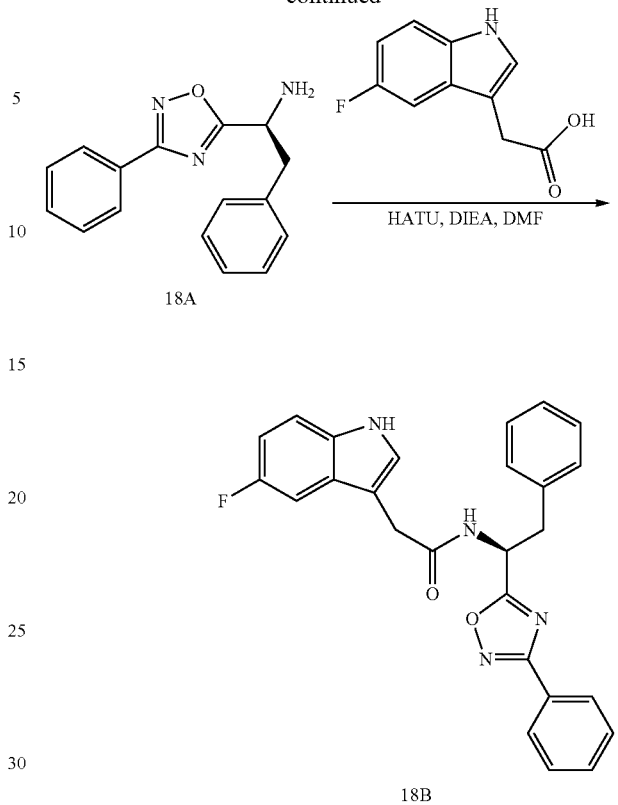

Synthesis of (S)-2-phenyl-1-(3-phenyl-1,2,4-oxadiazol-5-yl)ethanamine (18A)

N,N'-dicyclohexylcarbodiimide (454 mg, 2.2 mmol) was added to a solution of benzamidooxime (272 mg, 2 mmol) and N-ethyoxycarbonyl-L-phenylalanine (475 mg, 2 mmol) in 1,4-dioxane (20 mL). The reaction mixture was heated under stirring at 100° C. for 16 hours. The solvent was removed under vacuum and the residue purified by silica gel chromatography eluting with EtOAc/hexanes to afford 280 mg of (S)-ethyl 2-phenyl-1-(3-phenyl-1,2,4-oxadiazol-5-yl)ethylcarbamate which was dissolved in 10 mL of ethanol and 10 mL of 10% NaOH aqueous solution. The mixture was heated up to 100° C. for 3 hours, and then cooled down to ambient temperature. After extracted with methylene chloride, the organic layer was separated and dried over sodium sulfate, filtered and concentrated to afford the desired product. MS (m/z): 266.1 [M+H]$^+$.

Synthesis of (S)-2-(5-fluoro-1H-indol-3-yl)-N-(2-phenyl-1-(3-phenyl-1,2,4-oxadiazol-5-yl)ethyl)acetamide (18B)

The title compound was prepared according to the method presented for the synthesis of compound 5F of Example 5 utilizing 18A and 2-(5-fluoro-1H-indol-3-yl)acetic acid. $^1$H NMR (400 MHz, DMSO) δ 10.92 (s, 1H), 8.90 (d, J=8.0 Hz, 1H), 7.94 (m, 2H), 7.68-7.39 (m, 3H), 7.37-7.06 (m, 8H), 6.85

(td, J=9.2, 2.5 Hz, 1H), 5.34 (dd, J=13.8, 9.2 Hz, 1H), 3.46-3.20 (m, 4H); MS (m/z) 441.1 [M+H]+.

EXAMPLE 19

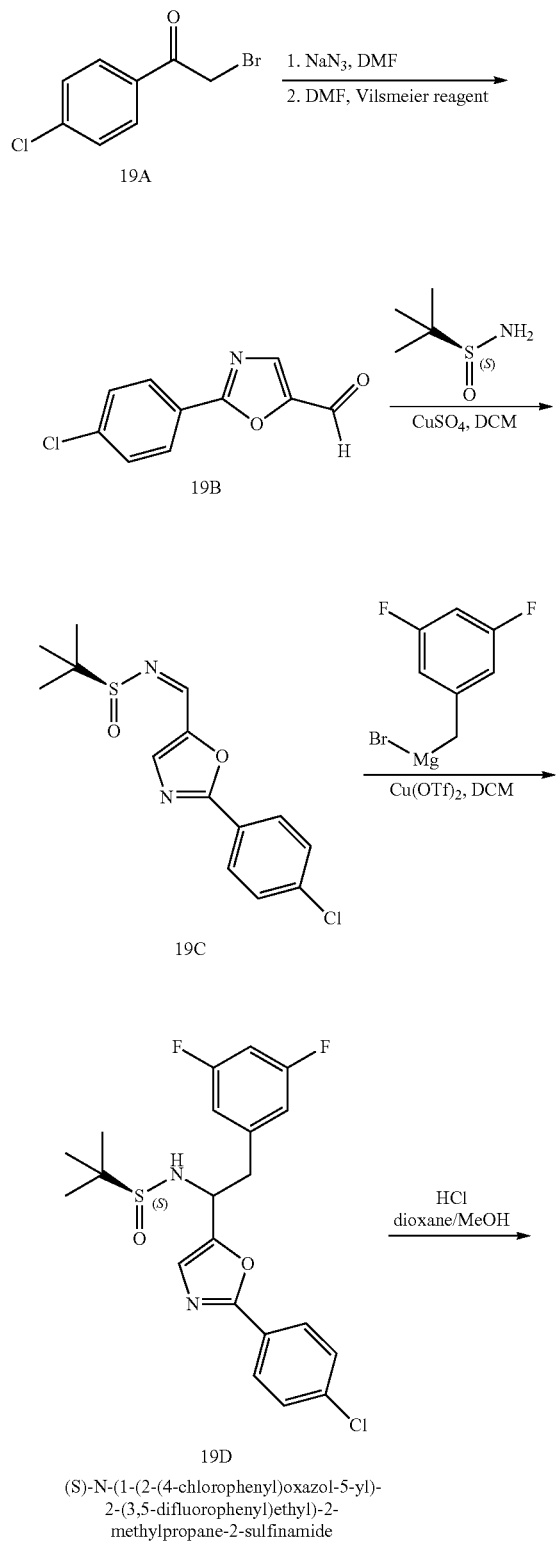

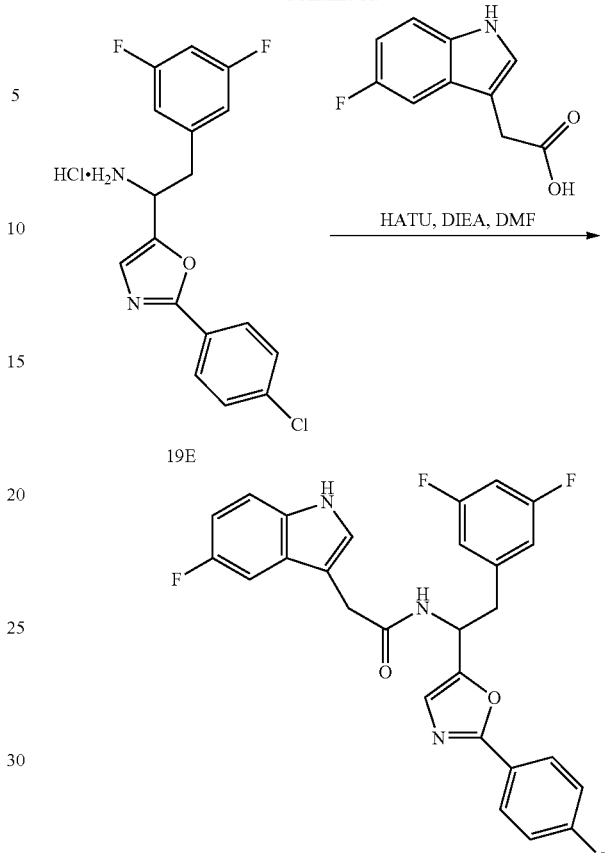

Synthesis of 2-(4-chlorophenyl)oxazole-5-carbaldehyde (19B)

NaN₃ (1.1 equiv) was added in one portion to an ice-cooled, stirred solution of 2-bromo-1-(4-chlorophenyl)ethanone (23.1 g, 100 mmol) in DMF (100 mL). After stirring the suspension for 40 min to give a yellow solution, 6 equiv of POCl₃ was then added dropwise. The temperature was warmed to 80-90° C. and maintained at this temperature for 16 h. The crude product was poured into water and stirred at r.t. for 1 h, extracted with ethyl acetate, washed with water, purified by silica column with DCM:acetone=100% to 5:1 to give a yellow solid which was crystallized from petroleum ether to give a white solid. (Yield: 2 g, 11%). MS (m/z) 208.1 [M+H]+.

Synthesis of (Z)-N-((2-(4-chlorophenyl)oxazol-5-yl)methylene)-2-methylpropane-2-sulfinamide (19C)

The title compound was prepared according to the method presented for the synthesis of compound 5B of Example 5 utilizing 19B and (S)-2-methylpropane-2-sulfinamide. MS (m/z) 311.1 [M+H]+.

Synthesis of (Z)-N-((2-(4-chlorophenyl)oxazol-5-yl)methylene)-2-methylpropane-2-sulfinamide (19D)

The title compound was prepared as a mixture of diastereomers according to the method presented for the synthesis of compound 5C and 5D of Example 5 utilizing 19C and (3,5-difluorobenzyl)magnesium bromide. MS (m/z) 439.1 [M+H]+.

Synthesis of 1-(2-(4-chlorophenyl)oxazol-5-yl)-2-(3,5-difluorophenyl)ethanamine hydrochloride (19E)

The title compound was prepared according to the method presented for the synthesis of compound 5E of Example 5 utilizing 19D. MS (m/z) 335.2 [M+H]+.

Synthesis of N-(1-(2-(4-chlorophenyl)oxazol-5-yl)-2-(3,5-difluorophenyl)ethyl)-2-(5-fluoro-1H-indol-3-yl)acetamide (19F)

The title compound was prepared according to the method presented for the synthesis of compound 5F of Example 5 utilizing 19E and 2-(5-fluoro-1H-indol-3-yl)acetic acid. $^1$H NMR (400 MHz, CDCl$_3$) δ 8.21 (s, 1H), 7.81 (d, J=8.5 Hz, 2H), 7.43 (d, J=8.5 Hz, 2H), 7.38-7.23 (m, 2H), 7.16 (s, 1H), 7.05 (d, J=9.3 Hz, 1H), 6.95 (dd, J=10.3, 7.7 Hz, 1H), 6.61 (t, J=9.0 Hz, 1H), 6.50 (dd, J=14.6, 7.6 Hz, 3H), 5.27 (q, J=7.4 Hz, 1H), 3.72 (s, 2H), 3.08 (dd, J=13.7, 7.1 Hz, 1H), 2.95 (dd, J=13.7, 7.4 Hz, 1H). MS (m/z) 510.1 [M+H]+.

EXAMPLE 20

Synthesis of N-(1-(2-(4-chlorophenyl)oxazol-5-yl)-2-(3,5-difluorophenyl)ethyl)-2-(3-(trifluoromethyl)-4,5,6,7-tetrahydro-1H-indazol-1-yl)acetamide (20)

The title compound was prepared according to the method presented for the synthesis of compound 5F of Example 5 utilizing 19E and 2-(3-(trifluoromethyl)-4,5,6,7-tetrahydro-1H-indazol-1-yl)acetic acid. $^1$H NMR (400 MHz, CDCl$_3$) δ 7.93 (d, J=8.6 Hz, 2H), 7.45 (d, J=8.5 Hz, 2H), 7.35 (s, 1H), 6.90 (d, J=8.3 Hz, 1H), 6.69-6.52 (m, 3H), 5.24 (q, J=7.6 Hz, 1H), 4.69 (s, 2H), 3.09 (ddd, J=33.5, 13.7, 7.3 Hz, 2H), 2.54 (m, 2H), 2.42-2.37 (m, 2H), 1.81-1.70 (m, 4H). MS (m/z) 565.1 [M+H]+.

EXAMPLE 21

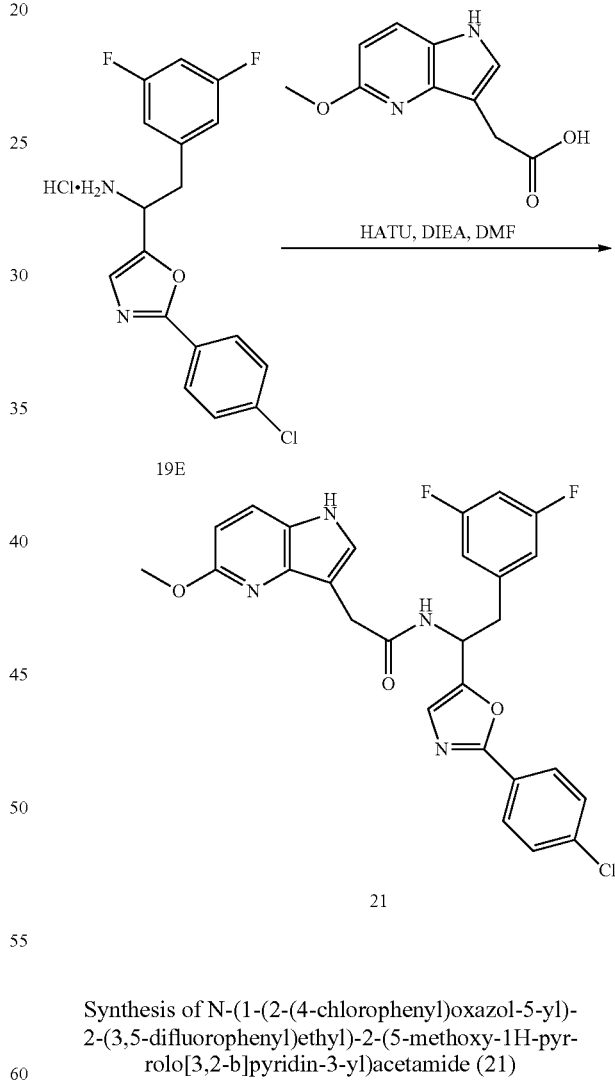

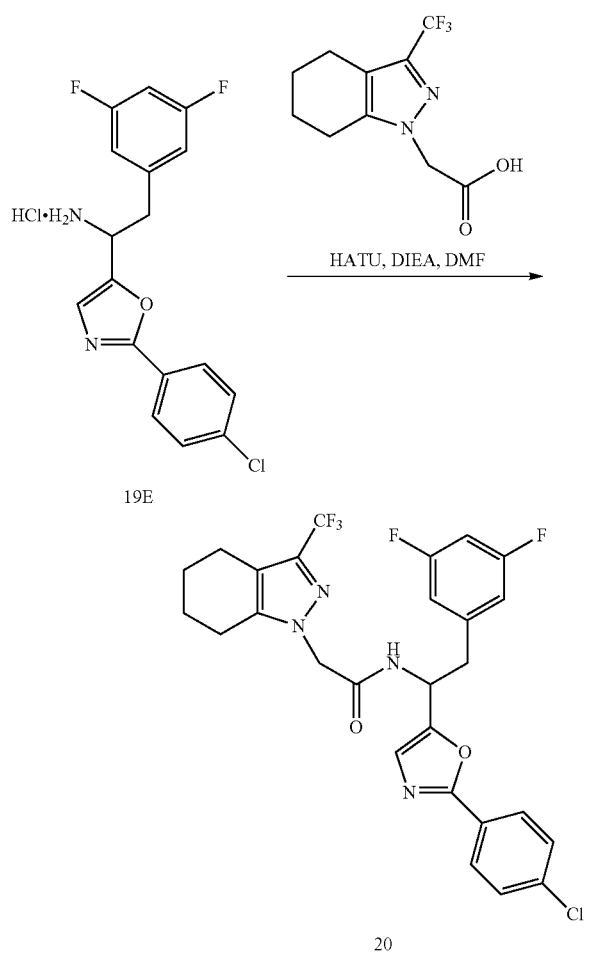

Synthesis of N-(1-(2-(4-chlorophenyl)oxazol-5-yl)-2-(3,5-difluorophenyl)ethyl)-2-(5-methoxy-1H-pyrrolo[3,2-b]pyridin-3-yl)acetamide (21)

The title compound (6.0 mg) was prepared according to the method presented for the synthesis of compound 5F of Example 5 utilizing 19E and 2-(5-methoxy-1H-pyrrolo[3,2-b]pyridin-3-yl)acetic acid. $^1$H NMR (400 MHz, DMSO) δ 11.6 (br, 1H), 8.50 (d, J=8.5 Hz, 1H), 8.40 (s, 1H), 8.01 (s, 1H), 7.89 (d, J=8.5 Hz, 2H), 7.55 (d, J=8.6 Hz, 3H), 7.03 (s, 1H), 6.83 (d, J=7.8 Hz, 3H), 5.08 (d, J=5.3 Hz, 1H), 3.82 (s, 3H), 3.44 (s, 2H), 3.23-3.06 (m, 1H), 3.04-2.91 (m, 1H). MS (m/z) 523.1 [M+H]⁺.

EXAMPLE 22

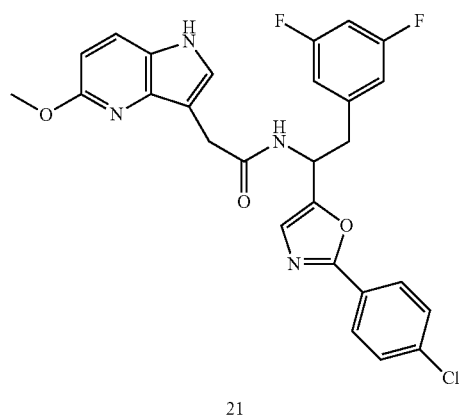

21

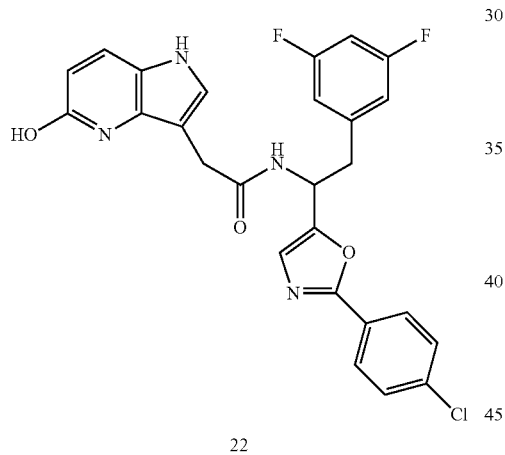

22

Synthesis of N-(1-(2-(4-chlorophenyl)oxazol-5-yl)-2-(3,5-difluorophenyl)ethyl)-2-(5-hydroxy-1H-pyrrolo[3,2-b]pyridin-3-yl)acetamide (22)

A solution of 21 (20 mg, 0.038 mmol) and KI (33 mg, 0.2 mmol) in acetic acid (5 mL) was heated in a microwave reactor at 160° C. for 10 min. After cooling to room temperature and removing the volatiles in vacuo, the resulting residue was purified by reverse phase HPLC to yield the title compound. ¹H NMR (400 MHz, DMSO) δ 11.89 (s, 1H), 8.53 (d, J=8.5 Hz, 1H), 8.44 (s, 1H), 8.06 (s, 1H), 7.94 (d, J=8.5 Hz, 2H), 7.80 (s, 1H), 7.61 (d, J=8.6 Hz, 2H), 7.02 (s, 1H), 6.86 (m, 3H), 5.10 (m, 1H), 3.20-3.16 (m, 1H), 3.01-2.95 (m, 1H). MS (m/z) 508.9 [M+H]⁺.

EXAMPLE 23

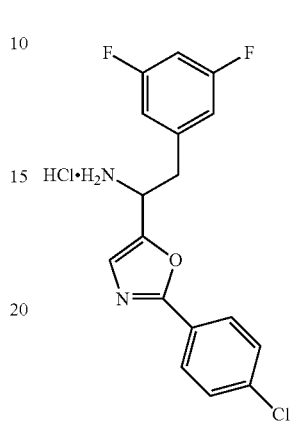

19E

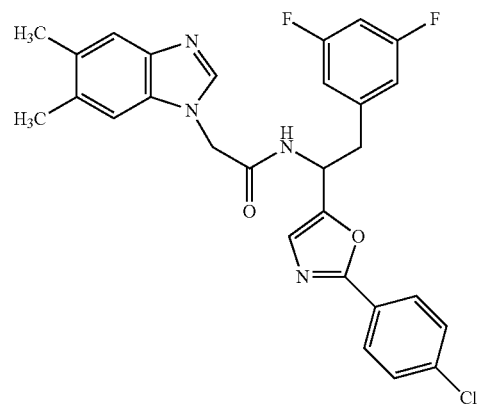

23

Synthesis of N-(1-(2-(4-chlorophenyl)oxazol-5-yl)-2-(3,5-difluorophenyl)ethyl)-2-(5,6-dimethyl-1H-benzo[d]imidazol-1-yl)acetamide (23)

The title compound was prepared according to the method presented for the synthesis of compound 5F of Example 5 utilizing 19E and 2-(5,6-dimethyl-1H-benzo[d]imidazol-1-yl)acetic acid. ¹H NMR (400 MHz, DMSO) δ 9.06-8.94 (m, 2H), 8.10 (s, 1H), 7.92 (d, J=8.5 Hz, 2H), 7.57 (d, J=8.6 Hz, 2H), 7.50 (s, 1H), 7.17 (s, 1H), 6.97 (m, 3H), 5.17-4.95 (m, 3H), 3.24-3.07 (m, 1H), 3.04 (dd, J=13.7, 9.7 Hz, 1H), 2.29 (s, 1H), 2.22 (s, 1H). MS (m/z) 520.9 [M+H]+.

EXAMPLE 24

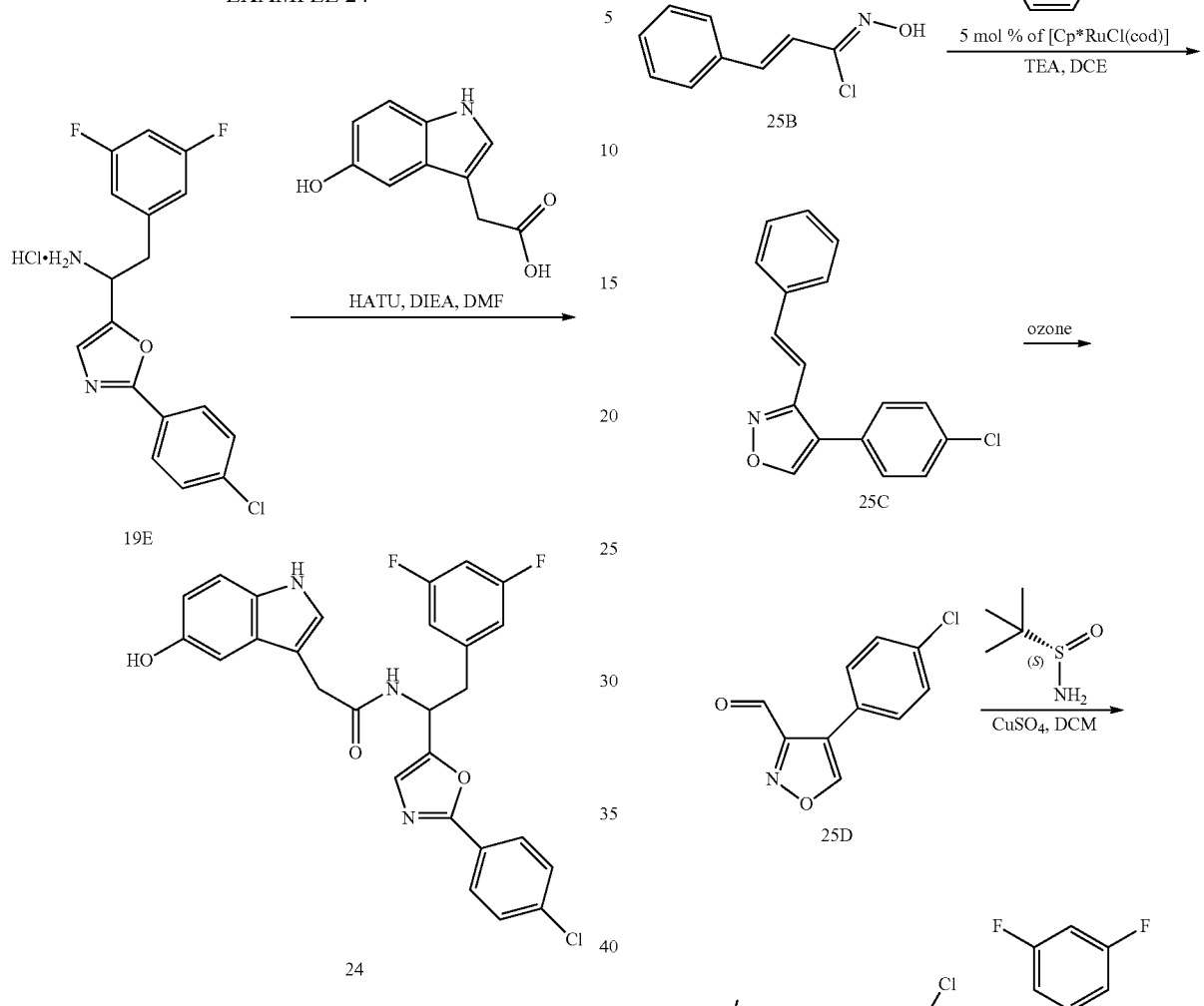

Synthesis of N-(1-(2-(4-chlorophenyl)oxazol-5-yl)-2-(3,5-difluorophenyl)ethyl)-2-(5-hydroxy-1H-indol-3-yl)acetamide (24)

The title compound was prepared according to the method presented for the synthesis of compound 5F of Example 5 utilizing 19E and 2-(5-hydroxy-1H-indol-3-yl)acetic acid. $^1$H NMR (400 MHz, CDCl$_3$) δ 8.06 (s, 1H), 7.81 (d, J=8.3 Hz, 2H), 7.41 (d, J=8.5 Hz, 2H), 7.27 (m, 1H), 7.08 (s, 1H), 6.87-6.76 (m, 2H), 6.60 (m, 1H), 6.47 (d, J=6.0 Hz, 2H), 6.30 (s, 1H), 5.26 (d, J=7.9 Hz, 1H), 3.67 (s, 2H), 3.08-2.93 (m, 2H). MS (m/z) 508.1 [M+H]+.

EXAMPLE 25

-continued

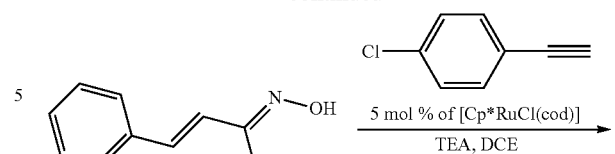

-continued

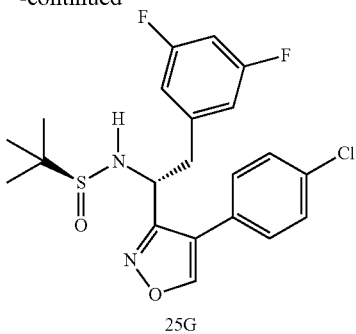

25G

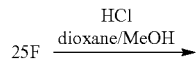

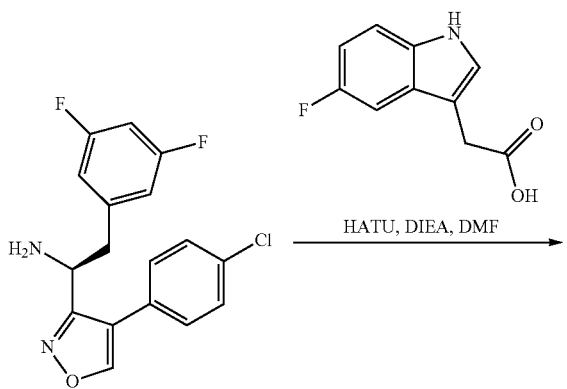

25I

Synthesis of (Z)-N-hydroxycinnamimidoyl chloride (25B)

To a stirred solution of cinnamaldoxime (10 g, 68 mmol) in DMF (100 mL) at room temperature was added solid NCS (9.08 g, 68 mmol). The suspension was stirred at room temperature overnight. The reaction mixture was poured into ice-water, extracted with a mixture of ethyl acetate and hexanes (7:3, 3×), dried with Na$_2$SO$_4$, concentrated and dried in vacuum to give the title compound.

Synthesis of (E)-4-(4-chlorophenyl)-3-styrylisoxazole (25C)

A screw-top Schlenk flask (250 mL) purged with dry nitrogen was charged with compound 25B (7.31 g, 40 mmol) and 4-chlorophenylacetylene (5.0 g, 36.6 mmol). At room temperature, degassed 1,2-dichloroethane (100 mL) was added followed by [Cp*RuCl(cod)] (450 mg, 1.18 mmol) and triethylamine (6.38 mL, 45.8 mmol). The flask was purged with N$_2$ and capped. After being stirred at room temperature for 7 h, the reaction mixture was passed through a plug of silica gel, and washed with DCM. The resulting solution was concentrated and the residue was purified by column chromatography on silica gel (pure hexanes to 10:1 hexanes/EtOAc) to provide the desired compound. MS (m/z) 282.0 [M+H]$^+$.

Synthesis of 4-(4-chlorophenyl)isoxazole-3-carbaldehyde (25D)

(E)-4-(4-Chlorophenyl)-3-styrylisoxazole (2 g, 7.1 mmol) was dissolved in DCM/MeOH (20 mL/2 mL) and cooled to −78° C. The reaction was placed under ozonolysis conditions (O$_3$ bubbling) until full disappearance of starting material. DMS (8 mL) was added and the reaction was let warm to ambient temperature. After 15 h, the reaction was partitioned between EtOAc and H$_2$O. The organics were separated, washed with saturated aqueous NaHCO$_3$, and dried with saturated aqueous NaCl. Solvents were removed in vacuo and the residue purified by column chromatography on silica to provide the desired product: MS (m/z) 208.0 [M+H]$^+$.

Synthesis of (S,E)-N-((4-(4-chlorophenyl)isoxazol-3-yl)methylene)-2-methylpropane-2-sulfinamide (25E)

The title compound was prepared according to the method presented in Example 5 substituting 4-(4-chlorophenyl)isoxazole-3-carbaldehyde for 5A to provide the desired compound: MS (m/z) 311.0 [M+H]$^+$.

Synthesis of (S)-N-((S)-1-(4-(4-chlorophenyl)isoxazol-3-yl)-2-(3,5-difluorophenyl)ethyl)-2-methylpropane-2-sulfinamide and (S)-N-((R)-1-(4-(4-chlorophenyl)isoxazol-3-yl)-2-(3,5-difluorophenyl)ethyl)-2-methylpropane-2-sulfinamide (25F and 25G)

The title compounds were prepared according to the method presented in Example 5 substituting 25E for 5B to provide the desired compounds: MS (m/z) (25F) 439.8 and (25G) 439.8 [M+H]$^+$.

Synthesis of (S)-1-(4-(4-chlorophenyl)isoxazol-3-yl)-2-(3,5-difluorophenyl)ethanamine (25H)

The title compound was prepared according to the method presented in Example 5 substituting 25F for 5D to provide the desired compound: MS (m/z) 335.7 [M+H]$^+$.

Synthesis of (S)-N-(1-(4-(4-chlorophenyl)isoxazol-3-yl)-2-(3,5-difluorophenyl)ethyl)-2-(5-fluoro-1H-indol-3-yl)acetamide (25I)

The title compound was prepared according to the method presented in the synthesis of 5 substituting 2-(5-fluoro-1H-indol-3-yl)acetic acid for 2-(5-(trifluoromethyl)-1H-indol-3-yl)acetic acid and 25H for 5E to provide the desired compound. $^1$H NMR (400 MHz, DMSO) δ 10.88 (s, 1H), 9.06 (s, 1H), 8.72 (d, 1H), 7.26 (dd, 3H), 7.12-7.02 (m, 2H), 6.95-6.79

(m, 2H), 6.73 (d, 2H), 5.29 (dd, 1H), 3.35 (s, 2H), 3.18-2.99 (m, 2H); MS (m/z) 511.1 [M+H]+.

EXAMPLE 26

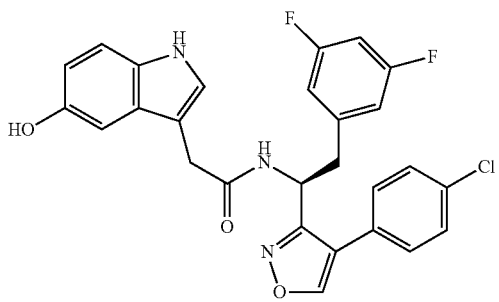

26

Synthesis of (S)-N-(1-(4-(4-chlorophenyl)isoxazol-3-yl)-2-(3,5-difluorophenyl)ethyl)-2-(5-hydroxy-1H-indol-3-yl)acetamide (26)

The title compound was prepared according to the method presented in the synthesis of 19F substituting 2-(5-hydroxy-1H-indol-3-yl)acetic acid for 2-(5-(trifluoromethyl)-1H-indol-3-yl)acetic acid and (S)-1-(4-(4-chlorophenyl)isoxazol-3-yl)-2-(3,5-difluorophenyl)ethanamine for 19E to provide the desired compound (26): 1H NMR (400 MHz, DMSO) δ 10.46 (s, 1H), 9.04 (s, 1H), 8.65 (d, 1H), 7.35-7.20 (m, 3H), 7.06 (d, 1H), 6.92 (t, 1H), 6.87 (d, 1H), 6.77 (d, 1H), 6.71 (d, 2H), 6.54 (dd, 1H), 5.25 (q, 1H), 3.39-3.25 (m, 2H), 3.08 (d, 2H); MS (m/z) 508.8 [M+H]+.

EXAMPLE 27

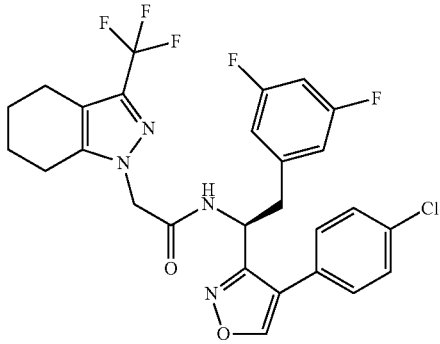

27

Synthesis of (S)-N-(1-(4-(4-chlorophenyl)isoxazol-3-yl)-2-(3,5-difluorophenyl)ethyl)-2-(3-(trifluoromethyl)-4,5,6,7-tetrahydro-1H-indazol-1-yl)acetamide (27)

The title compound was prepared according to the method presented in the synthesis of 19F substituting 2-(3-(trifluoromethyl)-4,5,6,7-tetrahydro-1H-indazol-1-yl)acetic acid for 2-(5-(trifluoromethyl)-1H-indol-3-yl)acetic acid and (S)-1-(4-(4-chlorophenyl)isoxazol-3-yl)-2-(3,5-difluorophenyl)ethanamine for 19E to provide the desired compound (27): 1H NMR (400 MHz, DMSO) δ 9.10 (s, 1H), 8.99 (d, 1H), 7.41 (d, 2H), 7.35 (d, 2H), 6.98 (d, 1H), 6.80 (d, 2H), 5.36 (d, 1H), 4.58 (s, 2H), 3.12 (dt, 2H), 2.46 (dd, 2H), 2.22 (d, 2H), 1.61 (s, 4H); MS (m/z) 566.3 [M+H]+.

EXAMPLE 28

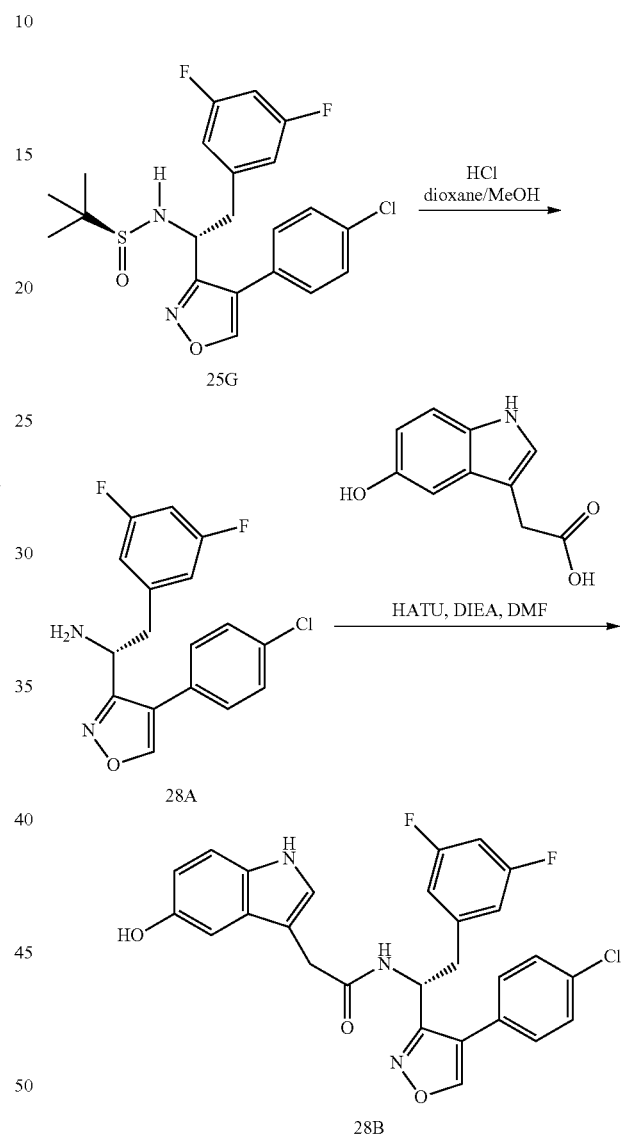

Synthesis of (R)-1-(4-(4-chlorophenyl)isoxazol-3-yl)-2-(3,5-difluorophenyl)ethanamine (28A)

The title compound was prepared according to the method presented in Example 5 substituting 25G for 5D to provide the desired compound: MS (m/z) 335.7 [M+H]+.

Synthesis of (R)-N-(1-(4-(4-chlorophenyl)isoxazol-3-yl)-2-(3,5-difluorophenyl)ethyl)-2-(5-hydroxy-1H-indol-3-yl)acetamide (28B)

The title compound was prepared according to the method presented in the synthesis of 5F substituting 2-(5-hydroxy- 1H-indol-3-yl)acetic acid for 2-(5-(trifluoromethyl)-1H-indol-3-yl)acetic acid and 28A for 5E to provide the desired compound (28B): $^1$H NMR (400 MHz, DMSO) δ 10.46 (s, 1H), 9.04 (s, 1H), 8.65 (d, 1H), 7.32-7.20 (m, 3H), 7.06 (d, 1H), 6.95-6.83 (m, 2H), 6.74 (dd, 3H), 6.54 (dd, 1H), 5.25 (q, 1H), 3.41-3.25 (m, 2H), 3.08 (d, 2H); MS (m/z) 509.1 [M+H]$^+$.

EXAMPLE 29

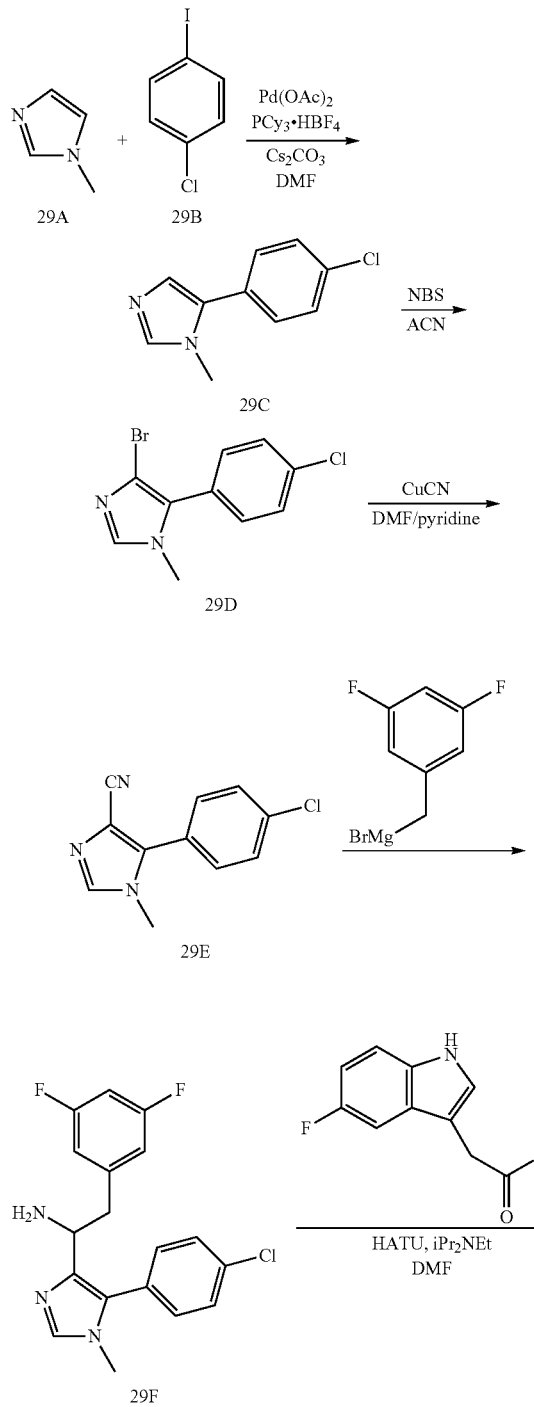

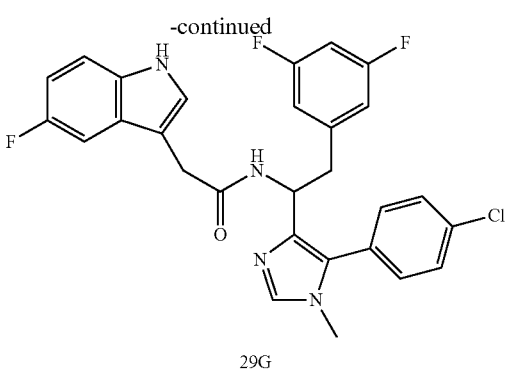

Synthesis of 5-(4-chlorophenyl)-1-methyl-1H-imidazole (29C)

1-Chloro-4-iodobenzene (10 g, 42 mmol) was combined with 1-methyl-1H-imidazole (13.3 mL, 168 mmol), Pd(OAc)$_2$ (470 mg), PCy$_3$·HBF$_4$ (1.54 g), Cs$_2$CO$_3$ (13.7 g, 42 mmol) in DMF (200 mL). The reaction was heated to 120° C. for 15 hr. After cooling to ambient temperature, the reaction was filtered to remove solids and the eluent was partitioned between EtOAc and H$_2$O. The organics were separated, washed with saturated aqueous NaHCO$_3$, and dried with saturated aqueous NaCl. Solvents were removed in vacuo and the residue purified by column chromatography on silica to provide the desired product. MS (m/z) 193.3 [M+H]$^+$.

Synthesis of 4-bromo-5-(4-chlorophenyl)-1-methyl-1H-imidazole (29D)

(4-Chlorophenyl)-1-methyl-1H-imidazole (3 g, 15.5 mmol) was dissolved in ACN (150 mL) and cooled to 0° C. NBS (2.76 g, 15.5 mmol) was added in 3 portions over 5 min. The reaction was stirred at 0° C. for 20 min then let warm to ambient temperature. Solvents were removed in vacuo and the residue partitioned between EtOAc and 20% aqueous KH$_2$PO$_4$. The organics were separated, washed with saturated aqueous NaHCO$_3$, and dried with saturated aqueous NaCl. Solvents were removed in vacuo and the residue purified by column chromatography on silica to provide the desired product. MS (m/z) 273.1 [M+H]$^+$.

Synthesis of 5-(4-chlorophenyl)-1-methyl-1H-imidazole-4-carbonitrile (29E)

To 4-bromo-5-(4-chlorophenyl)-1-methyl-1H-imidazole (1.3 g, 4.79 mmol) in DMF (8.4 mL) and pyridine (1.6 mL) was added CuCN (1.3 g, 14.4 mmol). The reaction was heated in a microwave reactor at 200° C. for 35 min. After cooling to ambient temperature, the reaction was quenched by addition of a 3:1 solution of NH$_4$OH/saturated aqueous NH$_4$Cl (60 mL). The reaction was extracted with EtOAc, organics separated, washed with saturated aqueous NaHCO$_3$, and dried with saturated aqueous NaCl. Solvents were removed in vacuo and the residue purified by column chromatography on silica to provide desired product and recovered starting material. The recovered starting material was resubjected to the reaction conditions and purified as above to provide additional desired product. MS (m/z) 218.3 [M+H]$^+$.

Synthesis of 1-(5-(4-chlorophenyl)-1-methyl-1H-imidazol-4-yl)-2-(3,5-difluorophenyl)ethanamine (29F)

To a solution of 5-(4-chlorophenyl)-1-methyl-1H-imidazole-4-carbonitrile (520 mg, 2.4 mmol) in toluene (13 mL) at 0° C. was added (3,5-difluorobenzyl)magnesium bromide (12.5 mL of a 0.25 M solution in diethylether). The reaction was stirred 20 min at 0° C. then let warm to ambient temperature. After stirring for 40 min, the reaction was cooled to 0° C. 2-Butanol (8 mL) and MeOH (4 mL) were added followed by addition of NaBH$_4$ (135 mg, 3.6 mmol) and stirred for 20 min. The reaction was quenched by addition of saturated aqueous NH$_4$Cl and extracted with EtOAc. The organics were separated, washed with saturated aqueous NaHCO$_3$, and dried with saturated aqueous NaCl. Solvents were removed in vacuo and the residue purified by column chromatography on silica to provide the desired product. MS (m/z) 348.3 [M+H]$^+$.

Synthesis of N-(1-(5-(4-chlorophenyl)-1-methyl-1H-imidazol-4-yl)-2-(3,5-difluorophenyl)ethyl)-2-(5-fluoro-1H-indol-3-yl)acetamide (29G)

The title compound as prepared according to the method presented in the synthesis of Example 1 utilizing 29F and 2-(5-fluoro-1H-indol-3-yl)acetic acid. $^1$H NMR (400 MHz, DMSO-d$_6$) δ 10.94 (d, 1H), 8.78 (s, 1H), 8.42 (d, 1H), 7.49-7.42 (m, 2H), 7.32-7.20 (m, 3H), 7.17-7.06 (m, 2H), 6.99-6.80 (m, 2H), 6.69-6.60 (m, 2H), 4.87 (q, 1H), 3.49 (s, 3H), 3.41 (d, 2H), 3.08 (dd, 1H), 2.94 (dd, 1H); MS (m/z) 523.3 [M+H]$^+$.

EXAMPLE 30

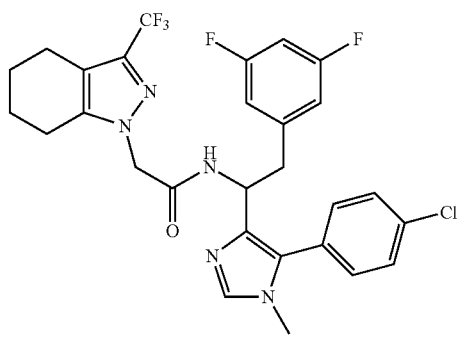

Synthesis of N-(1-(5-(4-chlorophenyl)-1-methyl-1H-imidazol-4-yl)-2-(3,5-difluorophenyl)ethyl)-2-(3-(trifluoromethyl)-4,5,6,7-tetrahydro-1H-indazol-1-yl)acetamide (30)

The title compound as prepared according to the method presented in the synthesis of Example 1 utilizing 29F and 2-(3-(trifluoromethyl)-4,5,6,7-tetrahydro-1H-indazol-1-yl) acetic acid. MS (m/z) 579.0 [M+H]$^+$.

EXAMPLE 31

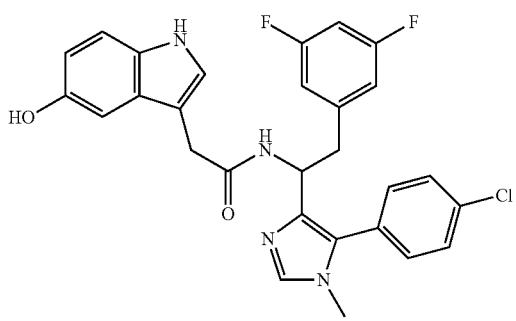

Synthesis of N-(1-(5-(4-chlorophenyl)-1-methyl-1H-imidazol-4-yl)-2-(3,5-difluorophenyl)ethyl)-2-(5-hydroxy-1H-indol-3-yl)acetamide (31)

The title compound as prepared according to the method presented in the synthesis of Example 1 utilizing 29F and 2-(5-hydroxy-1H-indol-3-yl)acetic acid. $^1$H NMR (400 MHz, DMSO-d$_6$) δ 10.52 (s, 1H), 8.26 (s, 1H), 7.43 (s, 2H), 7.18 (d, 2H), 7.08 (d1H), 6.99-6.92 (m, 2H), 6.73 (s, 1H), 6.64-6.52 (m, 3H), 4.85 (d, 1H), 3.47 (s, 3H), 3.10-3.01 (m, 1H), 2.99-2.88 (m, 1H); MS (m/z) 521.7 [M+H]$^+$.

EXAMPLE 32

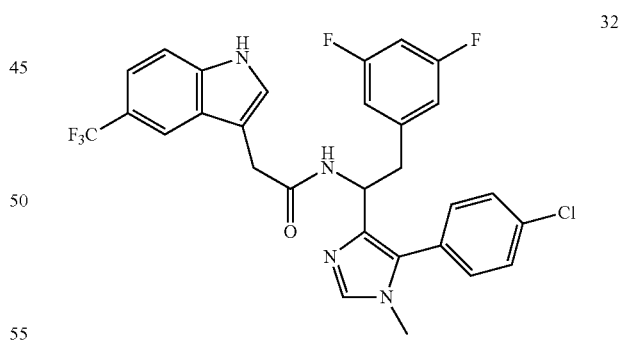

Synthesis of N-(1-(5-(4-chlorophenyl)-1-methyl-1H-imidazol-4-yl)-2-(3,5-difluorophenyl)ethyl)-2-(5-(trifluoromethyl)-1H-indol-3-yl)acetamide (32)

The title compound as prepared according to the method presented in the synthesis of Example 1 utilizing 29F and 2-(5-(trifluoromethyl)-1H-indol-3-yl)acetic acid. $^1$H NMR (400 MHz, DMSO-d$_6$) δ 11.31 (s, 1H), 8.52 (d, 1H), 7.81 (d, 1H), 7.46 (dd, J 2H), 7.35-7.17 (m, 3H), 6.96-6.86 (m, 1H), 6.66-6.59 (m, 2H), 4.87 (q, 1H), 3.49 (s, 3H), 3.07 (dd, 1H), 2.94 (dd, 1H); MS (m/z) 573.9 [M+H]⁺.

EXAMPLE 33

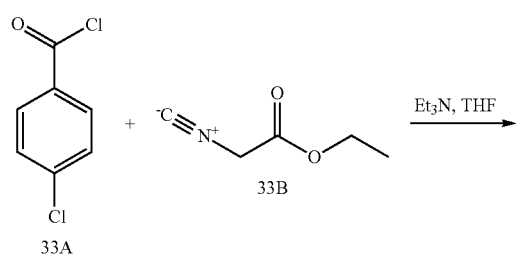

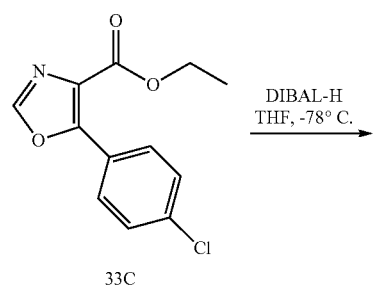

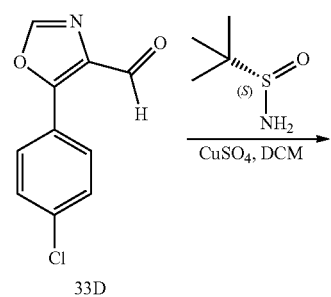

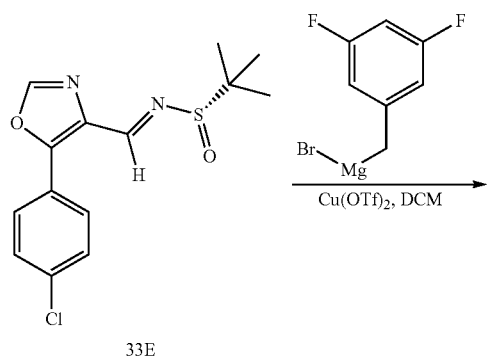

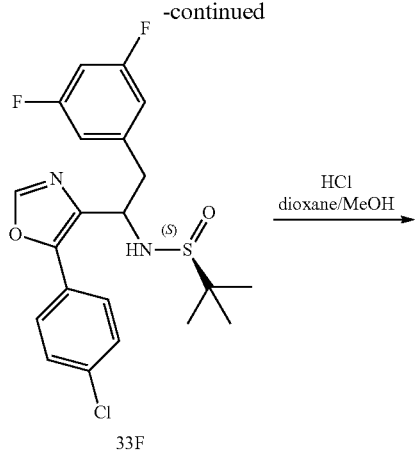

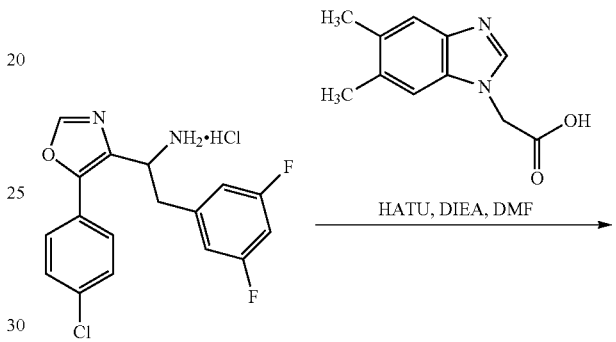

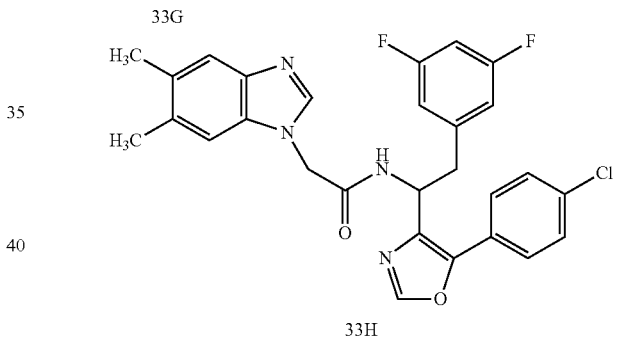

Synthesis of ethyl 5-(4-chlorophenyl)oxazole-4-carboxylate (33C)

Triethylamine (20 mL, 144 mmol) was added to a solution of 4-chlorobenzoyl chloride (8.4 g, 48 mmol) in THF (100 mL) at 0° C. Ethyl 2-isocyanoacetate (6.0 g, 53 mmol) was added dropwise and the resulting solution was stirred at room temperature for 1 h. The reaction mixture was partitioned between EtOAc and water. The organic phase was washed with brine, dried over Na₂SO₄, filtered and concentrated in vacuo. The residue was purified by silica column with ethyl acetate and hexanes as eluents to give the desired compound. MS (m/z) 252.1 [M+H]⁺.

Synthesis of 5-(4-chlorophenyl)oxazole-4-carbaldehyde (33D)

To a solution of 33C (1.25 g, 5 mmol) in THF was added DIBAL-H (1.0 M in toluene, 10 mmol) dropwise at −70° C. The resulting solution was allowed to warm to −20° C. over 3 h. Upon completion of the reaction, saturated aqueous NH₄Cl was added to the flask and the mixture was partitioned between EtOAc and water. The organic phase was washed with brine, dried over Na₂SO₄, filtered and concentrated in vacuo. The crude product was used in the next step without further purification. MS (m/z) 208.1 [M+H]⁺.

Synthesis of (E)-N-((5-(4-chlorophenyl)oxazol-4-yl) methylene)-2-methylpropane-2-sulfinamide (33E)

The title compound was prepared according to the method presented for the synthesis of compound 5B of Example 5 utilizing 33D and (S)-2-methylpropane-2-sulfinamide. MS (m/z) 311.2 [M+H]⁺.

Synthesis of N-(1-(5-(4-chlorophenyl)oxazol-4-yl)-2-(3,5-difluorophenyl)ethyl)-2-methylpropane-2-sulfinamide (33F)

The title compound was prepared as a mixture of diastereomers according to the method presented for the synthesis of compound 5C and 5D of Example 5 utilizing 33E and (3,5-difluorobenzyl)magnesium bromide. MS (m/z) 438.9 [M+H]⁺.

Synthesis of 1-(5-(4-chlorophenyl)oxazol-4-yl)-2-(3,5-difluorophenyl)ethanamine hydrochloride (33G)

The title compound was prepared according to the method presented for the synthesis of compound 5E of Example 5 utilizing 33F. MS (m/z) 335.1 [M+H]⁺.

Synthesis of N-(1-(5-(4-chlorophenyl)oxazol-4-yl)-2-(3,5-difluorophenyl)ethyl)-2-(5,6-dimethyl-1H-benzo[d]imidazol-1-yl)acetamide (33H)

The title compound was prepared according to the method presented for the synthesis of compound 5F of Example 5 utilizing 33G and 2-(5,6-dimethyl-1H-benzo[d]imidazol-1-yl)acetic acid. ¹H NMR (400 MHz, dmso) δ 9.36 (d, J=8.3 Hz, 1H), 9.11 (s, 1H), 8.55 (s, 1H), 7.63-7.53 (m, 3H), 7.45 (d, J=8.3 Hz, 2H), 7.20 (s, 1H), 6.98 (d, J=8.7 Hz, 1H), 6.88 (d, J=7.2 Hz, 2H), 5.36 (d, J=7.5 Hz, 1H), 5.17-5.01 (m, 2H), 3.27-3.10 (m, 2H), 2.35 (s, 3H), 2.29 (s, 3H). MS (m/z) 521.1 [M+H]⁺.

EXAMPLE 34

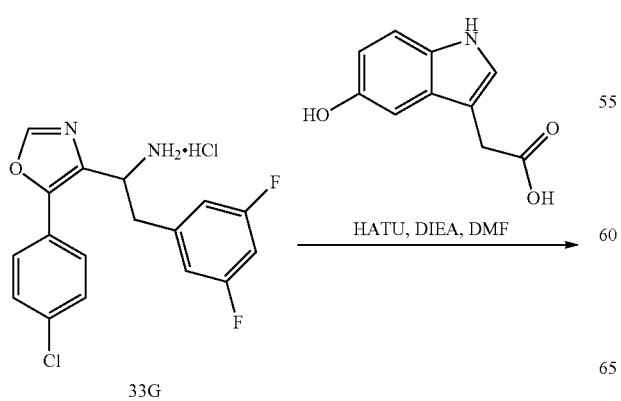

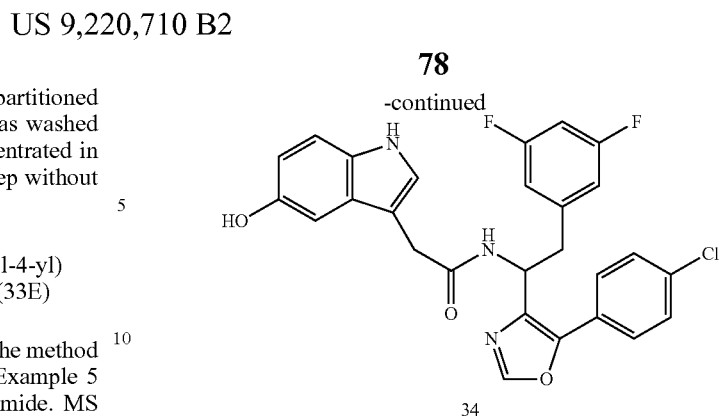

Synthesis of N-(1-(5-(4-chlorophenyl)oxazol-4-yl)-2-(3,5-difluorophenyl)ethyl)-2-(5-hydroxy-1H-indol-3-yl)acetamide (34)

The title compound was prepared according to the method presented for the synthesis of compound 5F of Example 5 utilizing 33G and 2-(5-hydroxy-1H-indol-3-yl)acetic acid. ¹H NMR (400 MHz, DMSO) δ 10.46 (s, 1H), 8.63 (d, J=8.0 Hz, 1H), 8.45 (s, 1H), 7.59 (d, J=8.4 Hz, 2H), 7.43 (d, J=8.5 Hz, 2H), 7.07 (d, J=8.6 Hz, 1H), 7.00-6.84 (m, 2H), 6.79 (d, J=8.4 Hz, 3H), 6.55 (d, J=8.7 Hz, 1H), 5.28 (q, J=7.8 Hz, 1H), 3.39 (s, 2H), 3.10 (m, 2H). MS (m/z) 508.1 [M+H]⁺.

EXAMPLE 35

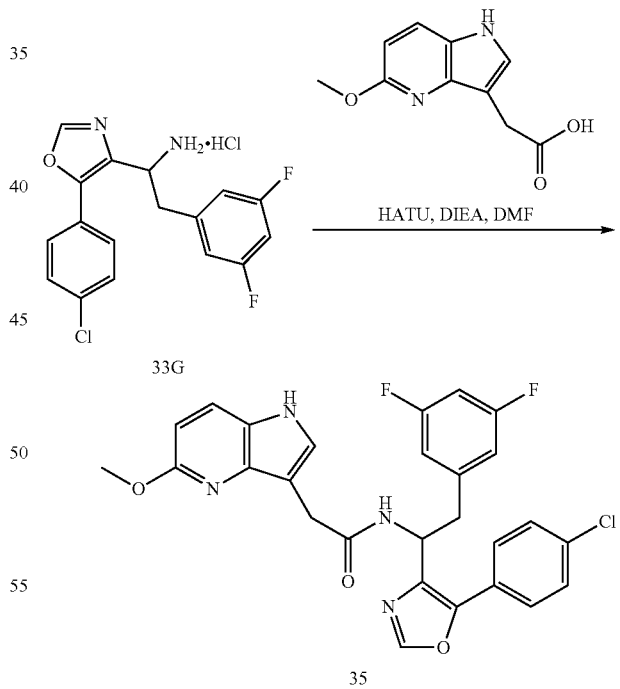

Synthesis of N-(1-(5-(4-chlorophenyl)oxazol-4-yl)-2-(3,5-difluorophenyl)ethyl)-2-(5-methoxy-1H-pyrrolo[3,2-b]pyridin-3-yl)acetamide (35)

The title compound was prepared according to the method presented for the synthesis of compound 5F of Example 5 utilizing 33G and 2-(5-methoxy-1H-pyrrolo[3,2-b]pyridin-3-yl)acetic acid. ¹H NMR (400 MHz, DMSO) δ 11.13 (s, 1H), 8.65 (d, J=8.6 Hz, 1H), 8.46 (s, 1H), 7.74 (m, 1H), 7.62 (m, 2H), 7.47 (d, J=8.5 Hz, 2H), 7.27 (s, 1H), 6.89 (t, J=9.6 Hz, 1H), 6.74 (d, J=6.8 Hz, 2H), 6.60 (d, J=8.6 Hz, 1H), 5.35 (q, J=7.8 Hz, 1H), 3.87 (s, 3H), 3.50 (s, 2H), 3.17-2.98 (m, 2H). MS (m/z) 523.1 [M+H]⁺.

EXAMPLE 36

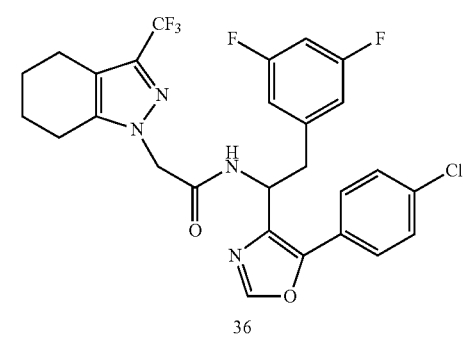

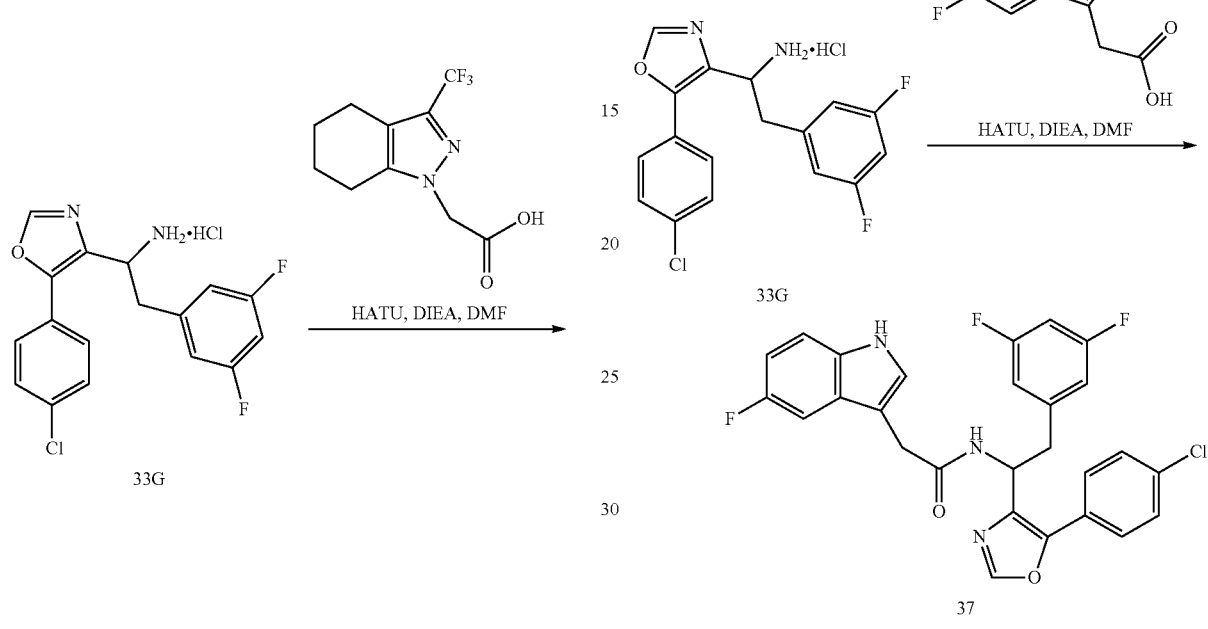

EXAMPLE 37

Synthesis of N-(1-(5-(4-chlorophenyl)oxazol-4-yl)-2-(3,5-difluorophenyl)ethyl)-2-(5-fluoro-1H-indol-3-yl)acetamide (37)

The title compound was prepared according to the method presented for the synthesis of compound 5F of Example 5 utilizing 33G and 2-(5-fluoro-1H-indol-3-yl)acetic acid. ¹H NMR (400 MHz, DMSO) δ 10.88 (s, 1H), 8.76 (d, J=8.3 Hz, 1H), 8.47 (s, 1H), 7.63 (d, J=7.9 Hz, 2H), 7.43 (d, J=8.0 Hz, 2H), 7.26 (dd, J=8.8, 4.6 Hz, 1H), 7.08 (d, J=12.4 Hz, 2H), 6.91-6.83 (m, 4H), 5.31 (d, J=7.9 Hz, 1H), 3.44 (s, 2H), 3.22-3.11 (m, 1H), 3.06 (dd, J=13.3, 7.0 Hz, 1H). MS (m/z) 510.1 [M+H]⁺.

Synthesis of N-(1-(5-(4-chlorophenyl)oxazol-4-yl)-2-(3,5-difluorophenyl)ethyl)-2-(3-(trifluoromethyl)-4,5,6,7-tetrahydro-1H-indazol-1-yl)acetamide (36)

The title compound was prepared according to the method presented for the synthesis of compound 5F of Example 5 utilizing 33G and 2-(3-(trifluoromethyl)-4,5,6,7-tetrahydro-1H-indazol-1-yl)acetic acid. ¹H NMR (400 MHz, DMSO) δ 9.07 (d, J=8.1 Hz, 1H), 8.51 (s, 1H), 7.62 (d, J=8.4 Hz, 2H), 7.50 (d, J=8.4 Hz, 2H), 6.98 (t, J=9.6 Hz, 1H), 6.87 (d, J=7.6 Hz, 2H), 5.41-5.30 (m, 1H), 4.80-4.64 (m, 2H), 3.35 (s, 2H), 3.25-3.12 (m, 1H), 3.07 (dd, J=13.4, 6.8 Hz, 1H), 2.33 (s, 1H), 2.23 (s, 1H), 1.63 (s, 4H). MS (m/z) 565.1 [M+H]⁺.

EXAMPLE 38

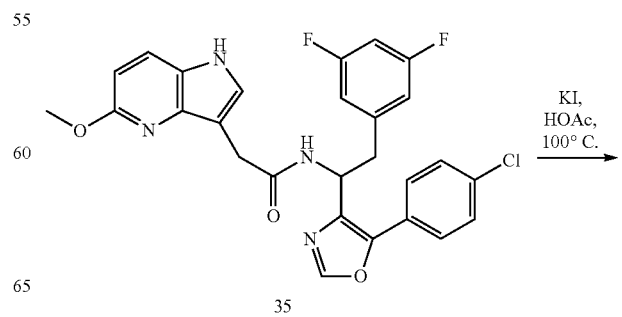

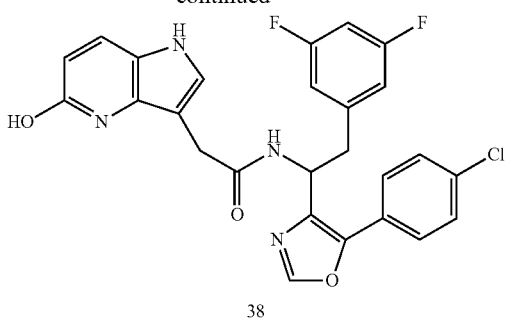

38

Synthesis of N-(1-(5-(4-chlorophenyl)oxazol-4-yl)-2-(3,5-difluorophenyl)ethyl)-2-(5-hydroxy-1H-pyrrolo[3,2-b]pyridin-3-yl)acetamide (38)

The title compound was prepared according to the method presented for the synthesis of compound 22 of Example 22 utilizing 35. $^1$H NMR (400 MHz, DMSO) δ 11.32 (s, 1H), 8.71 (d, J=8.0 Hz, 1H), 8.59 (s, 1H), 8.50 (s, 1H), 7.74 (d, J=9.0 Hz, 1H), 7.59 (dd, J=25.7, 8.2 Hz, 2H), 7.43 (dd, J=26.5, 8.2 Hz, 2H), 7.07 (s, 1H), 6.86 (s, 1H), 6.77 (d, J=7.5 Hz, 2H), 6.23 (d, J=9.2 Hz, 1H), 5.32 (d, J=7.7 Hz, 1H), 3.41 (s, 2H), 3.23-3.04 (m, 2H). MS (m/z) 509.1 [M+H]$^+$.

EXAMPLE 39

The following illustrate representative pharmaceutical dosage forms, containing a compound of formula I ('Compound X'), for therapeutic or prophylactic use in humans.

| (i) Tablet 1 | mg/tablet |
|---|---|
| Compound X = | 100.0 |
| Lactose | 77.5 |
| Povidone | 15.0 |
| Croscarmellose sodium | 12.0 |
| Microcrystalline cellulose | 92.5 |
| Magnesium stearate | 3.0 |
| | 300.0 |

| (ii) Tablet 2 | mg/tablet |
|---|---|
| Compound X = | 20.0 |
| Microcrystalline cellulose | 410.0 |
| Starch | 50.0 |
| Sodium starch glycolate | 15.0 |
| Magnesium stearate | 5.0 |
| | 500.0 |

| (iii) Capsule | mg/capsule |
|---|---|
| Compound X = | 10.0 |
| Colloidal silicon dioxide | 1.5 |
| Lactose | 465.5 |
| Pregelatinized starch | 120.0 |
| Magnesium stearate | 3.0 |
| | 600.0 |

| (iv) Injection 1 (1 mg/ml) | mg/ml |
|---|---|
| Compound X = (free acid form) | 1.0 |
| Dibasic sodium phosphate | 12.0 |
| Monobasic sodium phosphate | 0.7 |
| Sodium chloride | 4.5 |
| 1.0N Sodium hydroxide solution (pH adjustment to 7.0-7.5) | q.s. |
| Water for injection | q.s. ad 1 mL |

| (v) Injection 2 (10 mg/ml) | mg/ml |
|---|---|
| Compound X = (free acid form) | 10.0 |
| Monobasic sodium phosphate | 0.3 |
| Dibasic sodium phosphate | 1.1 |
| Polyethylene glycol 400 | 200.0 |
| 1.0N Sodium hydroxide solution (pH adjustment to 7.0-7.5) | q.s. |
| Water for injection | q.s. ad 1 mL |

| (vi) Aerosol | mg/can |
|---|---|
| Compound X = | 20.0 |
| Oleic acid | 10.0 |
| Trichloromonofluoromethane | 5,000.0 |
| Dichlorodifluoromethane | 10,000.0 |
| Dichlorotetrafluoroethane | 5,000.0 |

The above formulations may be obtained by conventional procedures well known in the pharmaceutical art.

All references, including publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

The use of the terms "a" and "an" and "the" and similar references in the context of this disclosure (especially in the context of the following claims) are to be construed to cover both the singular and the plural, unless otherwise indicated herein or clearly contradicted by context. All methods described herein can be performed in any suitable order unless otherwise indicated herein or otherwise clearly contradicted by context. The use of any and all examples, or exemplary language (e.g., such as, preferred, preferably) provided herein, is intended merely to further illustrate the content of the disclosure and does not pose a limitation on the scope of the claims. No language in the specification should be construed as indicating any non-claimed element as essential to the practice of the present disclosure.

Alternative embodiments of the claimed disclosure are described herein, including the best mode known to the inventors for practicing the claimed invention. Of these, variations of the disclosed embodiments will become apparent to those of ordinary skill in the art upon reading the foregoing disclosure. The inventors expect skilled artisans to employ such variations as appropriate (e.g., altering or combining features or embodiments), and the inventors intend for the invention to be practiced otherwise than as specifically described herein.

Accordingly, this invention includes all modifications and equivalents of the subject matter recited in the claims appended hereto as permitted by applicable law. Moreover, any combination of the above described elements in all possible variations thereof is encompassed by the invention unless otherwise indicated herein or otherwise clearly contradicted by context.

The use of individual numerical values is stated as approximations as though the values were preceded by the word "about" or "approximately." Similarly, the numerical values in the various ranges specified in this application, unless expressly indicated otherwise, are stated as approximations as though the minimum and maximum values within the stated ranges were both preceded by the word "about" or "approximately." In this manner, variations above and below the stated ranges can be used to achieve substantially the same results as values within the ranges. As used herein, the terms "about" and "approximately" when referring to a numerical value shall have their plain and ordinary meanings to a person of ordinary skill in the art to which the disclosed subject matter is most closely related or the art relevant to the range or element at issue. The amount of broadening from the strict numerical boundary depends upon many factors. For example, some of the factors which may be considered include the criticality of the element and/or the effect a given amount of variation will have on the performance of the claimed subject matter, as well as other considerations known to those of skill in the art. As used herein, the use of differing amounts of significant digits for different numerical values is not meant to limit how the use of the words "about" or "approximately" will serve to broaden a particular numerical value or range. Thus, as a general matter, "about" or "approximately" broaden the numerical value. Also, the disclosure of ranges is intended as a continuous range including every value between the minimum and maximum values plus the broadening of the range afforded by the use of the term "about" or "approximately." Thus, recitation of ranges of values herein are merely intended to serve as a shorthand method of referring individually to each separate value falling within the range, unless otherwise indicated herein, and each separate value is incorporated into the specification as if it were individually recited herein.

It is to be understood that any ranges, ratios and ranges of ratios that can be formed by, or derived from, any of the data disclosed herein represent further embodiments of the present disclosure and are included as part of the disclosure as though they were explicitly set forth. This includes ranges that can be formed that do or do not include a finite upper and/or lower boundary. Accordingly, a person of ordinary skill in the art most closely related to a particular range, ratio or range of ratios will appreciate that such values are unambiguously derivable from the data presented herein.

What is claimed is:

1. A compound of formula I:

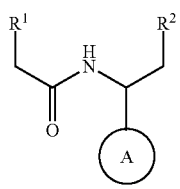

wherein:
A is a 5-membered N-heteroaryl, wherein the 5-membered N-heteroaryl is substituted with one $Z^1$ group and optionally substituted with 1, 2, or 3 $Z^2$ groups;
$R^1$ is a bicyclic-heteroaryl or tricyclic heteroaryl, wherein the bicyclic-heteroaryl has 4 to 12 carbon atoms and 1-5 heteroatoms, and wherein any bicyclic-heteroaryl of $R^1$ is optionally substituted with 1, 2, 3, 4, or 5 $Z^3$ groups;
$R^2$ is a phenyl, 5-membered heteroaryl or 6-membered heteroaryl, wherein any phenyl, 5-membered heteroaryl or 6-membered heteroaryl of $R^2$ is optionally substituted with 1, 2, 3, 4 or 5 $Z^4$ groups;
$Z^1$ is selected from $(C_3-C_8)$alkyl, $(C_6-C_{20})$aryl, and aryl$(C_1-C_6)$alkyl-, wherein any aryl, and aryl$(C_1-C_6)$alkyl- of $Z^1$ is optionally substituted with 1, 2, 3, 4, or 5 $Z^{1a}$ or $Z^{1b}$ groups and wherein any $(C_3-C_8)$alkyl of $Z^1$ is optionally substituted with 1, 2, 3, 4, or 5 $Z^{1a}$ groups;

each $Z^{1a}$ is independently selected from $(C_3-C_7)$carbocycle, halogen, —CN, —$OR_{n1}$, —$OC(O)R_{p1}$, —$OC(O)NR_{q1}R_{r1}$, —$SR_{n1}$, —$S(O)R_{p1}$, —$S(O)_2OH$, —$S(O)_2R_{p1}$, —$S(O)_2NR_{q1}R_{r1}$, —$NR_{q1}R_{r1}$, —$NR_{n1}COR_{p1}$, —$NR_{n1}CO_2R_{p1}$, —$NR_{n1}CONR_{q1}R_{r1}$, —$NR_{n1}S(O)_2R_{p1}$, —$NR_{n1}S(O)_2OR_{p1}$, —$NR_{n1}S(O)_2NR_{q1}R_{r1}$, $NO_2$, —$C(O)R_{n1}$, —$C(O)OR_{n1}$ and —$C(O)NR_{q1}R_{r1}$;

each $Z^{1b}$ is independently selected from $(C_1-C_6)$alkyl and $(C_3-C_5)$carbocycle wherein any $(C_1-C_6)$alkyl and $(C_3-C_5)$carbocycle of $Z^{1b}$ is optionally substituted with 1, 2, 3, 4, or 5 halogen;

each $Z^2$ is independently selected from $(C_1-C_3)$alkyl, $(C_1-C_3)$haloalkyl, halogen and —$O(C_1-C_3)$alkyl;

each $Z^3$ is independently selected from $(C_1-C_6)$alkyl, $(C_3-C_7)$carbocycle, halogen, —CN, —$OR_{n2}$, —$OC(O)R_{p2}$, —$OC(O)NR_{q2}R_{r2}$, —$SR_{n2}$, —$S(O)R_{p2}$, —$S(O)_2OH$, —$S(O)_2R_{p2}$, —$S(O)_2NR_{q2}R_{r2}$, —$NR_{q2}R_{r2}$, —$NR_{n2}COR_{p2}$, —$NR_{n2}CO_2R_{p2}$, —$NR_{n2}CONR_{q2}R_{r2}$, —$NR_{n2}S(O)_2R_{p2}$, —$NR_{n2}S(O)_2OR_{p2}$, —$NR_{n2}S(O)_2NR_{q2}R_{r2}$, $NO_2$, —$C(O)R_{n2}$, —$C(O)OR_{n2}$ and —$C(O)NR_{q2}R_{r2}$, wherein any $(C_3-C_7)$carbocycle and $(C_1-C_6)$alkyl of $Z^3$ is optionally substituted with 1, 2, 3, 4, or 5 halogen;

each $Z^4$ is independently selected from $(C_1-C_6)$alkyl, halogen and —$OR_{n3}$, wherein any $(C_1-C_6)$alkyl of $Z^4$ is optionally substituted with 1, 2, 3, 4, or 5 halogen;

each $R_{n1}$ is independently selected from H, $(C_1-C_6)$alkyl, $(C_2-C_6)$alkenyl, $(C_2-C_6)$alkynyl and $(C_3-C_7)$carbocycle;

each $R_{p1}$ is independently selected from $(C_1-C_6)$alkyl, $(C_2-C_6)$alkenyl, $(C_2-C_6)$alkynyl and $(C_3-C_7)$carbocycle;

$R_{q1}$ and $R_{r1}$ are each independently selected from H, $(C_1-C_6)$alkyl, $(C_2-C_6)$alkenyl, $(C_2-C_6)$alkynyl and $(C_3-C_7)$carbocycle, or $R_{q1}$ and $R_{r1}$ together with the nitrogen to which they are attached form a 5, 6 or 7-membered heterocycle;

each $R_{n2}$ is independently selected from H, $(C_1-C_6)$alkyl, $(C_2-C_6)$alkenyl, $(C_2-C_6)$alkynyl and $(C_3-C_7)$carbocycle;

each $R_{p2}$ is independently selected from $(C_1-C_6)$alkyl, $(C_2-C_6)$alkenyl, $(C_2-C_6)$alkynyl and $(C_3-C_7)$carbocycle;

$R_{q2}$ and $R_{r2}$ are each independently selected from H, $(C_1-C_6)$alkyl, $(C_2-C_6)$alkenyl, $(C_2-C_6)$alkynyl and $(C_3-C_7)$carbocycle, or $R_{q2}$ and $R_{r2}$ together with the nitrogen to which they are attached form a 5, 6 or 7-membered heterocycle; and each $R_{n3}$ is independently selected from H, $(C_1-C_3)$alkyl, $(C_1-C_3)$haloalkyl, and $(C_3-C_7)$carbocycle;

or a salt thereof.

2. The compound of claim 1, or a salt thereof, wherein A is selected from imidazol-2-yl, 1,2,3-triazol-4-yl, 1,2,4-triazol-3-yl, thiazol-4-yl, thiazol-5-yl, 1,3,4-oxadiazol-2-yl, 1,2,4-oxadiazol-5-yl, oxazol-5-yl, isoxazol-3-yl, imidazol-4-yl and oxazol-4-yl, wherein imidazol-2-yl, 1,2,3-triazol-4-yl, 1,2,4-triazol-3-yl, thiazol-4-yl, thiazol-5-yl, 1,3,4-oxadiazol-2-yl, 1,2,4-oxadiazol-5-yl, oxazol-5-yl, isoxazol-3-yl, imidazol-4-yl and oxazol-4-yl are each substituted with one $Z^1$ group and optionally substituted with 1, 2, or 3 $Z^2$ groups.

3. The compound of claim 1, or a salt thereof, wherein A is:

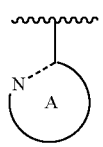

wherein the dashed bond is a single or double bond so that ring A is aromatic, A is substituted with one $Z^1$ group and optionally substituted with 1, 2, or 3 $Z^2$ groups.

4. The compound of claim 1, or a salt thereof, wherein A is:

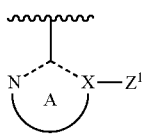

wherein the dashed bonds are single or double bonds so that ring A is aromatic, X is N or C, and wherein A is optionally substituted with 1, 2, or 3 $Z^2$ groups.

5. The compound of claim 1, or a salt thereof, wherein A is:

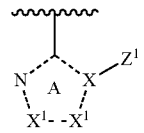

wherein X is N or C, each $X^1$ is independently selected from N, $NZ^{2a}$, O, S and $CZ^{2a}$, the dashed bonds are selected from single and double bonds so that ring A is aromatic, and $Z^{2a}$ is selected from H and $Z^2$.

6. The compound of claim 1, or a salt thereof, wherein A is selected from

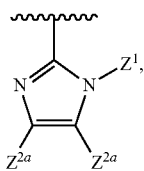 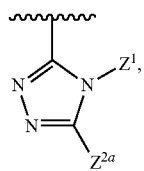 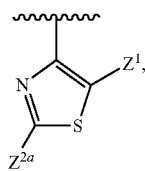

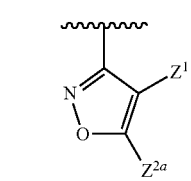 and 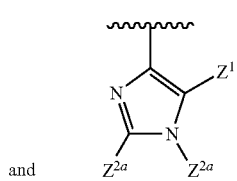

wherein each $Z^{2a}$ is independently selected from $Z^2$ and H.

7. The compound of claim 1, or a salt thereof, wherein each $Z^{1a}$ is independently selected from halogen and $-OR_{n1}$, each $Z^{1b}$ is $(C_1-C_6)$ alkyl, and wherein $R_{n1}$ is $(C_1-C_6)$alkyl.

8. The compound of claim 1, or a salt thereof, wherein A is selected from

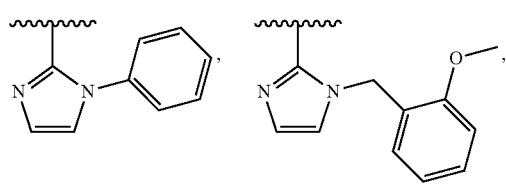

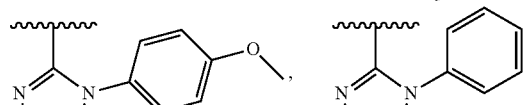

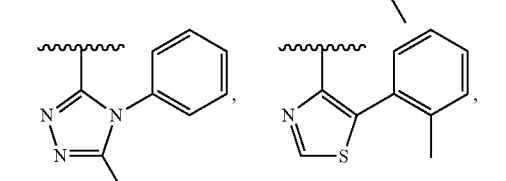

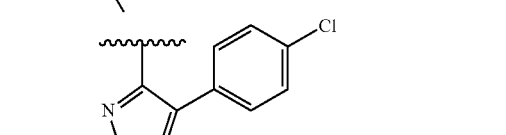

and

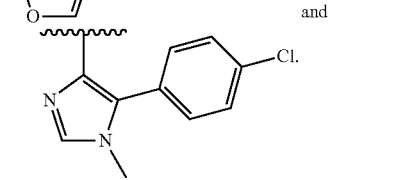

9. The compound of claim 1, or a salt thereof, wherein $R^2$ is phenyl optionally substituted with 1, 2, 3, 4, or 5 $Z^4$ groups.

10. The compound of claim 1, or a salt thereof, wherein each $Z^4$ is halogen.

11. The compound of claim 1, or a salt thereof, wherein $R^1$ is selected from indolyl, 4,5,6,7-tetrahydro-indazolyl, benzo[d]imidazolyl and pyrrolo[3,2-b]pyridinyl, wherein any indolyl, 4,5,6,7-tetrahydro-indazolyl, benzo[d]imidazolyl and pyrrolo[3,2-b]pyridinyl of $R^1$ is optionally substituted with 1, 2, 3, 4, or 5 $Z^3$ groups.

12. The compound of claim 1, or a salt thereof, wherein each $Z^3$ is independently selected from fluoro, hydroxy, trifluoromethyl, methyl and methoxy.

13. The compound of claim 1, or a salt thereof, wherein $R^1$ is selected from:

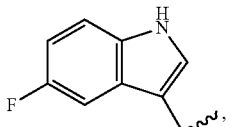 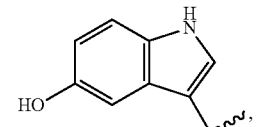

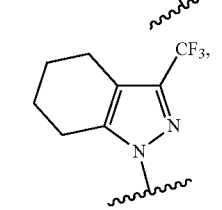 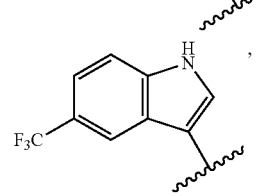

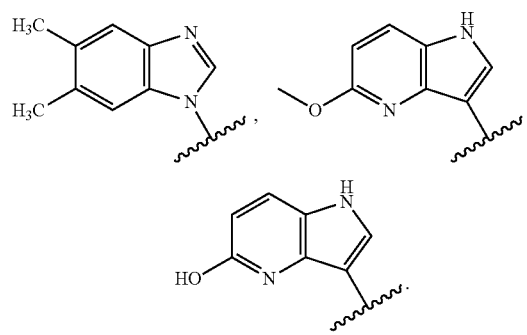
14. The compound of claim 1 selected from:
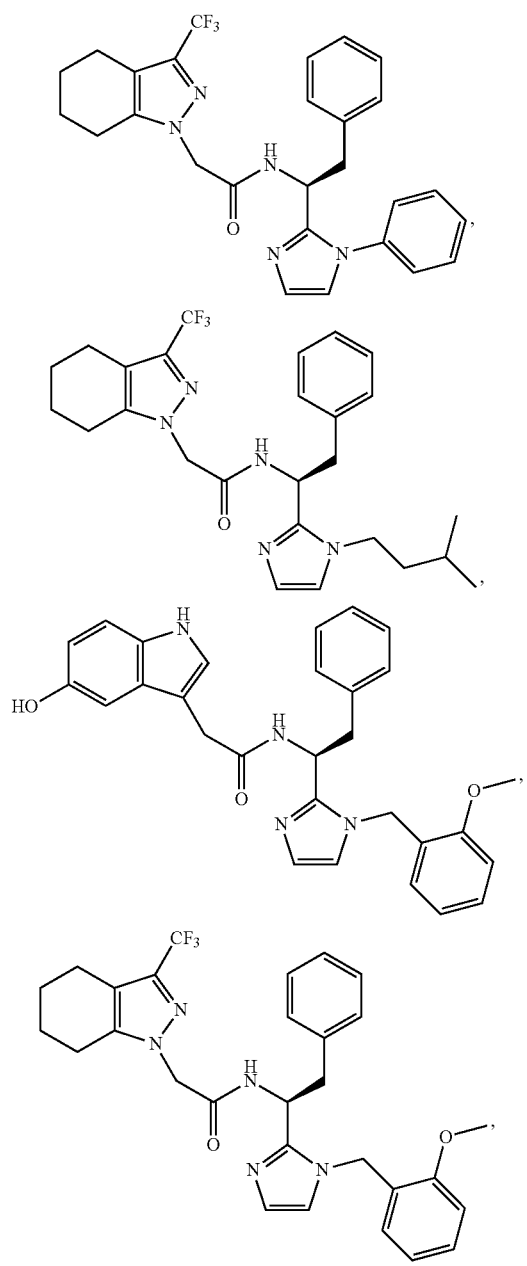
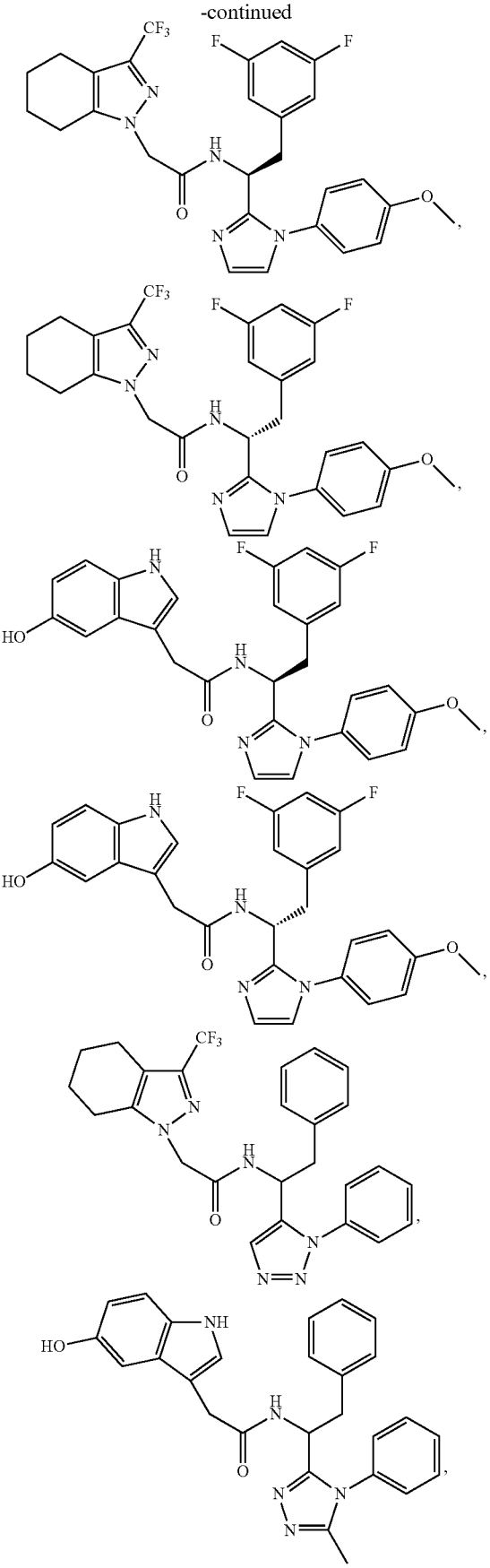

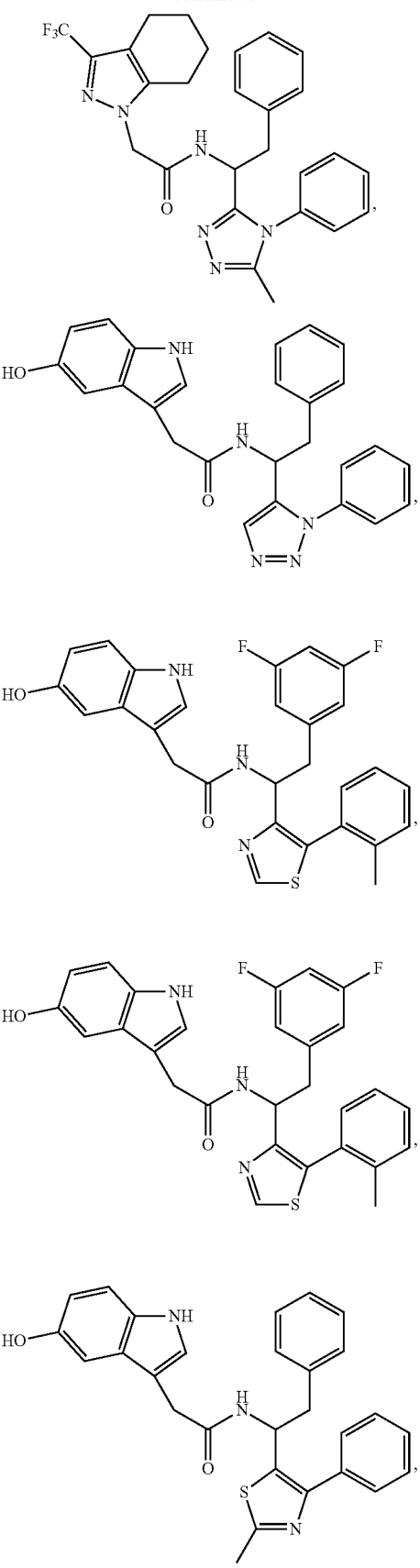

91
-continued
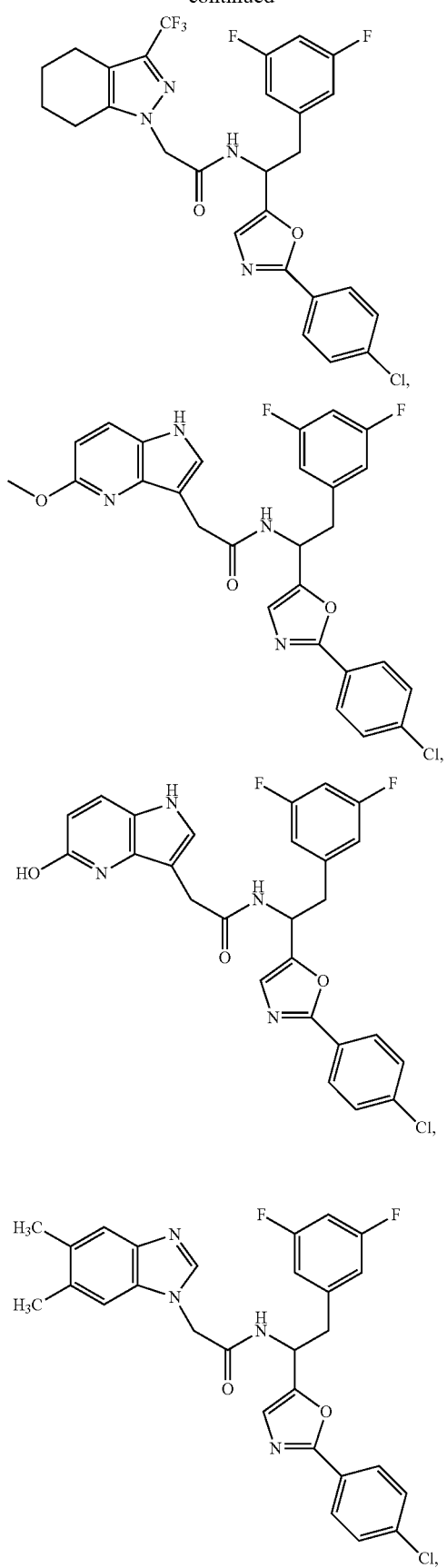
92
-continued
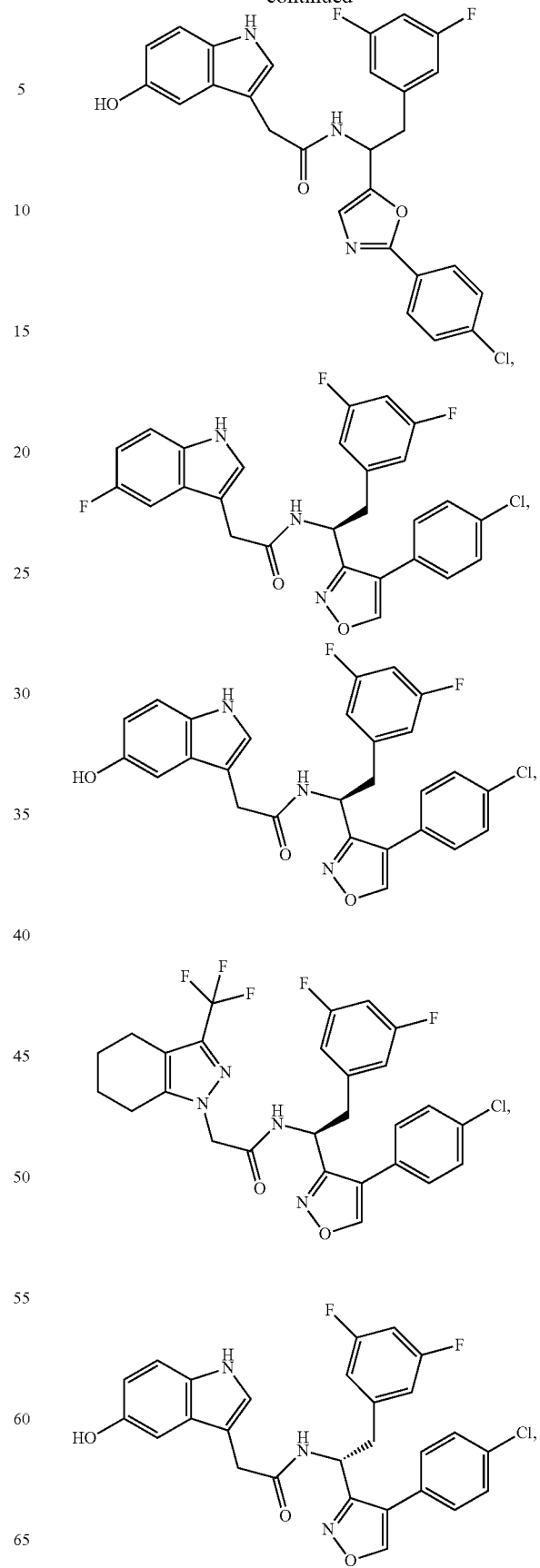

-continued
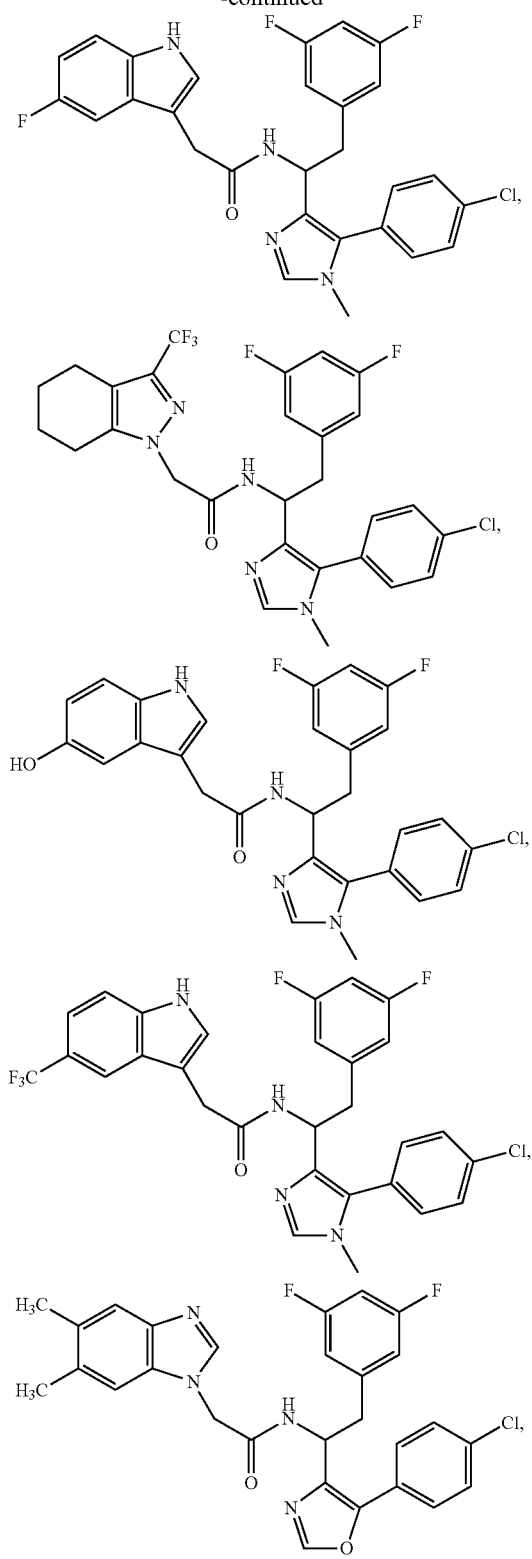
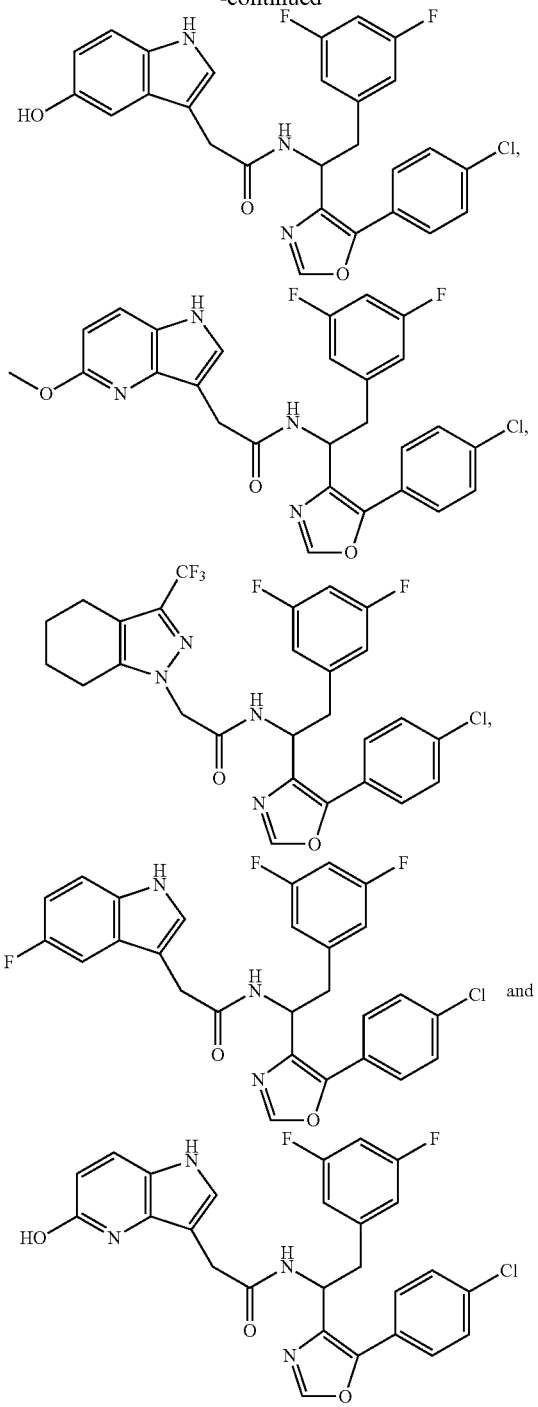
and salts thereof.
15. A pharmaceutical composition comprising a compound of claim 1, or a pharmaceutically acceptable salt thereof, and a pharmaceutically acceptable carrier.
* * * * *